US009409954B2

(12) United States Patent
Cook et al.

(10) Patent No.: US 9,409,954 B2
(45) Date of Patent: Aug. 9, 2016

(54) RECOMBINANT NON-PATHOGENIC MAREK'S DISEASE VIRUS CONSTRUCTS ENCODING INFECTIOUS LARYNGOTRACHEITIS VIRUS AND NEWCASTLE DISEASE VIRUS ANTIGENS

(71) Applicant: Intervet Inc., Summit, NJ (US)

(72) Inventors: Stephanie Cook, Omaha, NE (US);
Mohamad Morsey, Omaha, NE (US);
Gary Petersen, Omaha, NE (US);
Paulus Jacobus Antonius Sondermeijer, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/533,666

(22) Filed: Nov. 5, 2014

(65) Prior Publication Data
US 2015/0344528 A1 Dec. 3, 2015

Related U.S. Application Data

(62) Division of application No. 13/655,858, filed on Oct. 19, 2012, now Pat. No. 8,932,604.

(60) Provisional application No. 61/549,844, filed on Oct. 21, 2011.

(51) Int. Cl.
*C07K 14/005* (2006.01)
*C12N 7/00* (2006.01)
*A61K 39/12* (2006.01)
*C12N 15/86* (2006.01)
*A61K 39/245* (2006.01)
*A61K 39/00* (2006.01)

(52) U.S. Cl.
CPC ............... *C07K 14/005* (2013.01); *A61K 39/12* (2013.01); *A61K 39/245* (2013.01); *C12N 7/00* (2013.01); *C12N 15/86* (2013.01); *A61K 2039/5254* (2013.01); *A61K 2039/545* (2013.01); *A61K 2039/552* (2013.01); *A61K 2039/70* (2013.01); *C12N 2710/16311* (2013.01); *C12N 2710/16321* (2013.01); *C12N 2710/16334* (2013.01); *C12N 2710/16343* (2013.01); *C12N 2720/10011* (2013.01); *C12N 2720/10034* (2013.01); *C12N 2760/18011* (2013.01); *C12N 2760/18034* (2013.01); *C12N 2760/18111* (2013.01); *C12N 2760/18134* (2013.01)

(58) Field of Classification Search
CPC .................. A61K 2039/552; A61K 2039/525; A61K 39/295; A61K 2039/70; A61K 38/162; A61K 39/17; A61K 39/245; A61K 39/12; A61K 2039/545; A61K 2039/52; C12N 7/00; C12N 15/86; C12N 2760/18643; C12N 2760/18134; C12N 2760/18143; C12N 15/869; C12N 2740/16034; C12N 2760/16051; C12N 2760/18011; C12N 2760/18021; C12N 2760/18022; C12N 2760/18034; C12N 2760/18043; C12N 2710/16311; C12N 2760/18111; C12N 2720/10011; C12N 2710/16321; C12N 2720/10034; C07K 14/005; C07K 13/1027
See application file for complete search history.

(56) References Cited

U.S. PATENT DOCUMENTS

| | | | | |
|---|---|---|---|---|
| 5,187,087 A | * | 2/1993 | Sondermeijer | ...... C07K 14/005 424/199.1 |
| 5,223,424 A | | 6/1993 | Cochran et al. | |
| 5,250,298 A | | 10/1993 | Gelb, Jr. | |
| 5,273,876 A | | 12/1993 | Hock et al. | |
| 5,279,965 A | | 1/1994 | Keeler, Jr. | |
| 5,310,678 A | | 5/1994 | Bingham et al. | |
| 5,733,554 A | | 3/1998 | Audonnet et al. | |
| 5,830,745 A | | 11/1998 | Hock et al. | |
| 5,834,305 A | | 11/1998 | Cochran et al. | |
| 5,853,733 A | * | 12/1998 | Cochran | ................ C12N 15/86 414/199.1 |
| 5,919,461 A | * | 7/1999 | van der Marel | ...... C07K 14/005 424/130.1 |
| 5,928,648 A | * | 7/1999 | Cochran | .............. C07K 14/005 424/199.1 |
| 5,961,982 A | * | 10/1999 | Cochran | ................ A61K 39/12 424/199.1 |
| 5,965,138 A | * | 10/1999 | Cochran | ................ C12N 15/86 424/186.1 |
| 5,980,906 A | | 11/1999 | Audonnet et al. | |
| 6,033,670 A | | 3/2000 | Bublot et al. | |
| 6,048,535 A | | 4/2000 | Sharma | |
| 6,121,043 A | | 9/2000 | Cochran et al. | |

(Continued)

FOREIGN PATENT DOCUMENTS

| | | |
|---|---|---|
| CA | 2050850 A1 | 3/1992 |
| EP | 0227414 B1 | 5/1991 |
| EP | 0477056 A1 | 3/1992 |
| EP | 0332677 B1 | 7/1995 |
| EP | 1026246 A1 | 10/2000 |

(Continued)

OTHER PUBLICATIONS

Afonso et al., "The Genome of Turkey Herpesvirus", Journal of Virology, 2001, pp. 971-978, vol. 75(2).
Coppo et al., "Immune Responses to Infectious Laryngotracheitis Virus", Developmental and Comparative Immunology, 2013, pp. 454-462, vol. 41(3).

(Continued)

*Primary Examiner* — Rachel B Gill

(57) ABSTRACT

Recombinant multivalent non-pathogenic Marek's Disease virus constructs that encode and express both Infectious Laryngotracheitis Virus and Newcastle Disease virus protein antigens, and methods of their use in poultry vaccines.

21 Claims, 2 Drawing Sheets

(56) References Cited

U.S. PATENT DOCUMENTS

| | | | |
|---|---|---|---|
| 6,183,753 B1* | 2/2001 | Cochran | C12N 7/00 424/199.1 |
| 6,299,882 B1* | 10/2001 | Junker | C12N 15/86 424/199.1 |
| 6,322,780 B1* | 11/2001 | Lee | C07K 14/005 424/93.2 |
| 6,406,702 B1 | 6/2002 | Sharma | |
| 6,875,856 B2 | 4/2005 | Wild et al. | |
| 6,913,751 B2* | 7/2005 | Cochran | C07K 14/005 424/199.1 |
| 7,314,715 B2 | 1/2008 | Cochran et al. | |
| 8,932,604 B2* | 1/2015 | Cook | A61K 39/245 424/184.1 |
| 2002/0081316 A1* | 6/2002 | Cochran | C07K 14/005 424/199.1 |
| 2002/0085999 A1* | 7/2002 | Lee | C07K 15/005 424/93.21 |
| 2005/0202045 A1* | 9/2005 | Cochran | A61K 39/12 424/229.1 |
| 2009/0191239 A1* | 7/2009 | Wild | C07K 14/005 424/205.1 |
| 2012/0052089 A1 | 3/2012 | Bublot | |

FOREIGN PATENT DOCUMENTS

| | | |
|---|---|---|
| EP | 0996464 B1 | 12/2003 |
| EP | 0794257 B1 | 10/2006 |
| EP | 1298139 B1 | 5/2007 |
| EP | 0776361 B1 | 11/2007 |
| EP | 1801204 B1 | 2/2011 |
| WO | WO8704663 A1 | 7/1987 |
| WO | WO9203554 A1 | 3/1992 |
| WO | WO9325665 A1 | 12/1993 |
| WO | WO9605291 A1 | 2/1996 |
| WO | WO9629396 A1 | 9/1996 |
| WO | WO9837216 A1 | 11/1996 |
| WO | WO0061736 A2 | 10/2000 |
| WO | 03075843 A2 | 9/2003 |
| WO | WO2010125084 A1 | 11/2010 |
| WO | 2015/032909 A1 | 3/2015 |
| WO | 2015/032910 A1 | 3/2015 |

OTHER PUBLICATIONS

Dartiel et al., "Herpesvirus of Turkey Recombinant Viruses Expressing Infectious Bursal Disease Virus (IBDV) VP2 Immunogen Induce Protection Against an IBDV Virulent Challenge in Chickens", Virology, 1995, pp. 481-490, vol. 211.

Fuchs et al., "Molecular Biology of Avian Infectious Laryngotracheitis Virus", Veterinary Research, 2007, pp. 261-279, vol. 38.

Fynan et al., "Persistence of Marek's Disease Virus in a Subpopulation of B Cells that is Transformed by Avian Leukosis Virus, but not in Normal Bursal B Cells", Journal of Virology, 1992, pp. 5860-5866, vol. 66(10).

Gibbs et al., "Extensive Homology Exists Between Marek Disease Herpesvirus and its Vaccine Virus, Herpesvirus of Turkeys", Proceedings of the National Academy of Sciences, USA, 1984, pp. 3365-3369, vol. 81.

PCT International Search Report for corresponding PCTEP2012070727, mailed on Jan. 14, 2013.

Jarosinski, K.W., "Dual Infection and Superinfection Inhibition of Epithelial Skin Cells by Two Alphaherpesviruses Co-occur in the Natural Host", PLoS One, 2012, pp. 1-15, 7-5:e37428.

Johnson et al., "Protection Against Infectious Laryngotracheitis by in Ovo Vaccination with Commercially Available Viral Vector Recombinant Vaccines", Avian Diseases, 2010, pp. 1251-1259, vol. 54.

Kingham et al., "The Genome of Herpesvirus of Turkeys: Comparative Analysis with Marek's Disease Viruses", Journal of General Virology, 2001, pp. 1123-1135, vol. 82.

Kulikova et al., "Effects of Infections Bursal Disease Vaccination Strains on the Immune System of Leghorn Chickens", Acta Vet. BRNO, 2004, pp. 205-209, vol. 73.

Lee et al., "The Complete Unique Long Sequence and the Overall Genomic Organization of the GA strain of Marek's Disease Virus", Proceedings of the National Academy of Sciences, USA, 2000, pp. 6091-6096, vol. 97(11).

Martin et al., "Genetic and Biochemical Characterization of the Thymidine Kinase Gene from Herpesvirus of Turkeys", Journal of Virology, 1989, pp. 547-553, vol. 63(6).

Mazariegos et al., "Pathogenicity and Immunosuppressive Properties of Infectious Bursal Disease Intermediate", Avian Diseases, 1990, pp. 203-208, vol. 34.

Morgan et al., "Protection of Chickens from Newcastle and Marek's Diseases with a Recombinant Herpesvirus of Turkeys Vaccine Expressing the Newcastle Disease Virus Fusion Protein", Avian Diseases, 1992, pp. 858-870, vol. 36(4).

Murthy et al., "Pathogenesis of Marek's Disease: Effect of Immunization with Inactivated Viral and Tumor-Associated Antigens", Infection and Immunity, 1979, pp. 547-533, vol. 26(2).

Palya et al., "Advancement in vaccination against Newcastle disease: recombinant HVT NDV provides high clinical protection and reduces challenge virus shedding with the absence of vaccine reactions", Avian Disease, 2012, pp. 282-287, vol. 56(2).

Parsheera, "Decisions taken in the 92nd Meeting of the Genetic Engineering Approval Committee", The 92nd Meeting of the Genetically Engineering Approval Committee (GEAC), 2009, pp. 1-5 —.

PCT International Search Report for corresponding PCT/EP2012/07028, mailed on Mar. 13, 2013.

Petherbridge et al., "Cloning of Gallid Herpesvirus 3 (Marek's Disease Virus Serotype-2)", Journal of Virological Methods, 2009, pp. 11-17, vol. 158.

Reddy et al., "Protective Efficacy of a Recombinant Herpesvirus of turkeys as an in Ovo Vaccine Against Newcastle and Marek's Diseases in Specific-Pathogen-Free Chickens", Vaccine, 1996, pp. 469-477, vol. 14(6).

Saiki et al., "Primer-Directed Enzymatic Amplification of DNA with a Thermostable DNA Polymerase", Science, 1988, pp. 487-491, vol. 239.

Senne et al., "Control of Newcastle Disease by Vaccination", Dev. Biol. (Basel), 2004, pp. 165-170, vol. 119.

Sharma et al., "Field Trial in Commercial Broilers with a Multivalent in Ovo Vaccine Comprising a Mixture of Live Viral Vaccines Against Marek's Disease, Infectious Bursal Disease, Newcastle Disease, and Fowl Pox", Avian Diseases, 2002, pp. 613-622, vol. 46(3).

Sondermeijer et al., "Avian Herpesvirus as a Live Viral Vector for the Expression of Heterologous Antigens", Vaccine, 1993, pp. 349-358, vol. 11.

Sun et al., "Protection of Chickens from Newcastle Disease and Infectious Laryngotracheitis with a Recombinant Fowlpox Virus Co-Expressing the F, HN Genes of Newcastle Disease Virus and gB Gene of Infectious Laryngotracheitis Virus", Avian Diseases, 2008, pp. 111-117, vol. 52.

Thompson et al., "Clustal W: Improving the Sensitivity of Progressive Multiple Sequence Alignment through Sequence Weighting, Position-Specific Gap Penalties and Weight Matrix Choice", Nucleic Acids Research, 1994, pp. 4673-5645, vol. 22(22).

Tsukamoto et al., "Complete, Long-Lasting Protection Against Lethal Infectious Bursal Disease Virus Challenge by a Single Vaccination with an Avian Herepesvirus Vector Expressing VP2 Antigens", Journal of Virology, 2002, pp. 5637-5645, vol. 76(11).

Tsukamoto et al., "Protection of Chickens Against Very Virulent Infectious Bursal Disease Virus (IBDV) and Marek's Disease Virus (MDV) with a Recombinant MDV Expressing IBDV VP2", Virology, 1999, pp. 352-362, vol. 257(2).

Vagnozzi et al., "Protection Induced by Commercially Available Live-Attenuated and Recombinant Viral Vector Vaccines Against Infectious Laryngotracheitis Virus in Broiler Chickens", Avian Pathology, 2012, pp. 21-31, vol. 41(1).

Van Zijl et al., "Regeneration of Herpesviruses from Molecularly Cloned Subgenomic Fragments", Journal of Virology, 1988, pp. 2191-2195, vol. 62(6).

Wild et al., "A Genomic map of Infectious Laryngotracheitis Virus and the Sequence and Organization of Genes Present in the Unique Short and Flanking Regions", Virus Genes, 1996, pp. 107-116, vol. 12(2).

Wu et al., "Molecular Detection and Differentiation of Infectious Bursal Disease Virus", Avian Diseases, 2007, pp. 515-526, vol. 51.

* cited by examiner

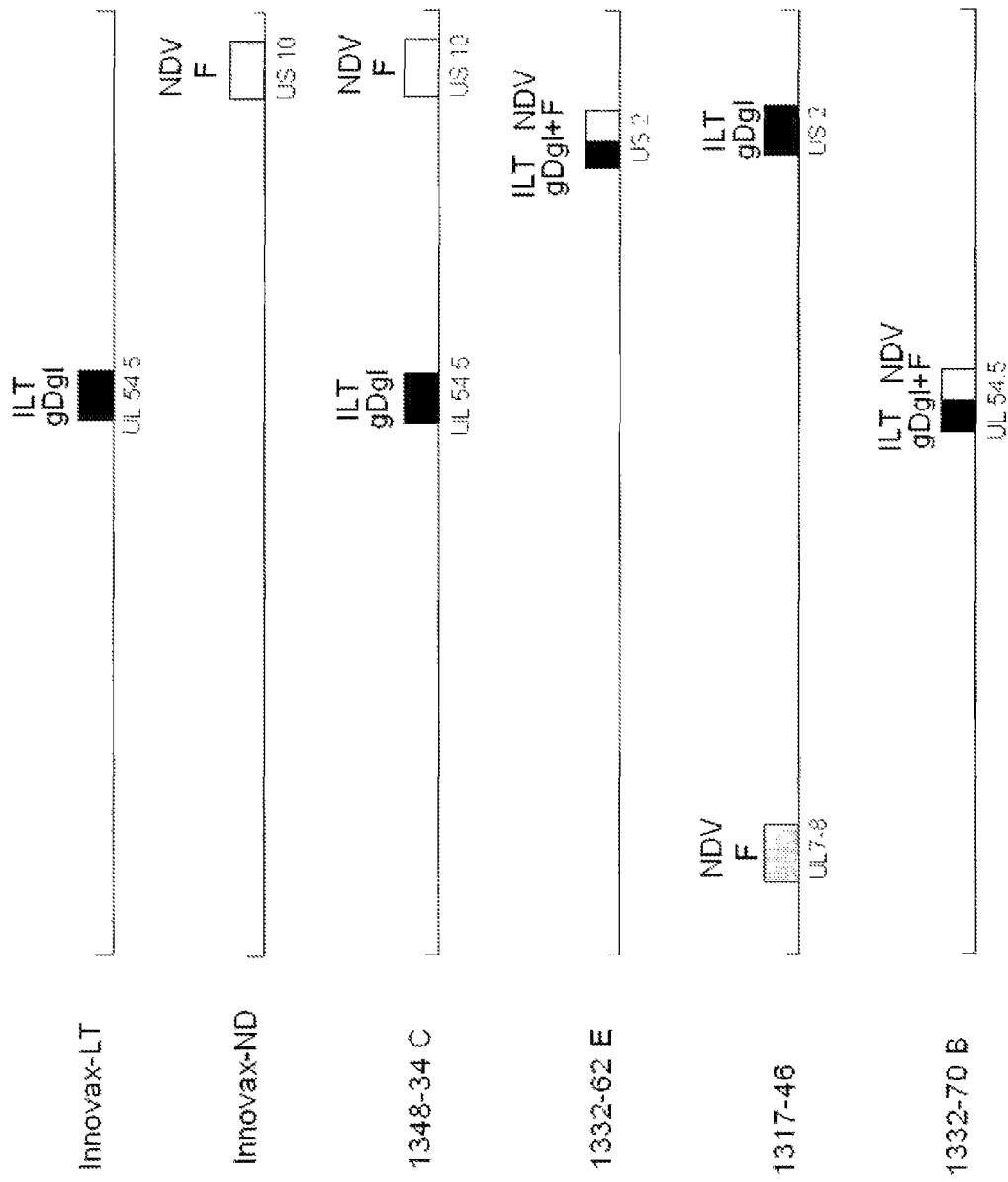

SEQUENCE LISTING

```
<160> NUMBER OF SEQ ID NOS: 17

<210> SEQ ID NO 1
<211> LENGTH: 1305
<212> TYPE: DNA
<213> ORGANISM: Infectious laryngotracheitis virus

<400> SEQUENCE: 1
atgcaccgtc ctcatctcag acggcactcg cgttactacg cgaaaggaga ggtgcttaac      60
aaacacatgg attgcggtgg aaaacggtgc tgctcaggcg cagctgtatt cactcttttc     120
tggacttgtg tcaggattat gcgggagcat atctgctttg tacgcaacgc tatggaccgc     180
catttatttt tgaggaatgc tttttggact atcgtactgc tttcttcctt cgctagccag     240
agcaccgccg ccgtcacgta cgactacatt ttaggccgtc gcgcgctcga cgcgctaacc     300
ataccggcgg ttggcccgta taacagatac ctcactaggg tatcaagagg ctgcgacgtt     360
gtcgagctca acccgatttc taacgtggac gacatgatat cggcggccaa agaaaaagag     420
aaggggggcc ctttcgaggc ctccgtcgtc tggttctacg tgattaaggg cgacgacggc     480
gaggacaagt actgtccaat ctatagaaaa gagtacaggg aatgtggcga cgtacaactg     540
ctatctgaat gcgccgttca atctgcacag atgtgggcag tggactatgt tcctagcacc     600
cttgtatcgc gaaatggcgc gggactgact atattctccc ccactgctgc gctctctggc     660
caatacttgc tgaccctgaa aatcgggaga tttgcgcaaa cagctctcgt aactctagaa     720
gttaacgatc gctgtttaaa gatcgggtcg cagcttaact tttaccgtc gaaatgctgg      780 acaacagaac agtatcagac tggatttcaa ggcgaacacc tttatccgat cgcagacacc     840
```

-continued

```
aatacacgac acgcggacga cgtatatcgg ggatacgaag atattctgca gcgctggaat      900
aatttgctga ggaaaaagaa tcctagcgcg ccagaccctc gtccagatag cgtcccgcaa      960
gaaattcccg ctgtaaccaa gaaagcggaa gggcgcaccc cggacgcaga aagcagcgaa     1020
aagaaggccc ctccagaaga ctcggaggac gacatgcagg cagaggcttc tggagaaaat     1080
cctgccgccc tccccgaaga cgacgaagtc cccgaggaca ccgagcacga tgatccaaac     1140
tcggatcctg actattacaa tgacatgccc gccgtgatcc cggtggagga gactactaaa     1200
agttctaatg ccgtctccat gcccatattc gcggcgttcg tagcctgcgc ggtcgcgctc     1260
gtggggctac tggtttggag catcgtaaaa tgcgcgcgta gctaa                    1305
```

<210> SEQ ID NO 2
<211> LENGTH: 434
<212> TYPE: PRT
<213> ORGANISM: Infectious laryngotracheitis virus

<400> SEQUENCE: 2

```
Met His Arg Pro His Leu Arg Arg His Ser Arg Tyr Tyr Ala Lys Gly
1               5                   10                  15

Glu Val Leu Asn Lys His Met Asp Cys Gly Gly Lys Arg Cys Cys Ser
            20                  25                  30

Gly Ala Ala Val Phe Thr Leu Phe Trp Thr Cys Val Arg Ile Met Arg
        35                  40                  45

Glu His Ile Cys Phe Val Arg Asn Ala Met Asp Arg His Leu Phe Leu
    50                  55                  60

Arg Asn Ala Phe Trp Thr Ile Val Leu Leu Ser Ser Phe Ala Ser Gln
65                  70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255

Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285
```

```
Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser

<210> SEQ ID NO 3
<211> LENGTH: 1089
<212> TYPE: DNA
<213> ORGANISM: Infectious laryngotracheitis virus

<400> SEQUENCE: 3
atggcatcgc tacttggaac tctggctctc cttgccgcga cgctcgcacc cttcggcgcg      60
atgggaatcg tgatcactgg aaatcacgtc tccgccagga ttgacgacga tcacatcgtg     120
atcgtcgcgc ctcgccccga agctacaatt caactgcagc tatttttcat gcctggccag     180
agaccccaca aaccctactc aggaaccgtc cgcgtcgcgt ttcggtctga tataacaaac     240
cagtgctacc aggaacttag cgaggagcgc tttgaaaatt gcactcatcg atcgtcttct     300 gttttttgtcg gctgtaaagt gaccgagtac acgttctccg cctcgaacag actaaccgga     360
cctccacacc cgtttaagct cactatacga aatcctcgtc cgaacgacag cgggatgttc     420
tacgtaattg ttcggctaga cgacaccaaa gaacccattg acgtcttcgc gatccaacta     480
tcggtgtatc aattcgcgaa caccgccgcg actcgcggac tctattccaa ggcttcgtgt     540
cgcaccttcg gattacctac cgtccaactt gaggcctatc tcaggaccga ggaaagttgg     600
cgcaactggc aagcgtacgt tgccacggag gccacgacga ccagcgccga ggcgacaacc     660
ccgacgcccg tcactgcaac cagcgcctcc gaacttgaag cggaacactt tacctttccc     720
tggctagaaa atggcgtgga tcattacgaa ccgacacccg caaacgaaaa ttcaaacgtt     780
actgtccgtc tcgggacaat gagccctacg ctaattgggg taaccgtggc tgccgtcgtg     840
agcgcaacga tcggcctcgt cattgtaatt tccatcgtca ccagaaacat gtgcaccccg     900
caccgaaaat tagacacggt ctcgcaagac gacgaagaac gttcccaaac tagaagggaa     960
tcgcgaaaat ttgacccat ggttgcgtgc gaaataaaca agggggctga ccaggatagt    1020
gaacttgtgg aactggttgc gattgttaac ccgtctgcgc taagctcgcc cgactcaata    1080
aaaatgtga                                                            1089
```

-continued

<210> SEQ ID NO 4
<211> LENGTH: 362
<212> TYPE: PRT
<213> ORGANISM: Infectious laryngotracheitis virus

<400> SEQUENCE: 4

```
Met Ala Ser Leu Leu Gly Thr Leu Ala Leu Leu Ala Ala Thr Leu Ala
1               5                   10                  15

Pro Phe Gly Ala Met Gly Ile Val Ile Thr Gly Asn His Val Ser Ala
            20                  25                  30

Arg Ile Asp Asp Asp His Ile Val Ile Val Ala Pro Arg Pro Glu Ala
        35                  40                  45

Thr Ile Gln Leu Gln Leu Phe Phe Met Pro Gly Gln Arg Pro His Lys
    50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Ser Val Phe Val Gly Cys Lys Val Thr Glu Tyr Thr Phe
            100                 105                 110

Ser Ala Ser Asn Arg Leu Thr Gly Pro Pro His Pro Phe Lys Leu Thr
        115                 120                 125

Ile Arg Asn Pro Arg Pro Asn Asp Ser Gly Met Phe Tyr Val Ile Val
    130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
                165                 170                 175

Lys Ala Ser Cys Arg Thr Phe Gly Leu Pro Thr Val Gln Leu Glu Ala
            180                 185                 190

Tyr Leu Arg Thr Glu Glu Ser Trp Arg Asn Trp Gln Ala Tyr Val Ala
        195                 200                 205

Thr Glu Ala Thr Thr Thr Ser Ala Glu Ala Thr Thr Pro Thr Pro Val
    210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
                245                 250                 255

Asn Ser Asn Val Thr Val Arg Leu Gly Thr Met Ser Pro Thr Leu Ile
            260                 265                 270

Gly Val Thr Val Ala Ala Val Val Ser Ala Thr Ile Gly Leu Val Ile
        275                 280                 285

Val Ile Ser Ile Val Thr Arg Asn Met Cys Thr Pro His Arg Lys Leu
    290                 295                 300

Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
                325                 330                 335

Asp Gln Asp Ser Glu Leu Val Glu Leu Val Ala Ile Val Asn Pro Ser
            340                 345                 350

Ala Leu Ser Ser Pro Asp Ser Ile Lys Met
        355                 360
```

<210> SEQ ID NO 5
<211> LENGTH: 1662
<212> TYPE: DNA
<213> ORGANISM: Newcastle disease virus

<400> SEQUENCE: 5

| | | | | | |
|---|---|---|---|---|---|
| atgggccca | gaccttctac | caagaaccca | gtacctatga | tgctgactgt | ccgagtcgcg | 60 |
| ctggtactga | gttgcatctg | tccggcaaac | tccattgatg | caggcctct | gcggctgca | 120 |
| ggaattgtgg | ttacaggaga | caaagccgtc | aacatataca | cctcatccca | gacaggatca | 180 |
| atcatagtta | agctcctccc | gaatctgccc | aaggataagg | aggcatgtgc | gaaagccccc | 240 |
| ttggatgcat | acaacaggac | attgaccact | ttgctcaccc | ccttggtga | ctctatccgt | 300 |
| aggatacaag | agtctgtgac | tacatctgga | gggggagac | aggggcgcct | tataggcgcc | 360 |
| attattggcg | gtgtggctct | tgggttgca | actgccgcac | aaataacagc | ggccgcagct | 420 |
| ctgatacaag | ccaaacaaaa | tgctgccaac | atcctccgac | ttaaagagag | cattgccgca | 480 |
| accaatgagg | ctgtgcatga | ggtcactgac | ggattatcgc | aactagcagt | ggcagttggg | 540 |
| aagatgcagc | agtttgttaa | tgaccaattt | aataaaacag | ctcaggaatt | agactgcatc | 600 |
| aaaattgcac | agcaagttgg | tgtagagctc | aacctgtacc | taaccgaatt | gactacagta | 660 |
| ttcggaccac | aaatcacttc | acctgcttta | aacaagctga | ctattcaggc | actttacaat | 720 |
| ctagctggtg | aaatatgga | ttacttattg | actaagttag | gtgtagggaa | caatcaactc | 780 |
| agctcattaa | tcggtagcgg | cttaatcacc | ggtaaccta | ttctatacga | ctcacagact | 840 |
| caactcttgg | gtatacaggt | aactctacct | tcagtcggga | agctaaataa | tatgcgtgcc | 900 |
| acctacttgg | aaaccttatc | cgtaagcaca | accaggggat | ttgcctcggc | acttgtccca | 960 |
| aaagtggtga | cacaggtcgg | ttctgtgata | aagaacttg | acacctcata | ctgtatagaa | 1020 |
| actgacttac | atttatattg | tacaagaata | gtaacgttcc | ctatgtcccc | tggtatttat | 1080 |
| tcctgcttga | gcggcaatac | gtcggcctgt | atgtactcaa | agaccgaagg | cgcacttact | 1140 |
| acaccataca | tgactatcaa | aggttcagtc | atcgccaact | gcaagatgac | aacatgtaga | 1200 |
| tgtgtaaaacc | ccccgggtat | catatcgcaa | aactatggag | aagccgtgtc | tctaatagat | 1260 |
| aaacaatcat | gcaatgtttt | atccttaggc | gggataactt | taaggctcag | tggggaattc | 1320 |
| gatgtaactt | atcagaagaa | tatctcaata | caagattctc | aagtaataat | aacaggcaat | 1380 |
| cttgatatct | caactgagct | tgggaatgtc | aacaactcga | tcagtaatgc | tttgaataag | 1440 |
| ttagaggaaa | gcaacagaaa | actagacaaa | gtcaatgtca | aactgactag | cacatctgct | 1500 |
| ctcattacct | atatcgtgtt | gactatcata | tctcttgttt | ttggtatact | tagcctgatt | 1560 |
| ctagcatgct | acctaatgta | caagcaaaag | gcgcaacaaa | agaccttatt | atggcttggg | 1620 |
| aataatactc | tagatcagat | gagagccact | acaaaaatgt | ga | 1662 |

<210> SEQ ID NO 6
<211> LENGTH: 553
<212> TYPE: PRT
<213> ORGANISM: Newcastle disease virus

<400> SEQUENCE: 6

Met Gly Pro Arg Pro Ser Thr Lys Asn Pro Val Pro Met Met Leu Thr
1               5                   10                  15

Val Arg Val Ala Leu Val Leu Ser Cys Ile Cys Pro Ala Asn Ser Ile
            20                  25                  30

Asp Gly Arg Pro Leu Ala Ala Ala Gly Ile Val Val Thr Gly Asp Lys
        35                  40                  45

-continued

```
Ala Val Asn Ile Tyr Thr Ser Ser Gln Thr Gly Ser Ile Ile Val Lys
 50                  55                  60

Leu Leu Pro Asn Leu Pro Lys Asp Lys Glu Ala Cys Ala Lys Ala Pro
 65                  70                  75                  80

Leu Asp Ala Tyr Asn Arg Thr Leu Thr Thr Leu Leu Thr Pro Leu Gly
                 85                  90                  95

Asp Ser Ile Arg Arg Ile Gln Glu Ser Val Thr Thr Ser Gly Gly Gly
                100                 105                 110

Arg Gln Gly Arg Leu Ile Gly Ala Ile Ile Gly Val Ala Leu Gly
                115                 120                 125

Val Ala Thr Ala Ala Gln Ile Thr Ala Ala Ala Leu Ile Gln Ala
130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
                180                 185                 190

Thr Ala Gln Glu Leu Asp Cys Ile Lys Ile Ala Gln Gln Val Gly Val
                195                 200                 205

Glu Leu Asn Leu Tyr Leu Thr Glu Leu Thr Thr Val Phe Gly Pro Gln
210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
                260                 265                 270

Pro Ile Leu Tyr Asp Ser Gln Thr Gln Leu Leu Gly Ile Gln Val Thr
                275                 280                 285

Leu Pro Ser Val Gly Lys Leu Asn Asn Met Arg Ala Thr Tyr Leu Glu
290                 295                 300

Thr Leu Ser Val Ser Thr Thr Arg Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Thr Asp Leu His Leu Tyr Cys Thr Arg Ile Val Thr
                340                 345                 350

Phe Pro Met Ser Pro Gly Ile Tyr Ser Cys Leu Ser Gly Asn Thr Ser
                355                 360                 365

Ala Cys Met Tyr Ser Lys Thr Glu Gly Ala Leu Thr Thr Pro Tyr Met
                370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
                420                 425                 430

Thr Leu Arg Leu Ser Gly Glu Phe Asp Val Thr Tyr Gln Lys Asn Ile
                435                 440                 445

Ser Ile Gln Asp Ser Gln Val Ile Ile Thr Gly Asn Leu Asp Ile Ser
450                 455                 460
```

```
Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
            485                 490                 495

Ser Thr Ser Ala Leu Ile Thr Tyr Ile Val Leu Thr Ile Ile Ser Leu
        500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550
```

<210> SEQ ID NO 7
<211> LENGTH: 1698
<212> TYPE: DNA
<213> ORGANISM: Newcastle disease virus

<400> SEQUENCE: 7

```
atggatcgat cccggttggc gccctccagg tgcaggatgg gctccagacc ttctaccaag      60
aacccagcac ctatgatgct gactatccgg gtcgcgctgg tactgagttg catctgtccg     120
gcaaactcca ttgatggcag gcctcttgca gctgcaggaa ttgtggttac aggagacaaa     180
gcagtcaaca tatacacctc atcccagaca ggatcaatac tagttaagct cctcccgaat     240
ctgccaaagg ataaggaggc atgtgcgaaa gccccttgg atgcatacaa caggacattg     300
accactttgc tcacccccct tggtgactct atccgtagga cacaagagtc tgtgactaca     360
tctggagggg ggagacaggg gcgccttata ggcgccatta ttggcggtgt ggctcttggg     420
gttgcaactg ccgcacaaat aacagcggcc gcagctctga tacaagccaa acaaaatgct     480
gccaacatcc tccgacttaa agagagcatt gccgcaacca atgaggctgt gcatgaggtc     540
actgacggat tatcgcaact gcagtggca gttgggaaga tgcagcagtt cgttaatgac     600
caatttaata aaacagctca ggaattagac tgcatcaaaa ttgcacagca agttggtgta     660
gagctcaacc tgtacctaac cgaatcgact acagtattcg gccacaaat cacttcacct     720
gccttaaaca agctgactat tcaggcactt acaatctag ctggtgggaa tatggattac     780
ttattgacta agttaggtat agggaacaat caactcagct cattaatcgg tagcggctta     840
atcaccggta accctattct atacgactca cagactcaac tcttgggtat acaggtaact     900
taccttcag tcgggaacct aaataatatg cgtgccacct acttggaaac cttatccgta     960
agcacaacca ggggattgtgc ctcggcactt gtcccaaaag tggtgacacg ggtcggttct    1020
gtgatagaag aacttgacac ctcatactgt ataagaaactg acttagattt atattgtaca    1080
agaatagtaa cgttccctat gtcccctggt atttactcct gcttgagcgg caatacatcg    1140
gcctgtatgt actcaaagac cgaaggcgca cttactacac catatatgac tatcaaaggc    1200
tcagtcatcg ctaactgcaa gatgacaaca tgtagatgtg taaacccccc gggtatcata    1260
tcgcaaaact atggagaagc cgtgtctcta atagataaac aatcatgcaa tgttttatcc    1320
ttaggcggga taactttaag gctcagtggg gaattcgatg taacttatca aagaatatc    1380
tcaatacaag attctcaagt aataataaca ggcaatcttg atatctcaac tgagcttggg    1440
aatgtcaaca actcgatcag taatgccttg aataagttag aggaaagcaa cagaaaacta    1500
gacaaagtca atgtcaaact gaccagcaca tctgctctca ttacctatat cgttttgact    1560
atcatatctc ttgttttggg tatacttagc ctgattctag catgctacct aatgtacaag    1620
```

```
caaaaggcgc aacaaaagac cttattatgg cttgggaata ataccctaga tcagatgaga    1680
gccactacaa aatgtga                                                   1698
```

<210> SEQ ID NO 8
<211> LENGTH: 565
<212> TYPE: PRT
<213> ORGANISM: Newcastle disease virus

<400> SEQUENCE: 8

```
Met Asp Arg Ser Arg Leu Ala Pro Ser Arg Cys Arg Met Gly Ser Arg
1               5                   10                  15

Pro Ser Thr Lys Asn Pro Ala Pro Met Met Leu Thr Ile Arg Val Ala
            20                  25                  30

Leu Val Leu Ser Cys Ile Cys Pro Ala Asn Ser Ile Asp Gly Arg Pro
        35                  40                  45

Leu Ala Ala Ala Gly Ile Val Val Thr Gly Asp Lys Ala Val Asn Ile
    50                  55                  60

Tyr Thr Ser Ser Gln Thr Gly Ser Ile Ile Val Lys Leu Leu Pro Asn
65                  70                  75                  80

Leu Pro Lys Asp Lys Glu Ala Cys Ala Lys Ala Pro Leu Asp Ala Tyr
                85                  90                  95

Asn Arg Thr Leu Thr Thr Leu Leu Thr Pro Leu Gly Asp Ser Ile Arg
            100                 105                 110

Arg Ile Gln Glu Ser Val Thr Thr Ser Gly Gly Arg Gln Gly Arg
        115                 120                 125

Leu Ile Gly Ala Ile Ile Gly Gly Val Ala Leu Gly Val Ala Thr Ala
    130                 135                 140

Ala Gln Ile Thr Ala Ala Ala Ala Leu Ile Gln Ala Lys Gln Asn Ala
145                 150                 155                 160

Ala Asn Ile Leu Arg Leu Lys Glu Ser Ile Ala Ala Thr Asn Glu Ala
                165                 170                 175

Val His Glu Val Thr Asp Gly Leu Ser Gln Leu Ala Val Ala Val Gly
            180                 185                 190

Lys Met Gln Gln Phe Val Asn Asp Gln Phe Asn Lys Thr Ala Gln Glu
        195                 200                 205

Leu Asp Cys Ile Lys Ile Ala Gln Gln Val Gly Val Glu Leu Asn Leu
    210                 215                 220

Tyr Leu Thr Glu Ser Thr Thr Val Phe Gly Pro Gln Ile Thr Ser Pro
225                 230                 235                 240

Ala Leu Asn Lys Leu Thr Ile Gln Ala Leu Tyr Asn Leu Ala Gly Gly
                245                 250                 255

Asn Met Asp Tyr Leu Leu Thr Lys Leu Gly Ile Gly Asn Asn Gln Leu
            260                 265                 270

Ser Ser Leu Ile Gly Ser Gly Leu Ile Thr Gly Asn Pro Ile Leu Tyr
        275                 280                 285

Asp Ser Gln Thr Gln Leu Leu Gly Ile Gln Val Thr Leu Pro Ser Val
    290                 295                 300

Gly Asn Leu Asn Asn Met Arg Ala Thr Tyr Leu Glu Thr Leu Ser Val
305                 310                 315                 320

Ser Thr Thr Arg Gly Phe Ala Ser Ala Leu Val Pro Lys Val Val Thr
                325                 330                 335

Arg Val Gly Ser Val Ile Glu Glu Leu Asp Thr Ser Tyr Cys Ile Glu
            340                 345                 350
```

```
Thr Asp Leu Asp Leu Tyr Cys Thr Arg Ile Val Thr Phe Pro Met Ser
            355                 360                 365
Pro Gly Ile Tyr Ser Cys Leu Ser Gly Asn Thr Ser Ala Cys Met Tyr
    370                 375                 380
Ser Lys Thr Glu Gly Ala Leu Thr Thr Pro Tyr Met Thr Ile Lys Gly
385                 390                 395                 400
Ser Val Ile Ala Asn Cys Lys Met Thr Thr Cys Arg Cys Val Asn Pro
                405                 410                 415
Pro Gly Ile Ile Ser Gln Asn Tyr Gly Glu Ala Val Ser Leu Ile Asp
            420                 425                 430
Lys Gln Ser Cys Asn Val Leu Ser Leu Gly Gly Ile Thr Leu Arg Leu
                435                 440                 445
Ser Gly Glu Phe Asp Val Thr Tyr Gln Lys Asn Ile Ser Ile Gln Asp
    450                 455                 460
Ser Gln Val Ile Ile Thr Gly Asn Leu Asp Ile Ser Thr Glu Leu Gly
465                 470                 475                 480
Asn Val Asn Asn Ser Ile Ser Asn Ala Leu Asn Lys Leu Glu Glu Ser
                485                 490                 495
Asn Arg Lys Leu Asp Lys Val Asn Val Lys Leu Thr Ser Thr Ser Ala
            500                 505                 510
Leu Ile Thr Tyr Ile Val Leu Thr Ile Ile Ser Leu Val Phe Gly Ile
            515                 520                 525
Leu Ser Leu Ile Leu Ala Cys Tyr Leu Met Tyr Lys Gln Lys Ala Gln
            530                 535                 540
Gln Lys Thr Leu Leu Trp Leu Gly Asn Asn Thr Leu Asp Gln Met Arg
545                 550                 555                 560
Ala Thr Thr Lys Met
                565

<210> SEQ ID NO 9
<211> LENGTH: 527
<212> TYPE: DNA
<213> ORGANISM: Infectious laryngotracheitis virus

<400> SEQUENCE: 9
aaacagctgt actacagagt aaccgatgga agaacatcgg tccagctaat gtgcctgtcg      60
tgcacgagcc attctccgga accttactgt cttttcgaca cgtctcttat agcgagggaa     120
aaagatatcg cgccagagtt atactttacc tctgatccgc aaacggcata ctgcacaata     180
actctgccgt ccggcgttgt tccgagattc gaatggagcc ttaataatgt ttcactgccg     240
gaatatttga cggccacgac cgttgtttcg cataccgctg ccaaagtac agtgtggaag      300 agcagcgcga gagcaggcga ggcgtggatt tctggccggg gaggcaatat atacgaatgc     360
accgtcctca tctcagacgg cactcgcgtt actacgcgaa aggagaggtg cttaacaaac     420
acatggattg cggtggaaaa cggtgctgct caggcgcagc tgtattcact ctttctgga      480 cttgtgtcag gattatgcgg gagcatatct gctttgtacg caacgct                  527

<210> SEQ ID NO 10
<211> LENGTH: 264
<212> TYPE: DNA
<213> ORGANISM: Infectious laryngotracheitis virus

<400> SEQUENCE: 10
tgactattac aatgacatgc ccgccgtgat cccggtggag gagactacta aaagttctaa      60
tgccgtctcc atgcccatat tcgcggcgtt cgtagcctgc gcggtcgcgc tcgtggggct     120
```

```
actggtttgg agcatcgtaa aatgcgcgcg tagctaatcg agcctagaat aggtggtttc    180
ttcctacatg ccacgcctca cgctcataat ataaatcaca tggaatagca taccaatgcc    240
tattcattgg gacgttcgaa aagc                                           264
```

<210> SEQ ID NO 11
<211> LENGTH: 360
<212> TYPE: DNA
<213> ORGANISM: Human cytomegalovirus

<400> SEQUENCE: 11

```
cgcgccaggt caattccctg gcattatgcc cagtacatga ccttatggga ctttcctact     60
tggcagtaca tctacgtatt agtcatcgct attaccatgg tgatgcggtt ttggcagtac    120
atcaatgggc gtggatagcg gtttgactca cggggatttc caagtctcca ccccattgac    180
gtcaatggga gtttgttttg caccaaaat caacgggact ttccaaaatg tcgtaacaac     240
tccgccccat tgacgcaaat gggcggtagc gtgtacggtg gaggtctat ataagcagag     300 ctcgtttagt gaaccgtcag atcgcctgga gacgccatcc acgctgtttt gacctccata    360
```

<210> SEQ ID NO 12
<211> LENGTH: 1191
<212> TYPE: DNA
<213> ORGANISM: Human cytomegalovirus

<400> SEQUENCE: 12

```
gtgaataata aaatgtgtgt ttgtccgaaa tacgcgtttg agatttctgt cccgactaaa     60
ttcatgtcgc gcgatagtgg tgtttatcgc cgatagagat ggcgatattg gaaaaatcga    120
tatttgaaaa tatggcatat tgaaaatgtc gccgatgtga gtttctgtgt aactgatatc    180
gccatttttc caaaagttga ttttttgggca tacgcgatat ctggcgatac gcttatatcg    240
tttacggggg atggcgatag acgccttttgg tgacttgggc gattctgtgt gtcgcaaata    300
tcgcagtttc gatataggtg acagacgata tgaggctata tcgccgatag aggcgacatc    360
aagctggcac atggccaatg catatcgatc tatacattga atcaatattg gccattagcc    420
atattattca ttggttatat agcataaatc aatattggct attggccatt gcatacgttg    480
tatccatatc ataatatgta catttatatt ggctcatgtc caacattacc gccatgttga    540
cattgattat tgactagtta ttaatagtaa tcaattacgg ggtcattagt tcatagccca    600
tatatggagt tccgcgttac ataacttacg gtaaatggcc cgcctggctg accgcccaac    660
gacccccgcc cattgacgtc aataatgacg tatgttccca tagtaacgcc aatagggact    720
ttccattgac gtcaatgggt ggagtattta cggtaaactg cccacttggc agtacatcaa    780
gtgtatcata tgccaagtac gccccctatt gacgtcaatg acggtaaatg gcccgcctgg    840
cattatgccc agtacatgac cttatgggac tttcctactt ggcagtacat ctacgtatta    900
gtcatcgcta ttaccatggt gatgcggttt tggcagtaca tcaatgggcg tggatagcgg    960
tttgactcac ggggatttcc aagtctccac cccattgacg tcaatgggag tttgttttgg   1020
caccaaaatc aacgggactt tccaaaatgt cgtaacaact ccgccccatt gacgcaaatg    1080 gcggtaggc gtgtacggtg gaggtctat ataagcagag ctcgtttagt gaaccgtcag     1140
atcgcctgga gacgccatcc acgctgtttt gacctccata gaagacaccg g            1191
```

<210> SEQ ID NO 13
<211> LENGTH: 281
<212> TYPE: DNA
<213> ORGANISM: Artificial Sequence

```
<220> FEATURE:
<223> OTHER INFORMATION: Synthetic sequence

<400> SEQUENCE: 13
ggaattctag atcccacgtc actattgtat actctatatt atactctatg ttatactctg      60
taatcctact caataaacgt gtcacgcctg tgaaaccgta ctaagtctcc cgtgtcttct     120
tatcaccatc aggtgacatc ctcgcccagg ctgtcaatca tgccggtatc gattccagta    180
gcaccggccc cacgctgaca acccactctt gcagcgttag cagcgcccct cttaacaagc    240 cgaccccccac cagcgtcgcg gttactaaca ctcctctccc c                        281

<210> SEQ ID NO 14
<211> LENGTH: 523
<212> TYPE: DNA
<213> ORGANISM: herpes simplex virus

<400> SEQUENCE: 14
gggagatggg ggaggctaac tgaaacacgg aaggagacaa taccggaagg aacccgcgct      60
atgacggcaa taaaagaca gaataaaacg cacgggtgtt gggtcgtttg ttcataaacg     120
cggggttcgg tcccagggct ggcactctgt cgatacccca ccgagacccc attgggacca    180
atacgcccgc gtttcttcct tttccccacc ccaaccccca agttcgggtg aaggcccagg    240
gctcgcagcc aacgtcgggg cggcaagccc tgccatagcc acgggccccg tgggttaggg    300
acggggtccc ccatggggaa tggtttatgg ttcgtggggg ttattatttt gggcgttgcg    360
tggggtcagg tccacgactg gactgagcag acagacccat ggttttttga tggcctgggc    420
atggaccgca tgtactggcg cgacacgaac accgggcgtc tgtggctgcc aaacaccccc    480 gaccccaaa aaccaccgcg cggatttctg gcgccgccgg acg                       523

<210> SEQ ID NO 15
<211> LENGTH: 3593
<212> TYPE: DNA
<213> ORGANISM: Artificial Sequence
<220> FEATURE:
<223> OTHER INFORMATION: Expression cassette insert

<400> SEQUENCE: 15
taattaaccc gggaagcttg catgcctgca gtgaataata aaatgtgtgt ttgtccgaaa      60
tacgcgtttg agatttctgt cccgactaaa ttcatgtcgc gcgatagtgg tgtttatcgc    120
cgatagagat ggcgatattg gaaaaatcga tatttgaaaa tatggcatat tgaaaatgtc    180
gccgatgtga gtttctgtgt aactgatatc gccatttttc caaaagttga tttttgggca    240
tacgcgatat ctggcgatac gcttatatcg tttacgggg atggcgatag acgcctttgg    300
tgacttgggc gattctgtgt gtcgcaaata tcgcagtttc gatataggtg acagacgata    360
tgaggctata tcgccgatag aggcgacatc aagctggcac atggccaatg catatcgatc    420
tatacattga atcaatattg gccattagcc atattattca ttggttatat agcataaatc    480
aatattggct attggccatt gcatacgttg tatccatatc ataatatgta catttatatt    540
ggctcatgtc caacattacc gccatgttga cattgattat tgactagtta ttaatagtaa    600
tcaattacgg ggtcattagt tcatagccca tatatggagt tccgcgttac ataacttacg    660
gtaaatggcc cgcctggctg accgcccaac gacccccgcc cattgacgtc aataatgacg    720
tatgttccca tagtaacgcc aatagggact ttccattgac gtcaatgggt ggagtattta    780
cggtaaactg cccacttggc agtacatcaa gtgtatcata tgccaagtac gccccctatt    840
```

```
gacgtcaatg acggtaaatg gcccgcctgg cattatgccc agtacatgac cttatgggac    900
tttcctactt ggcagtacat ctacgtatta gtcatcgcta ttaccatggt gatgcggttt    960
tggcagtaca tcaatgggcg tggatagcgg tttgactcac ggggatttcc aagtctccac   1020
cccattgacg tcaatgggag tttgttttgg caccaaaatc aacgggactt tccaaaatgt   1080
cgtaacaact ccgccccatt gacgcaaatg ggcggtaggc gtgtacggtg ggaggtctat   1140
ataagcagag ctcgtttagt gaaccgtcag atcgcctgga cgcatcc acgctgtttt      1200
gacctccata aagacaccg ggaccatgga tcgatcccgg ttggcgccct ccaggtgcag    1260
gatgggctcc agaccttcta ccaagaaccc agcacctatg atgctgacta tccgggtcgc   1320
gctggtactg agttgcatct gtccggcaaa ctccattgat ggcaggcctc ttgcagctgc   1380
aggaattgtg gttacaggag acaaagcagt caacatatac acctcatccc agacaggatc   1440
aatcatagtt aagctcctcc cgaatctgcc aaaggataag gaggcatgtg cgaaagcccc   1500
cttggatgca tacaacagga cattgaccac tttgctcacc ccccttggtg actctatccg   1560
taggatacaa gagtctgtga ctacatctgg aggggggaga caggggcgcc ttataggcgc   1620
cattattggc ggtgtggctc ttggggttgc aactgccgca caaataacag cggccgcagc   1680
tctgataca gccaaacaaa atgctgccaa catcctccga cttaaagaga gcattgccgc    1740
aaccaatgag gctgtgcatg aggtcactga cggattatcg caactagcag tggcagttgg   1800
gaagatgcag cagttcgtta atgaccaatt taataaaaca gctcaggaat tagactgcat   1860
caaaattgca cagcaagttg gtgtagagct caacctgtac ctaaccgaat cgactacagt   1920
attcggacca caaatcactt cacctgcctt aaacaagctg actattcagg cactttacaa   1980
tctagctggt gggaatatgg attacttatt gactaagtta ggtataggga caatcaact    2040
cagctcatta atcggtagcg gcttaatcac cggtaaccct attctatacg actcacagac   2100
tcaactcttg ggtatacagg taactctacc ttcagtcggg aacctaaata atatgcgtgc   2160
cacctacttg gaaaccttat ccgtaagcac aaccagggga tttgcctcgg cacttgtccc   2220
aaaagtggtg acacgggtcg gttctgtgat agaagaactt gacacctcat actgtataga   2280
aactgactta gatttatatt gtacaagaat agtaacgttc cctatgtccc ctggtatta    2340
ctcctgcttg agcggcaata atcggcctg tatgtactca aagaccgaag gcgcacttac    2400
tacaccatat atgactatca aaggctcagt catcgctaac tgcaagatga aacatgtag    2460
atgtgtaaac cccccgggta tcatatcgca aaactatgga gaagccgtgt ctctaataga   2520
taaacaatca tgcaatgttt tatccttagg cgggataact ttaaggctca gtggggaatt   2580
cgatgtaact tatcagaaga atatctcaat acaagattct caagtaataa taacaggcaa   2640
tcttgatatc tcaactgagc ttgggaatgt caacaactcg atcagtaatg ccttgaataa   2700
gttagaggaa agcaacagaa aactagacaa agtcaatgtc aaactgacca gcacatctgc   2760
tctcattacc tatatcgttt tgactatcat atctcttgtt tttggtatac ttagcctgat   2820
tctagcatgc tacctaatgt acaagcaaaa ggcgcaacaa aagaccttat tatggcttgg   2880
gaataatacc ctagatcaga tgagagccac tacaaaaatg tgaacacaga tgaggaacga   2940
aggtttccct aatagtaatt tgtgtgaaag ttctggtagt ctgtcagttc ggagagttaa   3000
gaaaaaaaaa aaaccccccc cccccccccc cccccccct gggtacgatc ctctagagtc    3060
gggagatggg ggaggctaac tgaaacacgg aaggagacaa taccggaagg aacccgcgct   3120
atgacgcaa taaaaagaca gaataaaacg cacgggtgtt gggtcgtttg ttcataaacg    3180
cggggttcgg tcccagggct ggcactctgt cgataccca ccgagacccc attgggacca    3240
```

```
atacgcccgc gtttcttcct tttccccacc ccaaccccca agttcgggtg aaggcccagg    3300
gctcgcagcc aacgtcgggg cggcaagccc tgccatagcc acgggccccg tgggttaggg    3360
acggggtccc ccatggggaa tggtttatgg ttcgtggggg ttattatttt gggcgttgcg    3420
tggggtcagg tccacgactg gactgagcag acagacccat ggttttgga tggcctgggc     3480 atggaccgca tgtactggcg cgacacgaac accgggcgtc tgtggctgcc aaacaccccc    3540
gacccccaaa aaccaccgcg cggatttctg gcgccgccgg acgtcgactt aat           3593
```

<210> SEQ ID NO 16
<211> LENGTH: 3569
<212> TYPE: DNA
<213> ORGANISM: Artificial Sequence
<220> FEATURE:
<223> OTHER INFORMATION: Expression cassette insert

<400> SEQUENCE: 16

```
gtcgacggca gagtcgcaga cgcccctatt ggacgtcaaa attgtagagg tgaagttttc      60
aaacgatggc gaagtaacgg cgacttgcgt ttccaccgtc aaatctccct atagggtaga    120
aactaattgg aaagtagacc tcgtagatgt aatggatgaa atttctggga acagtcccgc    180
cggggttttt aacagtaatg agaaatggca gaaacagctg tactacagag taaccgatgg    240
aagaacatcg gtccagctaa tgtgcctgtc gtgcacgagc cattctccgg aaccttactg    300
tcttttcgac acgtctctta tagcgaggga aaaagatatc cgccagagt tatactttac     360 ctctgatccg caaacggcat actgcacaat aactctgccg tccggcgttg ttccgagatt    420
cgaatggagc cttaataatg tttcactgcc ggaatatttg acggccacga ccgttgtttc    480
gcataccgct ggccaaagta cagtgtggaa gagcagcgcg agagcaggcg aggcgtggat    540
ttctggccgg ggaggcaata tacgaatg caccgtcctc atctcagacg gcactcgcgt      600
tactacgcga aggagaggt gcttaacaaa cacatggatt gcggtggaaa acggtgctgc     660
tcaggcgcag ctgtattcac tcttttctgg acttgtgtca ggattatgcg ggagcatatc    720
tgctttgtac gcaacgctat ggaccgccat ttatttttga ggaatgcttt ttggactatc    780
gtactgcttt cttccttcgc tagccagagc accgccgccg tcacgtacga ctacatttta    840
ggccgtcgcg cgctcgacgc gctaaccata ccggcggttg gcccgtataa cagataccctc   900 actagggtat caagaggctg cgacgttgtc gagctcaacc cgatttctaa cgtgacgac     960 atgatatcgg cggccaaaga aaaagagaag gggggcccctt tcgaggcctc cgtcgtctgg   1020
ttctacgtga ttaagggcga cgacggcgag acaagtact gtccaatcta tagaaaagag    1080
tacagggaat gtggcgacgt acaactgcta tctgaatgcg ccgttcaatc tgcacagatg    1140
tgggcagtgg actatgttcc tagcacccct gtatcgcgaa atggcgcggg actgactata    1200
ttctccccca ctgctgcgct ctctggccaa tacttgctga ccctgaaaat cgggagattt    1260
gcgcaaacag ctctcgtaac tctagaagtt aacgatcgct gttaaagat cgggtcgcag     1320 cttaactttt taccgtcgaa atgctggaca acagaacagt atcagactgg atttcaaggc    1380
gaacaccttt atccgatcgc agacaccaat acacgacacg cggacgacgt atatcgggga    1440
tacgaagata ttctgcagcg ctggaataat ttgctgagga aaaagaatcc tagcgcgcca    1500
gaccctcgtc cagatagcgt cccgcaagaa attcccgctg taaccaagaa agcggaaggg    1560 cgcacccccgg acgcagaaag cagcgaaaag aaggcccctc cagaagactc ggaggacgac    1620
atgcaggcag aggcttctgg agaaaatcct gccgccctcc ccgaagacga cgaagtcccc    1680
gaggacaccg agcacgatga tccaaactcg gatcctgact attacaatga catgcccgcc    1740
```

```
gtgatcccgg tggaggagac tactaaaagt tctaatgccg tctccatgcc catattcgcg   1800
gcgttcgtag cctgcgcggt cgcgctcgtg gggctactgg tttggagcat cgtaaaatgc   1860
gcgcgtagct aatcgagcct agaataggtg gtttcttcct acatgccacg cctcacgctc   1920
ataatataaa tcacatggaa tagcatacca atgcctattc attgggacgt tcgaaaagca   1980
tggcatcgct acttggaact ctggctctcc ttgccgcgac gctcgcaccc ttcggcgcga   2040
tgggaatcgt gatcactgga atcacgtct ccgccaggat tgacgacgat cacatcgtga   2100
tcgtcgcgcc tcgccccgaa gctacaattc aactgcagct attttcatg cctggccaga   2160 gaccccacaa accctactca ggaaccgtcc gcgtcgcgtt tcggtctgat ataacaaacc   2220
agtgctacca ggaacttagc gaggagcgct ttgaaaattg cactcatcga tcgtcttctg   2280
tttttgtcgg ctgtaaagtg accgagtaca cgttctccgc ctcgaacaga ctaaccggac   2340
ctccacaccc gtttaagctc actatacgaa atcctcgtcc gaacgacagc gggatgttct   2400
acgtaattgt tcggctagac gacaccaaag aacccattga cgtcttcgcg atccaactat   2460
cggtgtatca attcgcgaac accgccgcga ctcgcggact ctattccaag gcttcgtgtc   2520
gcaccttcgg attacctacc gtccaacttg aggcctatct caggaccgag gaaagttggc   2580
gcaactggca gcgtacgtt gccacggagg ccacgacgac cagcgccgag cgacaaccc   2640 cgacgcccgt cactgcaacc agcgcctccg aacttgaagc ggaacacttt accttcctt   2700 ggctagaaaa tggcgtggat cattacgaac cgacacccgc aaacgaaaat tcaaacgtta   2760
ctgtccgtct cgggacaatg agccctacgc taattggggt aaccgtggct gccgtcgtga   2820
gcgcaacgat cggcctcgtc attgtaattt ccatcgtcac cagaaacatg tgcaccccgc   2880
accgaaaatt agacacggtc tcgcaagacg acgaagaacg ttcccaaact agaagggaat   2940
cgcgaaaatt tggaccccatg gttgcgtgcg aaataaacaa gggggctgac caggatagtg   3000
aacttgtgga actggttgcg attgttaacc cgtctgcgct aagctcgccc gactcaataa   3060
aaatgtgatt aagtctgaat gtggctctcc aatcatttcg attctctaat ctcccaatcc   3120
tctcaaaagg ggcagtatcg gacacggact gggaggggcg tacacgatag ttatatggta   3180
cagcagaggc ctctgaacac ttaggaggag aattcagccg gggagagccc ctgttgagta   3240
ggcttgggag catattgcag gatgaacatg ttagtgatag ttctcgcctc ttgtcttgcg   3300
cgcctaactt ttgcgacgcg acacgtcctc ttttggaag gcactcaggc tgtcctcggg   3360
gaagatgatc ccagaaacgt tccggaaggg actgtaatca aatggacaaa agtcctgcgg   3420
aacgcgtgca agatgaaggc ggccgatgtc tgctcttcgc ctaactattg ctttcatgat   3480
ttaatttacg acggaggaaa gaaagactgc ccgcccgcgg gacccctgtc tgcaaacctg   3540
gtaattttac taaagcgcgg cgaaagctt                                     3569
```

<210> SEQ ID NO 17
<211> LENGTH: 5921
<212> TYPE: DNA
<213> ORGANISM: Artificial Sequence
<220> FEATURE:
<223> OTHER INFORMATION: Expression cassette insert

<400> SEQUENCE: 17

```
gtcgacggca gagtcgcaga cgcccctatt ggacgtcaaa attgtagagg tgaagttttc     60
aaacgatggc gaagtaacgg cgacttgcgt ttccaccgtc aaatctccct atagggtaga    120
aactaattgg aaagtagacc tcgtagatgt aatggatgaa atttctggga acagtcccgc    180
cggggttttt aacagtaatg agaaatggca gaaacagctg tactacagag taaccgatgg    240
```

-continued

```
aagaacatcg gtccagctaa tgtgcctgtc gtgcacgagc cattctccgg aaccttactg      300
tcttttcgac acgtctctta tagcgaggga aaaagatatc gcgccagagt tatactttac      360
ctctgatccg caaacggcat actgcacaat aactctgccg tccggcgttg ttccgagatt      420
cgaatggagc cttaataatg tttcactgcc ggaatatttg acggccacga ccgttgtttc      480
gcataccgct ggccaaagta cagtgtggaa gagcagcgcg agagcaggcg aggcgtggat      540
ttctggccgg ggaggcaata tatacgaatg caccgtcctc atctcagacg gcactcgcgt      600
tactacgcga aaggagaggt gcttaacaaa cacatggatt gcggtggaaa acggtgctgc      660
tcaggcgcag ctgtattcac tcttttctgg acttgtgtca ggattatgcg ggagcatatc      720
tgctttgtac gcaacgctat ggaccgccat ttattttga ggaatgcttt ttggactatc      780
gtactgcttt cttccttcgc tagccagagc accgccgccg tcacgtacga ctacatttta      840
ggccgtcgcg cgctcgacgc gctaaccata ccggcggttg gcccgtataa cagataccctc      900 actagggtat caagaggctg cgacgttgtc gagctcaacc cgatttctaa cgtggacgac      960
atgatatcgg cggccaaaga aaagagaag ggggccctt tcgaggcctc cgtcgtctgg      1020
ttctacgtga ttaagggcga cgacggcgag gacaagtact gtccaatcta tagaaaagag      1080
tacagggaat gtgcgacgt acaactgcta tctgaatgcg ccgttcaatc tgcacagatg      1140
tgggcagtgg actatgttcc tagcacccctt gtatcgcgaa atggcgcggg actgactata      1200
ttctccccca ctgctgcgct ctctggccaa tacttgctga ccctgaaaat cgggagattt      1260
gcgcaaacag ctctcgtaac tctagaagtt aacgatcgct gtttaaagat cgggtcgcag      1320
cttaactttt taccgtcgaa atgctggaca acagaacagt atcagactgg atttcaaggc      1380
gaacaccttt atccgatcgc agacaccaat acacgacacg cggacgacgt atatcgggga      1440
tacgaagata ttctgcagcg ctggaataat ttgctgagga aaaagaatcc tagcgcgcca      1500
gaccctcgtc cagatagcgt cccgcaagaa attcccgctg taaccaagaa agcggaaggg      1560
cgcaccccgg acgcagaaag cagcgaaaag aaggcccctc cagaagactc ggaggacgac      1620
atgcaggcag aggcttctgg agaaaatcct gccgccctcc ccgaagacga cgaagtcccc      1680
gaggacaccg agcacgatga tccaaactcg gatcctgact attacaatga catgcccgcc      1740
gtgatcccgg tggaggagac tactaaaagt tctaatgccg tctccatgcc catattcgcg      1800
gcgttcgtag cctgcgcggt cgcgctcgtg gggctactgg tttggagcat cgtaaaatgc      1860
gcgcgtagct aatcgagcct agaataggtg gtttcttcct acatgccacg cctcacgctc      1920
ataatataaa tcacatggaa tagcatacca atgcctattc attgggacgt tcgaaaagca      1980
tggcatcgct acttggaact ctggctctcc ttgccgcgac gctcgcaccc ttcggcgcga      2040
tgggaatcgt gatcactgga aatcacgtct ccgccaggat tgacgacgat cacatcgtga      2100
tcgtcgcgcc tcgccccgaa gctacaattc aactgcagct attttttcatg cctggccaga      2160 gacccacaa accctactca ggaaccgtcc gcgtcgcgtt tcggtctgat ataacaaacc      2220
agtgctacca ggaacttagc gaggagcgct ttgaaaattg cactcatcga tcgtcttctg      2280
tttttgtcgg ctgtaaagtg accgagtaca cgttctccgc ctcgaacaga ctaaccggac      2340
ctccacaccc gtttaagctc actatacgaa atcctcgtcc gaacgacagc gggatgttct      2400
acgtaattgt tcggctagac gacaccaaag aacccattga cgtcttcgcg atccaactat      2460
cggtgtatca attcgcgaac accgccgcga ctcgcggact ctattccaag gcttcgtgtc      2520
gcaccttcgg attacctacc gtccaacttg aggcctatct caggaccgag gaaagttggc      2580
gcaactggca agcgtacgtt gccacggagg ccacgacgac cagcgccgag gcgacaaccc      2640
```

-continued

```
cgacgcccgt cactgcaacc agcgcctccg aacttgaagc ggaacacttt acctttccct    2700
ggctagaaaa tggcgtggat cattacgaac cgacacccgc aaacgaaaat tcaaacgtta    2760
ctgtccgtct cgggacaatg agccctacgc taattggggt aaccgtggct gccgtcgtga    2820
gcgcaacgat cggcctcgtc attgtaattt ccatcgtcac cagaaacatg tgcaccccgc    2880
accgaaaatt agacacggtc tcgcaagacg acgaagaacg ttcccaaact agaagggaat    2940
cgcgaaaatt tggacccatg gttgcgtgcg aaataaacaa gggggctgac caggatagtg    3000
aacttgtgga actggttgcg attgttaacc cgtctgcgct aagctcgccc gactcaataa    3060
aaatgtgatt aagtctgaat gtggctctcc aatcatttcg attctctaat ctcccaatcc    3120
tctcaaaagg ggcagtatcg gacacggact ggggaggggcg tacacgatag ttatatggta    3180
cagcagaggc ctctgaacac ttaggaggag aattcagccg gggagagccc ctgttgagta    3240
ggcttgggag catattgcag gatgaacatg ttagtgatag ttctcgcctc ttgtcttgcg    3300
cgcctaactt ttgcgacgcg acacgtcctc tttttggaag gcactcaggc tgtcctcggg    3360
gaagatgatc ccagaaacgt tccggaaggg actgtaatca aatggacaaa agtcctgcgg    3420
aacgcgtgca agatgaaggc ggccgatgtc tgctcttcgc ctaactattg ctttcatgat    3480
ttaatttacg acggaggaaa gaaagactgc ccgcccgcgg gaccccctgtc tgcaaacctg    3540
gtaattttac taaagcgcgg cgaaagcttc gcgccaggtc aattccctgg cattatgccc    3600
agtacatgac cttatgggac tttcctactt ggcagtacat ctacgtatta gtcatcgcta    3660
ttaccatggt gatgcggttt tggcagtaca tcaatgggcg tggatagcgg tttgactcac    3720
ggggattttcc aagtctccac cccattgacg tcaatgggga tttgtttttgg caccaaaatc    3780
aacgggactt tccaaaatgt cgtaacaact ccgccccatt gacgcaaatg ggcggtagcg    3840
tgtacggtgg gaggtctata taagcagagc tcgtttagtg aaccgtcaga tcgcctggag    3900
acgccatcca cgctgttttg acctccatag aagacaccgg ttgcgccgcc accatgggcc    3960
ccagaccttc taccaagaac ccagtaccta tgatgctgac tgtccgagtc gcgctggtac    4020
tgagttgcat ctgtccggca aactccattg atggcaggcc tcttgcggct gcaggaattg    4080
tggttacagg agacaaagcc gtcaacatat acacctcatc ccagacagga tcaatcatag    4140
ttaagctcct cccgaatctg cccaaggata aggaggcatg tgcgaaagcc cccttggatg    4200
catacaacag gacattgacc actttgctca ccccccttgg tgactctatc cgtaggatac    4260
aagagtctgt gactacatct ggaggggggga gacaggggcg ccttataggc gccattattg    4320
gcggtgtggc tcttggggtt gcaactgccg cacaaataac agcggccgca gctctgatac    4380
aagccaaaca aaatgctgcc aacatcctcc gacttaaaga gagcattgcc gcaaccaatg    4440
aggctgtgca tgaggtcact gacgattat cgcaactagc agtggcagtt gggaagatgc    4500
agcagtttgt taatgaccaa tttaataaaa cagctcagga attagactgc atcaaaattg    4560
cacagcaagt tggtgtagag ctcaacctgt acctaaccga attgactaca gtattcggac    4620
cacaaatcac ttcacctgct ttaaacaagc tgactattca ggcactttac aatctagctg    4680
gtggaaatat ggattactta ttgactaagt taggtgtagg gaacaatcaa ctcagctcat    4740
taatcggtag cggcttaatc accggtaacc ctattctata cgactcacag actcaactct    4800
tgggtataca ggtaactcta ccttcagtcg ggaagctaaa taatatgcgt gccacctact    4860
tggaaacctt atccgtaagc acaaccaggg gatttgcctc ggcacttgtc ccaaagtgg    4920
tgacacaggt cggttctgtg atagaagaac ttgacacctc atactgtata gaaactgact    4980
tacatttata ttgtacaaga atagtaacgt tccctatgtc ccctggtatt tattcctgct    5040
```

-continued

```
tgagcggcaa tacgtcggcc tgtatgtact caaagaccga aggcgcactt actacaccat    5100
acatgactat caaaggttca gtcatcgcca actgcaagat gacaacatgt agatgtgtaa    5160
acccccgggg tatcatatcg caaaactatg gagaagccgt gtctctaata gataaacaat    5220
catgcaatgt tttatcctta ggcgggataa ctttaaggct cagtggggaa ttcgatgtaa    5280
cttatcagaa gaatatctca atacaagatt ctcaagtaat aataacaggc aatcttgata    5340
tctcaactga gcttgggaat gtcaacaact cgatcagtaa tgctttgaat aagttagagg    5400
aaagcaacag aaaactagac aaagtcaatg tcaaactgac tagcacatct gctctcatta    5460
cctatatcgt gttgactatc atatctcttg tttttggtat acttagcctg attctagcat    5520
gctacctaat gtacaagcaa aaggcgcaac aaaagacctt attatggctt gggaataata    5580
ctctagatca gatgagagcc actacaaaaa tgtgaggatc tctcgaggaa ttctagatcc    5640
cacgtcacta ttgtatactc tatattatac tctatgttat actctgtaat cctactcaat    5700
aaacgtgtca cgcctgtgaa accgtactaa gtctcccgtg tcttcttatc accatcaggt    5760
gacatcctcg cccaggctgt caatcatgcc ggtatcgatt ccagtagcac cggcccacg    5820 ctgacaaccc actcttgcag cgttagcagc gccctctta acaagccgac ccccaccagc    5880
gtcgcggtta ctaacactcc tctccccgac ctgcaactag t                         5921
```

RECOMBINANT NON-PATHOGENIC MAREK'S DISEASE VIRUS CONSTRUCTS ENCODING INFECTIOUS LARYNGOTRACHEITIS VIRUS AND NEWCASTLE DISEASE VIRUS ANTIGENS

CROSS-REFERENCE TO RELATED APPLICATIONS

This application claims priority under 35 U.S.C. §119(e) of provisional application U.S. Ser. No. 61/549,844 filed Oct. 21, 2011, the contents of which are hereby incorporated by reference in their entireties.

FIELD OF THE INVENTION

The present invention relates to novel recombinant multivalent non-pathogenic Marek's Disease virus constructs encoding and expressing Infectious Laryngotracheitis Virus and Newcastle Disease virus protein antigens, and methods of their use in poultry vaccines.

BACKGROUND OF THE INVENTION

Pathogenic poultry viruses are not only debilitating to chickens, but they also are costly to chicken breeders because most of the resulting diseases are contagious and the poultry industry relies heavily on confined, large-scale breeding facilities. Vaccinating young chicks is often the only viable means to combat these viruses. Although attenuated or killed poultry viral vaccines remain important in the market place, in recent years significant resources have been expended on developing vaccines containing recombinant viral constructs which express pathogenic viral protein antigens. Furthermore, substantial efforts have been made to construct stable and efficacious multivalent recombinant non-pathogenic Marek's Disease virus ($rMDV_{np}$) vectors that express foreign genes from multiple viral pathogens. Such multivalent vaccines would serve to minimize the number of injections given to the chicks and thereby, reduce discomfort and stress on the vaccinated chick, as well as significantly reduce costs in labor and materials. Vaccinating with such single multivalent constructs also would be preferable to alternative multivalent $rMDV_{np}$ vaccines that contain multiple recombinant monovalent $rMDV_{np}$ constructs, because these alternative vaccines have, at least to date, resulted in protection against only a single viral pathogen. The failure of such alternative vaccines is presumably due to one of the monovalent $rMDV_{np}$ constructs overgrowing the other monovalent $rMDV_{np}$ constructs thereby, preventing these other monovalent $rMDV_{np}$ constructs from inducing a significant immune response. In any case, despite substantial efforts in the past to construct stable and efficacious multivalent recombinant $rMDV_{np}$ vectors that express foreign genes from multiple viral pathogens heretofore, such efforts have proved unsuccessful.

One poultry virus disease that can be controlled through vaccination is Marek's disease. Marek's disease is a pathogenic disease that adversely affects chickens, worldwide. Marek's disease occurs predominantly in young chickens between 2 and 5 months of age. Clinical signs include: progressive paralysis of one or more of the extremities, incoordination due to paralysis of legs, drooping of the limb due to wing involvement, and a lowered head position due to involvement of the neck muscles. In acute cases, severe depression may result. Bursal and thymic atrophy may also develop.

The etiological agent for Marek's disease is Marek's disease virus serotype 1 (MDV1), a cell-associated virus having a double-standed DNA genome. MDV1 is a lymphotropic avian alphaherpesvirus that both: (i) infects B cells, which can result in cytolysis, and (ii) latently infects T cells, which can induce T-cell lymphoma. Closely related to the virulent MDV1 strain, Marek's disease virus serotype 2 (MDV2), previously known as Gallid herpes virus 3, is a naturally attenuated MDV strain that has been shown to have little to no pathogenicity in chickens [Petherbridge et al., *J. Virological Methods* 158:11-17 (2009)]. SB-1 is a specific MDV2 strain that has been shown to be useful in vaccines against MDV1 [see e.g., Murthy and Calnek, Infection and Immunity 26(2) 547-553 (1979)].

Another closely related alphaherpesvirus, Marek's disease virus serotype 3 (MDV3), more widely known as herpesvirus of turkeys (HVT), is a nonpathogenic virus of domestic turkeys [see e.g., Kingham et al., *J. of General Virology* 82:1123-1135 (2001)]. Two commonly used strains of HVT are the PB1 strain and the FC126 strain. Whereas, HVT is also non-pathogenic in chickens, it does induce a long-lasting protective immune response in chickens against MDV1. Accordingly, HVT has been used in poultry vaccines against virulent MDV1 for many years, generally in combination with SB-1, which is more viraemic than HVT, but considered less safe. Alternatively, when flocks are challenged with particularly virulent MDV1 strains, HVT can be combined with the Rispen's vaccine. The Rispen's vaccine is an isolate that originated from a mildly virulent MDV1 strain that was subsequently further weakened by cell passaging. The Rispen's strain however, retains some virulence towards highly susceptible lines of chickens.

The sequence of the complete genome of HVT has been disclosed [Afonso et al., *J. Virology* 75(2):971-978 (2001)], and as most alphaherpesviruses, HVT possesses a significant number of potential nonessential insertion sites [see e.g., U.S. Pat. Nos. 5,187,087; 5,830,745; 5,834,305; 5,853,733; 5,928, 648; 5,961,982; 6,121,043; 6,299,882 B1]. HVT also has been shown to be amenable to genetic modification and thus, has been used as a recombinant vector for many years [WO 87/04463]. Accordingly, recombinant HVT vectors have been reported to express foreign genes that encode antigens from e.g., Newcastle Disease Virus (NDV), [Sondermeijer et al., *Vaccine*, 11:349-358 (1993); Reddy et al., *Vaccine*, 14:469-477 (1996)], Infectious Bursal Disease Virus (IBDV), [Darteil et al., *Virology*, 211:481-490 (1995); Tsukamoto et al., *J. of Virology* 76(11):5637-5645 (2002)], and Infectious Laryngotracheitis Virus (ILTV) [Johnson et al., *Avian Disease*, 54(4):1251-1259 (2010); WO 92/03554; U.S. Pat. No. 6,875,856]. The entire genomic sequence of MDV2 is also known [see, GenBank acc. nr: AB049735.1, and Petherbridge et al., supra]. The genomic organization of the MDV2 is very similar to that of HVT, with the US region in particular, being identical to that of HVT [see, Kingham et al., supra].

In addition a recombinant chimeric virus, known as the novel avian herpesvirus (NAHV), has been constructed in which specific regions of the HVT genome have been replaced by the corresponding regions of the MDV1 genome. The NAHV also has been used to express foreign genes that encode antigens from other poultry viruses [U.S. Pat. Nos. 5,965,138; 6,913,751].

Like MDV, infectious laryngotracheitis virus (ILTV) is an alphaherpesvirus that adversely affects chickens, worldwide [Fuchs et al., *Veterinary Research* 38:261-279 (2007)]. ILTV causes acute respiratory disease in chickens, which is characterized by respiratory depression, gasping, and expectoration of bloody exudate. Viral replication is limited to cells of the respiratory tract, where in the trachea the infection gives rise to tissue erosion and hemorrhage.

Newcastle disease is another highly contagious and debilitating disease of chickens. The etiological agent for Newcastle disease is the Newcastle disease virus (NDV). NDV belongs to the order of the Mononegavirales and is in the family of Paramyxoviridae. Newcastle disease viruses have a non-segmented, negative sense, single-stranded RNA genome. NDV has been grouped into three distinct pathotypes according to their virulence. Infection of poultry by the non-pathogenic lentogenic strains of NDV is essentially asymptomatic. In direct contrast, the mesogenic (medium pathogenic) and velogenic (highly pathogenic) NDV strains cause extensive disease that can be fatal. Most types of NDV infect the respiratory system and/or the nervous system, and can result in gasping and torticollis.

Infectious bursal disease virus (IBDV), also called Gumboro disease virus, is the causative agent of infectious bursal disease. IBDV causes an acute, highly-contagious, viral infection of a chicken's lymphoid tissue, with its primary target being the bird's essential immunological organ: the bursa of Fabricius. The morbidity rate in susceptible flocks is high, with rapid weight loss and moderate to high mortality rates. Chicks that recover from the disease may have immune deficiencies because of destruction of (or parts of) the bursa of Fabricius. This makes them particularly vulnerable to secondary infections.

IBDV is a member of the Birnaviridae family. The viruses in this family have a genome consisting of two segments (A and B) of double-stranded RNA. Two serotypes of IBDV exist, serotype 1 and 2, which can be differentiated by virus neutralization (VN) tests. Serotype 1 viruses have been shown to be pathogenic to chickens, while serotype 2 viruses cause only sub-acute disease in turkeys. Historically, IBDV serotype 1 viruses consisted of only one type that is now known as "classic" IBD virus. More recently, so-called "variant" IBDV strains have emerged. Classic and variant strains of IBDV can be identified and distinguished by a virus neutralisation test using a panel of monoclonal antibodies, or by RT-PCR [Wu et al., *Avian Diseases*, 51:515-526(2007)]. Well-known classic IBDV strains include, D78, Faragher 52/70, and STC, whereas 89/03 is a well-known variant strain. Many live or inactivated IBDV vaccines are commercially available, e.g. a live vaccine such as NOBILIS® Gumboro D78 (MSD Animal Health).

As indicated above, because HVT can act as both an antigen that provides significant protection against Marek's Disease and as a recombinant vector, it is presently used as a platform vector for such multivalent vaccines as Innovax®-ILT (sold by Merck Animal Health), which protects against ILTV; and Innovax®-ND-SB (sold by Merck Animal Health) and Vectormune® HVT-NDV (sold by Ceva), both of which protect against NDV. Notably, however, heretofore, no multivalent vaccine comprising a recombinant HVT encoding antigens from more than one pathogen has been shown to be stable and efficacious, even though such vaccines had been suggested more than fifteen years ago [see e.g., U.S. Pat. No. 5,965,138]. Indeed, Innovax®-ILT contains the only recombinant HVT that comprises two foreign genes, i.e., ILTV gD and ILTV gI, which has proved to be safe, effective, and stable. However, these two foreign genes are from the same pathogen and moreover, they naturally overlap and need to be co-expressed in order to allow proper immunization against ILTV.

Accordingly, despite the clear advantages of stable, multivalent, recombinant $MDV_{np}$ constructs that can efficaciously express foreign antigens from two or more different pathogens, and the substantial efforts to design them, heretofore, none have been forthcoming. Therefore, there is a clear need to overcome the collective industry failure, by constructing novel, stable, recombinant $MDV_{np}$ vectors that can be used in multivalent vaccines as the sole active to protect against two or more different non-MDV1 poultry virus pathogens.

The citation of any reference herein should not be construed as an admission that such reference is available as "prior art" to the instant application.

SUMMARY OF THE INVENTION

Accordingly, the present invention provides a novel, stable, and efficacious multivalent recombinant nonpathogenic Marek's Disease virus ($rMDV_{np}$) for use as a vector to express foreign genes from multiple viral pathogens. In particular embodiments, the $rMDV_{np}$ is a recombinant herpesvirus of turkeys (rHVT). In alternative embodiments, the $rMDV_{np}$ is a recombinant Marek's disease virus serotype 2 (rMDV2). Ark $rMDV_{np}$, e.g., an rHVT or an rMDV2, can be used in vaccines against pathogenic poulty viruses.

In particular embodiments, an $rMDV_{np}$ comprises a first nucleic acid inserted in a first nonessential site in the $rMDV_{np}$ genome and a second nucleic acid inserted in a second nonessential site in the $rMDV_{np}$ genome. The first nucleic acid comprises both a nucleotide sequence that encodes an Infectious Laryngotracheitis Virus (ILTV) gD protein and a nucleotide sequence that encodes an Infectious Laryngotracheitis Virus (ILTV) gI protein. The second nucleic acid comprises a nucleotide sequence that encodes a Newcastle Disease Virus (NDV) F protein. In specific embodiments of this type, the first nucleic acid comprises the nucleotide sequence of SEQ ID NO: 16 and the second nucleic acid comprises the nucleotide sequence of SEQ ID NO: 15. In specific embodiments, the $rMDV_{np}$ is an rHVT. In alternative embodiments, the $rMDV_{np}$ is an rMDV2.

In certain embodiments, the first nonessential site of the $rMDV_{np}$ is the US2 site, while the second nonessential site is a nonessential site of the $rMDV_{np}$ other than the US2 site. In related embodiments, the first nonessential site of the $rMDV_{np}$ is the US2 site and the second nonessential site of the $rMDV_{np}$ is the UL7/8 site. In yet other embodiments, the first nonessential site of the $rMDV_{np}$ is the US2 site and the second nonessential site of the $rMDV_{np}$ is the US10 site. In still other embodiments, the first nonessential site of the $rMDV_{np}$ is the US2 site and the second nonessential site of the $rMDV_{np}$ is the UL 54.5 site. In specific embodiments, the $rMDV_{np}$ is an rHVT. In alternative embodiments, the $rMDV_{np}$ is an rMDV2.

In other embodiments, the first nonessential site and the second nonessential site of the $rMDV_{np}$ are the same. In specific embodiments of this type, the first nucleic acid and the second nucleic acid are actually constructed as part of the same DNA molecule, which is inserted into a nonessential site of the $rMDV_{np}$. Such a DNA molecule can be an expression cassette that encodes an Infectious Laryngotracheitis Virus (ILTV) gD protein, an Infectious Laryngotracheitis Virus (ILTV) gI protein, and a Newcastle Disease Virus (NDV) F protein. In particular embodiments of this type, the DNA molecule comprises the nucleotide sequence of SEQ ID NO: 17. In specific embodiments, the $rMDV_{np}$ is an rHVT. In alternative embodiments, the $rMDV_{np}$ is an rMDV2.

Accordingly, in particular embodiments, the first nonessential site and the second nonessential site of the $rMDV_{np}$ are the US2 site. In other embodiments, the first nonessential site and the second nonessential site of the $rMDV_{np}$ are the UL54.5 site. In yet other embodiments, the first nonessential site and the second nonessential site of the $rMDV_{np}$ are the UL7/8 site. In still other embodiments, the first nonessential site and the second nonessential site of the rMDV$_{np}$ are the US10 site. In specific embodiments, the rMDV$_{np}$ is an rHVT. In alternative embodiments, the rMDV$_{np}$ is an rMDV2.

The nucleotide sequences encoding the ILTV gD protein, the ILTV gI protein, and the NDV F protein can be operatively under the control of exogenous promoters, i.e., promoters that are not naturally found in the MDV$_{np}$. In certain embodiments, these three nucleotide sequences are operatively under the control of different promoters, i.e., the nucleotide sequence encoding the ILTV gD protein is operatively under the control of a first promoter, the nucleotide sequence encoding the ILTV gI protein is operatively under the control of a second promoter, and the nucleotide sequence encoding the NDV F protein is operatively under the control of a third promoter, with the first promoter, the second promoter, and the third promoter all being different. In particular embodiments, the promoter for the nucleotide sequence encoding the ILTV gD protein is the endogenous ILTV gD promoter. In certain embodiments, the promoter for the nucleotide sequence encoding the ILTV gI protein is the endogenous ILTV gI promoter. In particular embodiments of this type, the promoter for the nucleotide sequence encoding the ILTV gD protein is the endogenous ILTV gD promoter and the promoter for the nucleotide sequence encoding the ILTV gI protein is the endogenous ILTV gI promoter. In specific embodiments, the rMDV$_{np}$ is an rHVT. In alternative embodiments, the rMDV$_{np}$ is an rMDV2.

In certain embodiments, at least one of the promoters operably linked to a nucleotide sequence encoding the ILTV gD protein, the ILTV gI protein, or the NDV F protein is the human cytomegalovirus immediate early (hCMV IE) promoter. In particular embodiments of this type, the promoter for the nucleotide sequence encoding the NDV F protein is the hCMV IE promoter. In specific embodiments, at least one of the promoters operably linked to a nucleotide sequence encoding the ILTV gD protein, the ILTV gI protein or the NDV F protein is the pseudorabies virus (PRV) gpX promoter. In related embodiments, at least one of the promoters operably linked to a nucleotide sequence encoding the ILTV gD protein, the ILTV gI protein or the NDV F protein is the chicken beta-actin gene promoter. In specific embodiments, the promoter for the nucleotide sequence encoding the NDV F protein is the hCMV IE promoter, the promoter for the nucleotide sequence encoding the ILTV gD protein is the endogenous ILTV gD promoter, and the promoter for the nucleotide sequence encoding the ILTV gI protein is the endogenous ILTV gI promoter.

In certain embodiments, an rMDV$_{np}$ of the present invention that includes insertions of nucleotide sequences encoding the ILTV gD protein, the ILTV gI protein, and the NDV F protein also includes one or more exogenous transcription terminator sequences. In specific embodiments of this type, a transcription terminator sequence is downstream from the nucleotide sequence encoding the NDV F protein. In particular embodiments, the nucleotide sequences encoding the ILTV gD protein and the ILTV gI protein share one transcription terminator sequence and the nucleotide sequence encoding the NDV F protein has another. In particular embodiments, at least one of the transcription terminator sequences comprises a synthetic polyadenylation sequence. In related embodiments at least one of the transcription terminator sequences comprises a Herpes Simplex Virus thymidine kinase (HSV TK) polyadenylation sequence. In specific embodiments, the rMDV$_{np}$ is an rHVT. In alternative embodiments, the rMDV$_{np}$ is an rMDV2.

The present invention also provides a recombinant nucleic acid comprising in 5' to 3' direction in the following order (i) an Infectious Laryngotracheitis Virus (ILTV) gD promoter, (ii) a coding sequence for the ILTV gD protein, (iii) an ILTV gI promoter, (iv) a coding sequence for the ILTV gI protein, (v) a human cytomegalovirus immediate early (hCMV IE) promoter, (vi) a coding sequence for the NDV F protein, and (viii) a transcription terminator sequence. In a particular embodiment of this type, the recombinant nucleic acid comprises the nucleotide sequence of SEQ ID NO: 17.

The present invention further provides an rMDV$_{np}$ in which a recombinant nucleic acid of the present invention has been inserted into a nonessential insertion site of the rMDV$_{np}$. In certain embodiments of this type, the rMDV$_{np}$ includes an insert in a nonessential site that comprises a recombinant nucleic acid comprising in 5' to 3' direction in the following order (i) an Infectious Laryngotracheitis Virus (ILTV) gD promoter, (ii) a coding sequence for the ILTV gD protein, (iii) an ILTV gI promoter, (iv) a coding sequence for the ILTV gI protein, (v) a human cytomegalovirus immediate early (hCMV IE) promoter, (vi) a coding sequence for the NDV F protein, and (vii) a transcription terminator sequence. In specific embodiments, intervening nucleotide sequences, such as linkers, spacer sequences, and/or extraneous coding sequences, can also be included, see Example 1 below. In a particular embodiment, the rHVT comprises the nucleotide sequence of SEQ ID NO: 17 inserted into a nonessential site. In particular embodiments of these types, the nonessential site is the US2 site. In other such embodiments, the nonessential site is the UL54.5 site. In still other such embodiments, the nonessential site is the UL7/8 site. In yet other such embodiments, the nonessential site is the US10 site. In specific embodiments, the rMDV$_{np}$ is an rHVT. In alternative embodiments, the rMDV$_{np}$ is an rMDV2.

The present invention also provides methods of making an rMDV$_{np}$ of the present invention. In certain embodiments, a heterologous nucleic acid is constructed that comprises a nucleotide sequence that encodes an ILTV gD protein, a nucleotide sequence that encodes an ILTV gI protein, and a nucleotide sequence that encodes an NDV F protein. The heterologous nucleic acid is then inserted into a nonessential site of an rMDV$_{np}$ of the present invention. In certain embodiments, the heterologous nucleic acid is an expression cassette. In particular embodiments of this type, the expression cassette comprises the nucleotide sequence of SEQ ID NO: 17. In other embodiments, a first heterologous nucleic acid is constructed that comprises a nucleotide sequence that encodes an ILTV gD protein and a nucleotide sequence that encodes an ILTV gI protein; and a second heterologous nucleic acid is constructed that comprises a nucleotide sequence that encodes an NDV F protein. The first heterologous nucleic acid is inserted into a US2 site of an rMDV$_{np}$ and the second heterologous nucleic acid is inserted into an alternative nonessential site of the rMDV$_{np}$. In certain embodiments, such heterologous nucleic acids are expression cassettes. In particular embodiments of this type, the first heterologous nucleic acid comprises the nucleotide sequence of SEQ ID NO: 16, and the second heterologous nucleic acid comprises the nucleotide sequence of SEQ ID NO: 15. In specific embodiments, the method of making an rMDV$_{np}$ is a method of making an rHVT. In alternative embodiments, the method of making an rMDV$_{np}$ is a method of making an rMDV2.

The present invention further provides immunogenic compositions and/or vaccines that comprise any rMDV$_{np}$ of the present invention. In specific embodiments, the rMDV$_{np}$ is an rHVT. In alternative embodiments, the rMDV$_{np}$ is an rMDV2.

In addition, the present invention provides methods for aiding in the protection of poultry against a disease caused by ILTV and/or NDV and/or MDV1 by administering such a vaccine and/or immunogenic composition of the present invention. In specific embodiments, such methods aid in the protection of a chicken. In particular embodiments of this type, a vaccine of the present invention is administered subcutaneously. In other embodiments, a vaccine of the present invention is administered in ovo.

Accordingly in one aspect, the present invention provides stable, safe, and efficacious immunogenic compositions and/or vaccines that comprise an rMDV$_{np}$ of the present invention. The present invention also provides immunogenic compositions and/or vaccines that comprise any rMDV$_{np}$ of the present invention that is further combined with an additional NDV, ILTV, and/or MDV antigen to improve and expand the immunogenicity provided. In addition, the present invention also provides immunogenic compositions and/or vaccines that comprise any rMDV$_{np}$ of the present invention that is further combined with an antigen for a pathogen other than MDV, ILTV, or NDV. In a particular embodiment of this type, the antigen is an Infectious Bursal Disease Virus (IBDV) antigen. In a more particular embodiment the IBDV antigen is a mild live IBDV. In certain embodiments the mild live IBDV is a variant IBDV. The present invention also provides methods for aiding in the protection of poultry against a disease caused by ILTV and/or NDV and/or MDV1 and/or IBDV by administering such a vaccine and/or immunogenic composition to the poultry (e.g., chicken). In particular embodiments of this type, a vaccine of the present invention is administered subcutaneously. In other embodiments, a vaccine of the present invention is administered in ovo.

In certain embodiments the immunogenic compositions and/or vaccines of the present invention comprise an rHVT that comprises as an insertion into its US2 site of a recombinant nucleic acid comprising 5' to 3': (i) an Infectious Laryngotracheitis Virus (ILTV) gD promoter; (ii) a coding sequence for the ILTV gD protein; (iii) an ILTV gI promoter; (iv) a coding sequence for the ILTV gI protein; (v) a human cytomegalovirus immediate early (hCMV 1E) promoter; (vi) a coding sequence for the Newcastle Disease Virus fusion protein (NDV F); and (vii) a transcription terminator sequence. In particular embodiments of this type the immunogenic compositions and/or vaccines further comprise a mild live infectious bursal disease virus (IBDV). In certain embodiments the mild live IBDV is a variant IBDV. In more particular embodiments, the IBDV is 89/03. In even more particular embodiments of this type, the recombinant nucleic acid has the nucleotide sequence of SEQ ID NO: 17.

The present invention further provides immunogenic compositions and/or vaccines that comprise any rMDV$_{np}$ of the present invention combined with an additional NDV, ILTV, and/or MDV antigen, and a pathogen other than MDV, ILTV, or NDV.

These and other aspects of the present invention will be better appreciated by reference to the following Figures and the Detailed Description.

BRIEF DESCRIPTION OF THE DRAWINGS

FIG. 2 is a schematic drawing of six different recombinant HVTs, which depict the genes inserted into the HVT backbone and the site of their insertion. Innovax-LT is an rHVT that includes an expression cassette encoding the ILTV gD and ILTV gI genes inserted in the UL54.5 site of the rHVT. Innovax-ND is an rHVT that includes an expression cassette encoding the NDV fusion gene inserted in the US10 site of the rHVT. 1348-34C is an rHVT that includes both an expression cassette encoding the ILTV gD and ILTV gI genes inserted in the UL54.5 site of the rHVT, and an expression cassette encoding the NDV fusion gene inserted in the US10 site of the rHVT. 1332-62E is an rHVT that includes an expression cassette that encodes the ILTV gD, the ILTV gI, and the NDV fusion genes inserted in the US2 site of the rHVT. 1317-46 is an rHVT that includes both an expression cassette encoding the ILTV gD and ILTV gI genes inserted in the US2 site, and an expression cassette encoding the NDV fusion gene inserted between UL7 and UL8 (i.e., the UL7/8 site) of the rHVT. 1332-70B is an rHVT that includes an expression cassette that encodes the ILTV gD, the ILTV gI, and the NDV fusion genes inserted in the UL54.5 site of the rHVT.

DETAILED DESCRIPTION OF THE INVENTION

Figure 1:
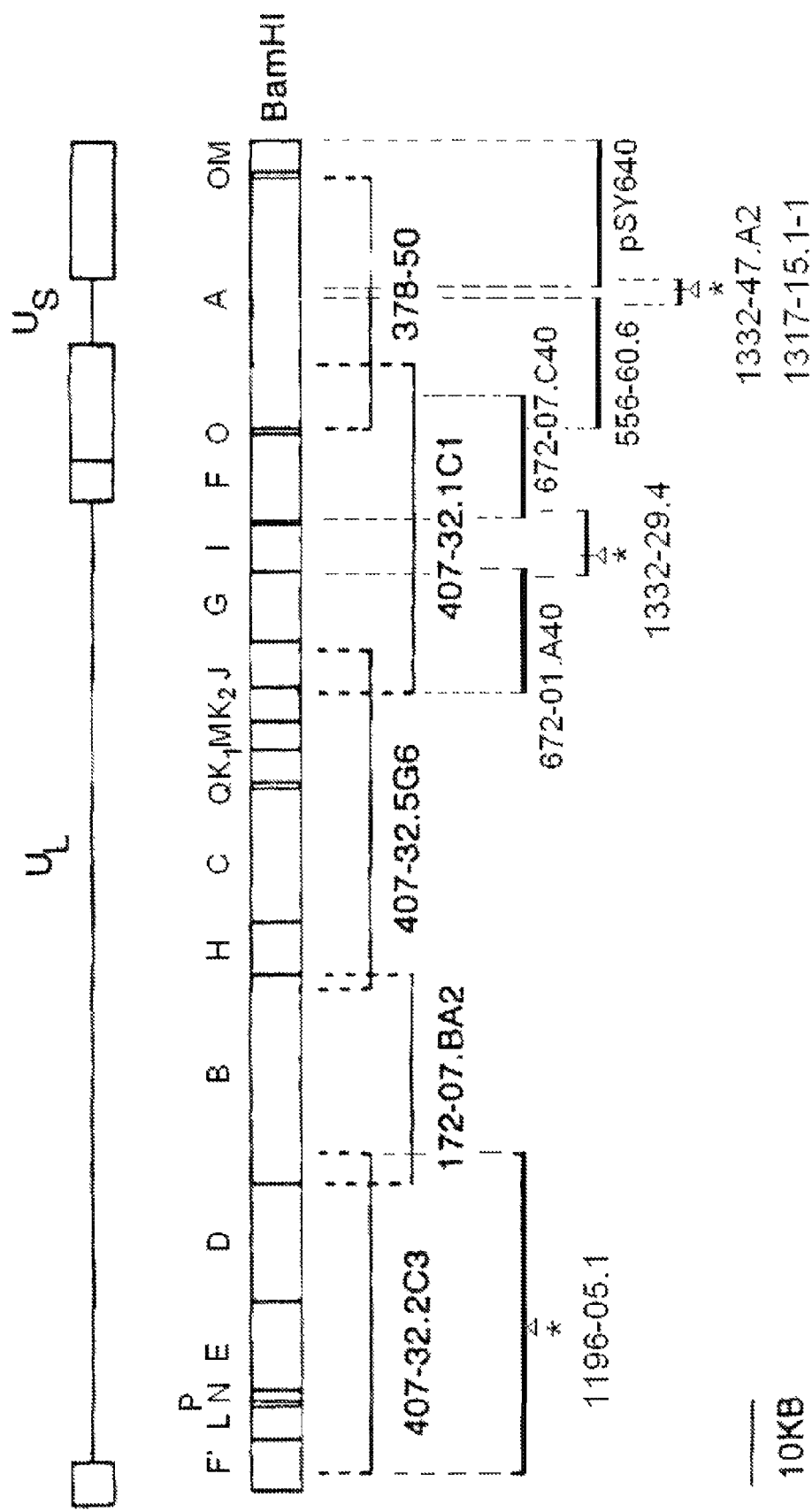
FIG. 1 is a schematic drawing of the HVT (FC126) genome, consisting of a unique long (UL) region, and a unique short (US) region, each denoted by straight lines, and flanked by repeat regions, denoted as boxes. Below the genome schematic, is a bar indicating the location of BamHI restriction enzyme digestion fragments, relative to their genome position, and the lettering nomenclature associated with each fragment. (The largest fragment was given the letter "A", the next largest given the letter "B", and so forth and so on). The positions of each cloned subgenomic fragment (and their designation) used to reconstruct either HVT (FC126) or the rHVT/NDV/ILT viruses are indicated below the BamHI restriction map. The asterisk (*) indicates the position of the insertion sites: UL7/UL8 in 1196-05.1; UL54.5 in 1332-29.4; US2 in 1332-47.A2 or 1317-15.1-1.

The present invention overcomes the prior industry failure to be able to construct rMDV$_{np}$ vectors that both contain foreign antigens and can protect against two or more different poultry virus pathogens by providing unique recombinant MDV$_{np}$ vectors that encode and express antigens from ILTV and NDV, and that protect against Mareks disease, Newcastle disease, and Infectious Laryngotraceitis virus. In particular embodiments, an rMDV$_{np}$ of the present invention encodes and expresses foreign antigens from only ILTV and NDV, and can aid in the protection against Mareks disease, Newcastle disease, and Infectious Laryngotraceitis virus. In specific embodiments, the rMDV$_{np}$ is an rHVT. In alternative embodiments, the rMDV$_{np}$ is an rMDV2.

Prior to the present invention, an HVT vector already had been constructed containing an NDV gene inserted into the US10 region. This HVT-NDV vector was shown to be stable and to express sufficient levels of the corresponding NDV gene product, the NDV F protein, to protect vaccinated chickens against a virulent NDV challenge. In addition, an HVT vector already had been constructed containing a pair of ILTV genes inserted in the HVT UL54.5 region. This HVT-ILTV vector was shown to be stable and to express sufficient levels of the corresponding ILTV gene products, the ILTV gI and gD proteins, to protect vaccinated chickens against a virulent ILTV challenge virus.

Accordingly, a multivalent HVT construct to protect against both NDV and ILTV was designed based on the successful constructs above, i.e., inserting the NDV-F gene in the US10 site and inserting the ILTV gD and gI genes in UL54.5 site [see, 1348-34C in FIG. 2]. Unexpectedly however, following the passaging of this construct in tissue culture the recombinant virus lost its ability to express the ILTVgD, ILTVgI, and NDV F proteins. This proved to be true with a number of duplicate recombinant rHVT constructs. Indeed, these recombinant viruses were unstable and unsuitable for further development as vaccines. These findings demonstrate that the design of a single multivalent rHVT vector that can stably express both the NDV F protein and the ILTVgD and ILTVgI proteins is not a simple process that can be extrapolated from existing information. Indeed, if such stable and efficacious multivalent rHVT vectors were possible at all, their design needed to be premised on an unpredictable set of complex interactions minimally involving the relationship between the insertion sites used and the foreign genes to be inserted. Heretofore, such design of rHVT constructs was not readily predictable from the known art.

The present invention therefore, provides recombinant rMDV$_{np}$ vectors in which two genes from ILTV and one gene from NDV have been inserted. In a particular embodiment of the present invention all three genes were inserted in the US2 region of the HVT genome. Upon vaccination of a chicken or a chicken egg with this rHVT, the cells of the immunized host expressed the proteins encoded by the inserted genes. Furthermore, the NDV and ILTV proteins expressed by the rHVT stimulated an immune response that protected the vaccinated chicken against the disease caused by NDV and ILTV. Accordingly, such rMDV$_{np}$ vectors can be used to provide protection against both NDV and ILTV infections. Previously, two separate rHVT vectors were necessary to protect against these two viruses, namely one for protection against ILTV and the other for protection against NDV.

The present invention therefore, is advantageous over current methods because it provides simultaneous protection against ILTV and NDV by inoculation of poultry and/or poultry eggs with only a single recombinant MDV$_{np}$. In particular, this allows for additional vaccines to be administered via the in ovo route, because there is a limit on how much volume can be injected into an egg, and further saves on manufacturing costs because only one rather than two vectors is needed. Moreover, this can allow an additional antigen to be included in the vaccine such as a live IBDV, e.g., strain 89/03.

Moreover, the present invention further includes embodiments that comprise different rMDV$_{np}$ constructs in the same vaccine and/or immunogenic compositions. In certain embodiments of this type, the vaccine and/or immunogenic composition comprise both an rMDV2 and an rHVT, each of which encode one or more foreign antigens. Indeed, unlike the combination of two rHVTs, which inevitably lead to one construct significantly overgrowing the other, combining an rHVT with an rMDV2 leads to no such significant overgrowth. Therefore, in specific embodiments, a vaccine of the present invention comprises an rHVT that encodes an ILTVgD protein, an ILTVgI protein, and an NDV F protein with an rMDV2 that encodes yet another poultry viral antigen.

In order to more fully appreciate the instant invention, the following definitions are provided.

The use of singular terms for convenience in description is in no way intended to be so limiting. Thus, for example, reference to a composition comprising "a polypeptide" includes reference to one or more of such polypeptides.

As used herein a "nonpathogenic Marek's Disease Virus" or "MDV$_{np}$" or "npMDV" is a virus in the MDV family that shows little to no pathogenicity in poultry. The term "MDV$_{np}$" includes naturally occurring MDVs that have been passaged or otherwise similarly manipulated, but does not include viral constructs in which a specific region of the genome of one MDV serotype is replaced by the corresponding region of a different MDV serotype to form a chimeric virus, such as the novel avian herpesvirus (NAHV). In certain embodiments, the MDV$_{np}$ is an HVT. In other embodiments, the MDV$_{np}$ is an MDV2. In particular embodiments of this type, the MDV2 is SB1.

As used herein, an MDV$_{np}$ that has been genetically modified to encode a heterologous nucleotide sequence (e.g., a foreign gene) is defined as a "recombinant MDV$_{np}$" or "rMDV$_{np}$".

As used herein, a "nonessential site" is a site in the MDV$_{np}$ genome in which an insertion of a heterologous nucleotide sequence into that site does not prevent the MDV$_{np}$ from replicating in a host cell. Nonessential sites are generally identified by the gene in which they reside, e.g., the US2 site, or a region between two genes, e.g., the UL7/8 site.

As used herein the term "poultry" can include chickens, turkeys, ducks, geese, quail, and pheasants.

As used herein, a "vaccine" is a composition that is suitable for application to an animal (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating or curing the clinical disease.

As used herein, a "multivalent vaccine" is a vaccine that comprises two or more different antigens. In a particular embodiment of this type, the multivalent vaccine stimulates the immune system of the recipient against two or more different pathogens.

As used herein, the term "aids in the protection" does not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal or transdermal), underneath the skin (subcutaneous), underneath the mucosa (submucosal), in the veins (intravenous) etc.

As used herein the term "parenteral administration" includes subcutaneous injections, submucosal injections, intravenous injections, intramuscular injections, intradermal injections, and infusion.

The term "approximately" is used interchangeably with the term "about" and signifies that a value is within twenty-five percent of the indicated value i.e., a peptide containing "approximately" 100 amino acid residues can contain between 75 and 125 amino acid residues.

As used herein, the term, "polypeptide" is used interchangeably with the terms "protein" and "peptide" and denotes a polymer comprising two or more amino acids connected by peptide bonds. The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 155, 154, 153, etc., in all practical combinations.

Optionally, a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

As used herein the term "antigenic fragment" in regard to a particular protein (e.g., a protein antigen) is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor. For example, an antigenic fragment of an NDV fusion protein, is a fragment of that fusion protein that is antigenic. Preferably, an antigenic fragment of the present invention is immunodominant for antibody and/or T cell receptor recognition.

As used herein an amino acid sequence is 100% "homologous" to a second amino acid sequence if the two amino acid sequences are identical, and/or differ only by neutral or conservative substitutions as defined below. Accordingly, an amino acid sequence is about 80% "homologous" to a second amino acid sequence if about 80% of the two amino acid sequences are identical, and/or differ only by neutral or conservative substitutions.

Functionally equivalent amino acid residues often can be substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. The amino acids also can be placed in the following similarity groups: (1) proline, alanine, glycine, serine, and threonine; (2) glutamine, asparagine, glutamic acid, and aspartic acid; (3) histidine, lysine, and arginine; (4) cysteine; (5) valine, leucine, isoleucine, methionine; and (6) phenylalanine, tyrosine, and tryptophan.

In a related embodiment, two highly homologous DNA sequences can be identified by their own homology, or the homology of the amino acids they encode. Such comparison of the sequences can be performed using standard software available in sequence data banks. In a particular embodiment two highly homologous DNA sequences encode amino acid sequences having about 80% identity, more preferably about 90% identity and even more preferably about 95% identity. More particularly, two highly homologous amino acid sequences have about 80% identity, even more preferably about 90% identity and even more preferably about 95% identity.

As used herein, protein and DNA sequence percent identity can be determined using software such as MacVector v9, commercially available from Accelrys (Burlington, Massachusetts) and the Clustal W algorithm with the alignment default parameters, and default parameters for identity. See, e.g., Thompson, et al,. 1994. *Nucleic Acids Res.* 22:4673-4680. ClustalW is freely downloadable for Dos, Macintosh and Unix platforms from, e.g., EMBLI, the European Bioinformatics Institute. These and other available programs can also be used to determine sequence similarity using the same or analogous default parameters.

As used herein the terms "polynucleotide", or a "nucleic acid" or a "nucleic acid molecule" are used interchangeably and denote a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

A nucleic acid "coding sequence" or a "sequence encoding" a particular protein or peptide, is a nucleotide sequence which is transcribed and translated into a polypeptide in vitro or in vivo when placed under the control of appropriate regulatory elements.

The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., avian) DNA, and even synthetic DNA sequences. A transcription termination sequence can be located 3' to the coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the term "transcription terminator sequence" is used interchangeably with the term "polyadenylation regulatory element" and is a sequence that is generally downstream from a DNA coding region and that may be required for the complete termination of the transcription of that DNA coding sequence.

As used herein an "expression cassette" is a recombinant nucleic acid that minimally comprises a promoter and a heterologous coding sequence operably linked to that promoter. In many such embodiments, the expression cassette further comprises a transcription terminator sequence. Accordingly, the insertion of an expression cassette into a nonessential site of the rMDV$_{np}$ genome can lead to the expression of the heterologous coding sequence by the rMDV$_{np}$. In specific embodiments, the rMDV$_{np}$ is an rHVT. In alternative embodiments, the rMDV$_{np}$ is an rMDV2.

A "heterologous nucleotide sequence" as used herein is a nucleotide sequence that is added to a nucleotide sequence of the present invention by recombinant methods to form a nucleic acid that is not naturally formed in nature. In specific embodiments, a "heterologous nucleotide sequence" of the present invention can encode a protein antigen such as the NDV F protein, the ILTV gI protein, or the ILTV gD protein. Heterologous nucleotide sequences can also encode fusion (e.g., chimeric) proteins. In addition, a heterologous nucleotide sequence can encode peptides and/or proteins that contain regulatory and/or structural properties. In other such embodiments, a heterologous nucleotide sequence can encode a protein or peptide that functions as a means of detecting the protein or peptide encoded by the nucleotide sequence of the present invention after the recombinant nucleic acid is expressed. In still another embodiment, the heterologous nucleotide sequence can function as a means of detecting a nucleotide sequence of the present invention. A heterologous nucleotide sequence can comprise non-coding sequences including restriction sites, regulatory sites, promoters and the like.

Insertion of a nucleic acid encoding an antigen of the present invention into a rMDV$_{np}$ vector is easily accomplished when the termini of both the nucleic acid and the vector comprise compatible restriction sites. If this cannot be done, it may be necessary to modify the termini of the nucleotide sequence and/or vector by digesting back single-stranded nucleic acid overhangs (e.g., DNA overhangs) generated by restriction endonuclease cleavage to produce blunt ends, or to achieve the same result by filling in the single-stranded termini with an appropriate polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). [See, e.g., Saiki et al., *Science* 239:487-491 (1988)]. The cleaved vector and the DNA fragments may also be modified, if required, by homopolymeric tailing.

Protein Antigens and Nucleic Acids Encoding the Protein Antigens

The ILTV gD gene appears to encode a glycoprotein of 434 amino acids in length having a molecular weight of 48,477 daltons, although others have suggested that a downstream start codon, which leads to an ILTV gD protein comprising only 377 amino acid residues, is the actual start codon [Wild et al., *Virus Genes* 12:104-116 (1996)]. The ILTV gI gene encodes a glycoprotein of 362 amino acids in length having a molecular weight of 39,753 daltons [U.S. Pat. No. 6,875,856, hereby incorporated by reference]. Nucleic acids encoding natural and/or laboratory derived variants of the ILTV gD and ILTV gI may be substituted for those presently exemplified.

In particular embodiments of the present invention, an rMDV$_{np}$ comprises a recombinant nucleic acid (e.g., an expression cassette) that encodes an ILTV gD protein comprising the amino acid sequence of SEQ ID NO: 2 or an antigenic fragment thereof. In related embodiments the rMDV$_{np}$ comprises a recombinant nucleic acid that encodes an ILTV gD protein comprising an amino acid sequence that has greater than 90%, and/or greater than 95%, and/or greater than 98%, and/or greater than 99% identity to the amino acid sequence of SEQ ID NO: 2. In particular embodiments, the ILTV gD protein is encoded by the nucleotide sequence of SEQ ID NO: 1. In specific embodiments, the rMDV$_{np}$ is an rHVT. In alternative embodiments, the rMDV$_{np}$ is an rMDV2.

In certain embodiments of the present invention, an rMDV$_{np}$ comprises a recombinant nucleic acid (e.g., an expression cassette) that encodes an ILTV gI protein comprising the amino acid sequence of SEQ ID NO: 4 or an antigenic fragment thereof. In related embodiments, the rMDV$_{np}$ comprises a recombinant nucleic acid that encodes an ILTV gI protein comprising an amino acid sequence that has greater than 90%, and/or greater than 95%, and/or greater than 98%, and/or greater than 99% identity to the amino acid sequence of SEQ ID NO: 4. In particular embodiments, the ILTV gI protein is encoded by the nucleotide sequence of SEQ ID NO: 3. In specific embodiments, the rMDV$_{np}$ is an rHVT. In alternative embodiments, the rMDV$_{np}$ is an rMDV2.

The NDV F protein gene encodes the so-called "fusion" protein. One NDV F protein gene exemplified by the present invention was derived from NDV Clone 30, a common lentogenic NDV vaccine strain. Nucleic acids encoding natural and/or laboratory derived variants of the F protein gene would equally be applicable, either from lentogenic, mesogenic or velogenic NDV, as the F protein gene sequence itself is highly conserved in these different NDV pathotypes. In particular embodiments of the present invention, an rMDV$_{np}$ comprises a recombinant nucleic acid (e.g., an expression cassette) that encodes an NDV fusion protein comprising the amino acid sequence of SEQ ID NO: 6 or an antigenic fragment thereof. In related embodiments, the rMDV$_{np}$ comprises a recombinant nucleic acid that encodes an NDF F protein comprising an amino acid sequence that has greater than 90%, and/or greater than 95%, and/or greater than 98%, and/or greater than 99% identity to the amino acid sequence of SEQ ID NO: 6. In specific embodiments, the NDV fusion protein is encoded by the nucleotide sequence of SEQ ID NO: 5. In certain embodiments of the present invention, an rMDV$_{np}$ comprises a recombinant nucleic acid (e.g., an expression cassette) that encodes an NDV fusion protein comprising the amino acid sequence of SEQ ID NO: 8 or an antigenic fragment thereof. In related embodiments, an rMDV$_{np}$ comprises a recombinant nucleic acid that encodes an NDF F protein comprising an amino acid sequence that has greater than 90%, and/or greater than 95%, and/or greater than 98%, and/or greater than 99% identity to the amino acid sequence of SEQ ID 8. In particular embodiments, the NDV fusion protein is encoded by the nucleotide sequence of SEQ ID NO: 7. In specific embodiments, the rMDV$_{np}$ is an rHVT. In alternative embodiments, the rMDV$_{np}$ is an rMDV2.

Promoters and Polyadenylation Regulatory Elements

Many alternative promoters can be used to drive the expression of a heterologous gene encoding a protein antigen or antigenic fragment thereof in an rMDV$_{np}$ of the present invention. Examples include the pseudorabies virus (PRV) gpX promoter [see, WO 87/04463], the Rous sarcoma virus LTR promoter, the SV40 early gene promoter, the ILTV gD promoter, the ILTV gI promoter [see e.g., U.S. Pat. No. 6,183, 753 B1], the human cytomegalovirus immediate early1 (hCMV IE1) gene promoter [U.S. Pat. Nos. 5,830,745; 5,980, 906], and the chicken beta-actin gene promoter [EP 1 298 139 B1]. More specific examples, as exemplified herein, include the Towne Strain hCMV IE promoter comprising the nucleotide sequence of SEQ ID NO: 12, a truncated hCMV IE promoter comprising the nucleotide sequence of SEQ ID NO: 11, an ILTV gD promoter comprising the nucleotide sequence of SEQ ID NO: 9, and an ILTV gI promoter comprising the nucleotide sequence of SEQ ID NO: 10.

The inclusion of a polyadenylation regulatory element downstream from a DNA coding region is oftentimes required to terminate the transcription of the coding DNA sequence. Accordingly, many genes comprise a polyadenylation regulatory element at the downstream end of their coding sequence. Many such regulatory elements have been identified and can be used in an rMDV$_{np}$ of the present invention. Specific examples of polyadenylation regulatory elements as exemplified herein, include a synthetic polyadenylation signal comprising the nucleotide sequence of SEQ ID NO: 13, and the HSV thymidine kinase polyadenylation signal comprising the nucleotide sequence of SEQ ID NO: 14.

Vaccines and Immunogenic Compositions

The present invention relates to the use of the recombinant MDV$_{np}$, the nucleic acid molecules used to construct the MDV$_{np}$, or the host cells to grow them, or any combination thereof, all according to the present invention for the manufacture of a vaccine for poultry. Accordingly, the present invention provides vaccines and/or immunogenic compositions that include a multivalent recombinant MDV$_{np}$ of the present invention. Such vaccines can be used to aid in the prevention and/or prevent Newcastle disease, and/or Marek's disease, and/or maladies associated with ILTV infections. A vaccine according to the present invention can be used for prophylactic and/or for therapeutic treatment, and thus can interfere with the establishment and/or with the progression of an infection and/or its clinical symptoms of disease.

A recombinant MDV$_{np}$ of the present invention can be grown by any number of means currently practiced in the field. For example, a recombinant MDV$_{np}$ of the present invention can be grown through the use of in vitro cultures of primary chicken cells, see e.g., the Examples below where chicken embryo fibroblast cells (CEFs) were used. The CEFs can be prepared by trypsinization of chicken embryos. The CEFs also can be plated in monolayers and then infected with the MDV$_{np}$. This particular process can be readily scaled up to industrial-sized production.

Therefore, a further aspect of the invention relates to a method for the preparation of the vaccine according to the invention comprising the steps of infecting host cells with a recombinant MDV$_{np}$ of the present invention, harvesting the infected host cells, and then admixing the harvested infected host cells with a pharmaceutically acceptable carrier. Suitable methods for infection, culture and harvesting are well known in the art and are described and exemplified herein.

Typically, the infected host cells are harvested while still intact to obtain the recombinant MDV$_{np}$ in its cell-associated form. These cells can be taken up in an appropriate carrier composition to provide stabilization for storage and freezing. The infected cells can be filled into glass ampoules, which are sealed, frozen and stored in liquid nitrogen. Accordingly, in certain embodiments of the present invention, the vaccines and/or immunogenic compositions of the present invention are stored frozen and accordingly, comprise a cryopreservative, such as dimethyl sulfoxide (DMSO), to preserve the frozen infected cells.

Alternatively, when the recombinant MDV$_{np}$ is a recombinant HVT, it can be isolated from its host cell, for instance through sonication at the end of culturing, and then taken up into a stabilizer, and freeze-dried (lyophilized) for stable storage or otherwise reduced in liquid volume, for storage, and then reconstituted in a liquid diluent before or at the time of administration. Such reconstitution may be achieved using, for example, vaccine-grade water. In certain embodiments, a lyophilized portion of a multivalent vaccine can comprise one or more antigens and the diluent can comprise one or more other antigens.

In particular embodiments a vaccine of the present invention (or a portion thereof) can be in a freeze-dried form, e.g., as tablets and/or spheres that are produced by a method described in WO 2010/125084, hereby incorporated by reference in its entirety. In particular, reference is made to the examples, from page 15, line 28 to page 27, line 9 of WO 2010/125084, describing a method to produce such fast disintegrating tablets/spheres. Such freeze-dried forms can be readily dissolved in a diluent, to enable systemic administration of the vaccine.

Vaccines and immunogenic compositions can, but do not necessarily include, physiologically compatible buffers and saline and the like, as well as pharmaceutically acceptable adjuvants. Adjuvants can be useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention can further comprise an adjuvant. Examples of chemical compounds that can be used as adjuvants include, but are not limited to aluminum compounds (e.g., aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12) and CARBOPOL®.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens. Generally, an adjuvant is administered at the same time as an antigen of the present invention. However, adjuvants can also or alternatively be administered within a two-week period prior to the vaccination, and/or for a period of time after vaccination, i.e., so long as the antigen, e.g., a recombinant MDV$_{np}$ of the present invention persists in the tissues.

The vaccines and/or immunogenic compositions of the present invention may be administered by any route such as in ovo, by parenteral administration, including intramuscular injection, subcutaneous injection, intravenous injection, intradermal injection, by scarification, by oral administration, or by any combination thereof.

Furthermore, the multivalent recombinant MDV$_{np}$ of the present invention can be used and/or combined with additional NDV, ILTV, and/or MDV antigens to improve and expand the immunogenicity provided, and/or antigens for other pathogens in order to provide immune protection against such other pathogens. These additional antigens can be either live or killed whole microorganisms, other recombinant vectors, cell homogenates, extracts, proteins, or any other such derivative, provided that they do not negatively interfere with the safety, stability, and efficacy of the vaccine according to the present invention.

The combination of a multivalent recombinant MDV$_{np}$ of the present invention with an additional MDV, NDV, and/or ILTV antigen can be advantageous in those cases in which very virulent field strains of MDV, NDV, or ILTV are prevalent, e.g., in a particular geographic region. In this regard, the combination of a multivalent recombinant MDV$_{np}$ of the present invention with an MDV1, MDV2, or HVT includes the Rispens (MDV1) strain, the SB1 (MDV2) strain, the FC-126 (HVT) strain and/or PB1 (HVT) strain. To improve the response against NDV, multivalent recombinant MDV$_{np}$ may be combined with an NDV vaccine strain, such as the mild live NDV vaccine strain C2.

Examples of other microorganisms that can be used as antigens together with the multivalent recombinant MDV$_{np}$ of the present invention include: (i) viruses such as infectious bronchitis virus, adenovirus, egg drop syndrome virus, infectious bursal disease virus, chicken anaemia virus, avian encephalo-myelitis virus, fowl pox virus, turkey rhinotracheitis virus, duck plague virus (duck viral enteritis), pigeon pox virus, avian leucosis virus, avian pneumovirus, and reovirus, (ii) bacteria, such as *Escherichia coli, Salmonella* spec., *Ornitobacterium rhinotracheale, Haemophilis paragallinarum, Pasteurella multocida, Erysipelothrix rhusiopathiae, Erysipelas* spec., *Mycoplasma* spec., and *Clostridium* spec., (iii) parasites such as Eimeria spec., and (iv) fungi, such as *Aspergillus* spec. In particular embodiments of the present invention, a recombinant MDV$_{np}$ of the present invention can be combined with a mild live IBDV vaccine strain such as D78 (cloned intermediate strain), PBG98, Cu-1, ST-12 (an intermediate strain), or 89-03 (a live Delaware variant strain) in a multivalent vaccine. Many of such strains are used in commercial vaccines.

The combination vaccine can be made in a variety of ways including by combining the recombinant MDV$_{np}$ of the present invention with preparations of virus, or bacteria, or fungi, or parasites, or host cells, or a mixture of any and/or all of these. In particular embodiments, the components for such a combination vaccine are conveniently produced separately and then combined and filled into the same vaccine container.

As described above, a vaccine according to the invention can be used advantageously to provide safe and effective immune protection in poultry to a multiple diseases, by a single inoculation at very young age or in ovo. Alternatively, as would be apparent to anyone skilled in the art of poultry vaccines the combinations described above also could include vaccination schedules in which the multivalent recombinant MDV$_{np}$ of the present invention and the additional antigen are not applied simultaneously; e.g., the recombinant MDV$_{np}$ may be applied in ovo, and the NDV C2 and/or the IBDV strain (e.g., 89/03) could be applied at a subsequent time/date.

Accordingly, the vaccines of the present invention can be administered to the avian subject in a single dose or in multiple doses. For example, a vaccine of the present invention may be applied at the day of hatch and/or in ovo at day 16-18 (Embryonation Day) ED. When multiple doses are administered, they may be given either at the same time or sequentially, in a manner and time compatible with the formulation of the vaccine, and in such an amount as will be immunologically effective. Therefore, a vaccine of the present invention may effectively serve as a priming vaccination, which later can be followed and amplified by a booster vaccination of the identical vaccine, or with a different vaccine preparation e.g., a classical inactivated, adjuvanted whole-virus vaccine.

The volume per dose of a vaccine of the present invention can be optimized according to the intended route of application: in ovo inoculation is commonly applied with a volume between 0.05 and 0.5 ml/egg, and parenteral injection is commonly done with a volume between 0.1 and 1 ml/avian. In any case, optimization of the vaccine dose volume is well within the capabilities of the skilled artisan.

Sequence Table

| SEQ ID NO: | Description | Type |
| --- | --- | --- |
| 1 | ILTV gD Glycoprotein | nucleic acid |
| 2 | ILTV gD Glycoprotein | amino acid |
| 3 | ILTV gI Glycoprotein | nucleic acid |
| 4 | ILTV gI Glycoprotein | amino acid |
| 5 | NDV F Protein (Clone 30) | nucleic acid |
| 6 | NDV F Protein (Clone 30) | amino acid |
| 7 | NDV F Protein (B1 Hitchner) | nucleic acid |
| 8 | NDV F Protein (B1 Hitchner) | amino acid |
| 9 | ILTV gD promoter | nucleic acid |
| 10 | ILTV gI promoter | nucleic acid |
| 11 | hCMV IE promoter (Truncated) | nucleic acid |
| 12 | hCMV IE promoter (Towne Strain) | nucleic acid |
| 13 | synthetic polyadenylation signal | nucleic acid |
| 14 | HSV TK polyadenylation signal | nucleic acid |
| 15 | IE-NDV F insert | nucleic acid |
| 16 | ILTV insert | nucleic acid |
| 17 | ILTV/IE-NDV F insert | nucleic acid |

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

Example 1

Construction of Recombinant HVT/NDV/ILTV Virus Vectors

The ability to generate herpesviruses by cotransfection of cloned overlapping subgenomic fragments was first demonstrated for pseudorabies virus [van Zijl et al., *J. Virology* 62:2191-2195 (1988)]. This procedure subsequently was employed to construct recombinant HVT vectors [see, U.S. Pat. No. 5,853,733, hereby incorporated by reference with respect to the methodology disclosed regarding the construction of recombinant HVT vectors] and was used to construct the recombinant HVT/NDV/ILTV vectors of the present invention. In this method, the entire HVT genome is cloned into bacterial vectors as several large overlapping subgenomic fragments constructed utilizing standard recombinant DNA techniques [Maniatis et al., (1982) *Molecular Cloning*, Cold Spring Harbor Laboratory Press, Cold Spring Harbor, New York (1982); and Sambrook et al., *Molecular Cloning*, Cold Spring Harbor Laboratory Press, Cold Spring Harbor, N.Y. (1989)]. An HVT strain FC126 cosmid library was derived from sheared viral DNA cloned into the cosmid vector, pWE15 (Stratagene, now Agilent Technologies of Santa Clara, Calif.). In addition, several large genomic DNA fragments were isolated by restriction digestion with the enzyme, BamHI, and cloned into either pWE15 or the plasmid vector pSP64 (Promega, Madison Wis.). As described in U.S. Pat. No. 5,853,733, cotransfection of these fragments into chicken embryo fibroblast (CEF) cells results in the regeneration of the HVT genome mediated by homologous recombination across the overlapping regions of the fragments. If an insertion is engineered directly into one or more of the subgenomic fragments prior to the cotransfection, this procedure results in a high frequency of viruses containing the insertion. Five overlapping subgenomic clones are required to generate FC126 HVT, and served as the basis for creating all HVT/NDV/ILTV recombinant viruses.

Construction of HVT/NDV/ILTV 1332-62.E1: The cosmid regeneration for HVT/NDV/ILTV 1332-62.E1 was performed essentially as described in U.S. Pat. No. 5,853,733 [e.g. FIG. 8 of U.S. Pat. No. 5,853,733; redrawn, at least in part, in FIG. 1, herein]. To allow integrations into the US region of the FC126 HVT genome, the region covered by the cosmid nr. 378-50 in U.S. Pat. No. 5,853,733, was now provided from three smaller plasmids: pSY640 and 556-60.6, and one transfer plasmid (1332-47.A2), overlapping these two, and containing the ILTV/NDV expression cassettes in the US2 gene locus.

The set of seven linearized constructs: 3 cosmids and 4 plasmids are transfected all together into CEFs, using a standard $CaCl_2$ transfection protocol and the resulting virus stock was plaque purified one time.

Construction of HVT/NDV/ILTV 1332-70.81: The cosmid regeneration for HVT/NDV/ILTV 1332-70.B1 was performed essentially as described in U.S. Pat. No. 5,853,733 [e.g., FIG. 8 of U.S. Pat. No. 5,853,733; redrawn, at least in part, in FIG. 1, herein]. To allow integrations into the UL54.5 region of the FC126 HVT genome, the region covered by the cosmid nr. 407-32.1C1 in U.S. Pat. No. 5,853,733 was now provided from three smaller plasmids: 672-01.A40 and 672-07.C40, and one transfer plasmid (1332-29.4), overlapping these two, and containing the ILTV/NDV expression cassettes in the UL54.5 gene locus.

The set of seven linearized constructs: 4 cosmids and 3 plasmids are transfected all together into CEFs, using a standard $CaCl_2$ transfection protocol, and the resulting virus stock was plaque purified one time.

Construction of HVT/NDV/ILTV 1317-46.A1-1: The cosmid regeneration for HVT/NDV/ILTV 1317-46.A1-1 was performed essentially as described in U.S. Pat. No. 5,853,733 [e.g., FIG. 8 of U.S. Pat. No. 5,853,733; redrawn, at least in part, in FIG. 1, herein]. To allow integrations into the US region of the FC126 HVT genome, the region covered by the cosmid nr. 378-50 in U.S. Pat. No. 5,853,733, was now provided from three smaller plasmids: pSY640 and 556-60.6, and one transfer plasmid (1317-15.1-1), overlapping these two, and containing the ILTV expression cassette inserted into the US2 gene locus. Insertion into a second site within the FC126 HVT genome was accomplished by replacing the UL region cosmid nr. 407-32.2C3 in U.S. Pat. No. 5,853,733 with the transfer cosmid (1196-05.1), containing the NDV expression cassette inserted between the HVT UL7 and UL8 genes.

The set of seven constructs: 1 uncut cosmid (1196-05.1), the remaining 2 linearized cosmids, and 4 linearized plasmids were transfected all together into CEFs, using a standard $CaCl_2$ transfection protocol, and the resulting virus stock was plaque purified one time.

Description of Subgenomic Fragments for Generating FC126 HVT:

SUBGENOMIC CLONE 407-32.2C3. Cosmid 407-32.2C3 contains an approximately 40,170 base pair region of genomic HVT DNA [Left terminus—pos. 39,754; Afonso et al., 2001, supra; Acc. #AF291866]. This region includes HVT BamHI fragments F', L, P, N1, E, D, and 2,092 base pairs of fragment B.

SUBGENOMIC CLONE 172-07.Ba2. Plasmid 172-07.BA2 contains a 25,931 base pair region of genomic HVT DNA. It was constructed by cloning the HVT BamHI B fragment [pos. 37,663 to 63,593; Afonso et al., 2001, supra; Acc. #AF291866] into the plasmid pSP64 (Promega, Madison Wis.).

SUBGENOMIC CLONE 407-32.5G6. Cosmid 407-32.5G6 contains a 39,404 base pair region of genomic HVT DNA [pos. 61,852-101,255; Afonso et al., 2001, supra; Acc. #AF291866]. This region includes HVT BamHI fragments H, C, Q, K1, M, K2, plus 1,742 base pairs of fragment B, and 3,880 base pairs of fragment J.

SUBGENOMIC CLONE 407-32.1C1. Cosmid 407-32.1C1 contains a 37,444 base pair region of genomic HVT DNA [pos. 96,095-133,538; Afonso et al., 2001, supra; Acc. #AF291866]. This region includes HVT BamHI fragments J, G, I, F, O, plus 1,281 base pairs of fragment K2, and 6,691 base pairs of fragment A.

SUBGENOMIC CLONE 378-50. Cosmid 378-50 contains a 28,897 base pair region of genomic HVT DNA [see FIG. 8 of U.S. Pat. No. 5,853,733; redrawn, at least in part, in FIG. 1, herein]. It was constructed by cloning the HVT BamHI A fragment [pos. 126848-155744; Afonso et al., 2001, supra; Acc. #AF291866] into the cosmid pWE15.

Additional Insertion Fragments for Generating HVT/NDV/ILTV 1332-62.E1:

SUBGENOMIC CLONE 1332-47.A2. The insertion plasmid 1332-47.A2 contains a 7311 base pair EcoRI fragment of the HVT unique short region [pos. 136880-144190; Afonso et al., 2001, supra; Acc. #AF291866], cloned into the plasmid pSP64 (Promega, Madison Wis.). Inserted into a unique StuI site within the HVT US2 gene [pos. 140540/140541, Afonso et al., 2001, supra; Acc. #AF291866, between amino acid residues 124 and 125] are 2 elements: a 3563 base pair SalI-HindIII fragment from ILTV, NVSL Challenge Strain, Lot #83-2 [pos. 10532-14094; Wild et al., *Virus Genes* 12:104-116 (1996); Acc.# U28832], encoding the full length genes for glycoprotein D (gD) and glycoprotein I (gI), plus partial coding regions from glycoprotein E (amino acids 1-101), and ORF5 (amino acids 734-985); and an expression cassette consisting of the HCMV IE promoter, the NDV, clone 30 strain, fusion gene (F), followed by a synthetic poly-adenylation signal. The ILTV gD, ILTV gI, and NDV F genes are transcribed in the opposite direction relative to the HVT US2 gene.

SUBGENOMIC CLONE pSY640. Plasmid pSY640 contains an approximately 13,600 base pair region of genomic HVT DNA [pos. 126848-140540; Afonso et al., 2001, supra; Acc. #AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega, Madison Wis.).

SUBGENOMIC CLONE 556-60.6. Plasmid 556-60.6 contains an approximately 12,500 base pair region of genomic HVT DNA derived from BamHI fragment A [approximate pos. 143300 to pos. 155744, Afonso et al., 2001, supra; Acc. #AF291866]. To generate this plasmid the region of DNA located downstream of the US2 gene beginning at the StuI site located in the US2 gene and continuing to the end of the BamHI A fragment was cloned into the plasmid pSP64 (Promega, Madison Wis.), and then treated with exonucleasse to "chewed back" from StuI site ~150 bp, and recloned into pBR322 plasmid vector.

Additional Insertion Fragments for Generating HVT/NDV/ILTV 1332-70.B1:

SUBGENOMIC CLONE 1332-29.4 Plasmid 1332-29.4 contains a 8,636 base pair region of genomic HVT DNA derived from the unique long region [pos. 109489-118124; Afonso et al., 2001, supra; Acc. #AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241, Afonso et al., 2001, supra; Acc. #AF291866, between amino acid residues 21 and 22] are 2 elements: a 3563 base pair SalI-HindIII fragment from ILTV, NVSL Challenge Strain, Lot #83-2 [pos. 10532-14094; Wild et al. 1996, supra; Acc.# U28832], encoding the full length genes for glycoprotein D (gD) and glycoprotein I (gI), plus partial coding regions from glycoprotein E (amino acids 1-101), and ORF5 (amino acids 734-985); and an expression cassette consisting of the HCMV IE promoter, the NDV, clone 30 strain, fusion gene (F), followed by a synthetic poly-adenylation signal. The ILTV gD, ILTV gI and NDV F genes are transcribed in the opposite direction relative to the HVT UL54.5 gene.

SUBGENOMIC CLONE 672-01.A40 Plasmid 672-01.A40 contains a 14,731 base pair region of genomic HVT DNA derived from the unique long region [pos. 96095-110825; Afonso et al., 2001, supra; Acc. #AF291866], cloned into a derivative of plasmid pNEB193. This region includes HVT BamHI fragments G, J and 1281 base pairs of K2.

SUBGENOMIC CLONE 672-07.C40 Plasmid 672-07.C40 contains a 12,520 base pair region of genomic HVT DNA derived from the unique long region [pos. 116948-129467; Afonso et al., 2001, supra; Acc. #AF291866], cloned into a derivative of plasmid pNEB193. This region includes HVT BamHI fragments F, O and 2620 base pairs of A.

Additional Insertion Fragments for Generating HVT/NDV/ILTV 1317-46.A1-1:

SUBGENOMIC CLONE 1196-05.1. Cosmid 1196-05.1 contains an approximately 40,170 base pair region of genomic HVT DNA [Left terminus—pos. 39,754; Afonso et al., 2001, supra; Acc. #AF291866] cloned into cosmid pWE15. This region includes HVT BamHI fragments F', L, P, N1, E, D, and 2,092 base pairs of fragment B. In addition an expression cassette encoding the NDV Fusion (F) gene, including the HCMV IE promoter and HSV TK poly-adenylation regulatory elements was inserted into a non-coding region between HVT UL7 and UL8 genes within BamHI fragment E [pos. 20030-20035; Afonso et al., 2001, supra; Acc. #AF291866]. The NDV F gene is transcribed the same direction as HVT UL7.

SUBGENOMIC CLONE 1317-15.1-1. Plasmid 1317-15.1-1 contains a 7311 base pair EcoRI fragment of the HVT unique short region [pos. 136880-144190; Afonso at al., 2001, supra; Acc. #AF291866], cloned into the plasmid pSP64 (Promega, Madison Wis.). In addition, a 3563 base pair SalI-HindIII fragment from ILTV, NVSL Challenge Strain, Lot #83-2 [pos. 10532-14094; Wild et al., 1996, supra; Acc.# U28832], encoding the full length genes for glycoprotein D (gD) and glycoprotein I (gI), plus partial coding regions from glycoprotein E (amino acids 1-101), and ORF5 (amino acids 734-985) were cloned into a unique StuI site within the HVT US2 gene [pos. 140540/140541, Afonso et al., 2001, supra; Acc. #AF291866, between amino acid residues 124 and 125]. The ILTV gD and gI genes are transcribed in the opposite direction relative to the HVT US2 gene.

SUBGENOMIC CLONE pSY640. Plasmid pSY640 contains an approximately 13,600 base pair region of genomic HVT DNA [pos. 126848-140540; Afonso et al., 2001, supra; Acc. #AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega, Madison Wis.).

SUBGENOMIC CLONE 556-60.6. Plasmid 556-60.6 contains an approximately 12,500 base pair region of genomic HVT DNA derived from BamHI fragment A [approximate pos. 143300 to pos. 155744, Afonso et al., 2001, supra; Acc. #AF291866]. To generate this plasmid the region of DNA located downstream of the US2 gene beginning at the StuI site located in the US2 gene and continuing to the end of the BamHI A fragment was cloned into the plasmid pSP64 (Promega, Madison Wis.), and then treated with exonucleasse to "chewed back" from StuI site ~150 bp, and recloned into pBR322 plasmid vector.

Standard $CaCl_2$ Transfection Protocol: Secondary CEF's are seeded on 6 well culture plates and incubated at 38° C. with 5% $CO_2$ for 24 hours and confluent monolayers form. For each well a total amount of 0.25 µg DNA of cosmids and plasmids were mixed in Hepes buffer and 125 mM $CaCl_2$ was added dropwise until precipitation was imminent. This mixture was added to the CEF cell monolayer, and incubated for 2 to 3 hrs. Supernatant was removed and an overlay of 15% Glycerol was added, and kept on the cells for 1 minute. Then this was removed, washed with PBS, and fresh culture medium was added and cells were incubated for 5 days. Next, cells were harvested by trypsinization and cells from individual plates were each seeded on fresh monolayers of CEF cells in 10 cm plates and incubated until 50-90% CPE was achieved. Next, the amplified transfected cells were harvested by trypsinization, and dilutions of $10^{-2}$ to $10^{-4}$ were plated on 10 cm plates with CEF monolayers and incubated. The following day, the plates were covered with agar, and a number of individual plaques of HVT/NDV/ILTV were isolated and amplified on CEFs.

Example 2

Recombinant HVT/ND/ILTV Vaccine Protects Day-Old Chicks Against Infectious Laryngotracheitis Virus Challenge Two vaccines, one comprising HVT/NDV/ILTV-1332-62E1 and the other, comprising 1332-70B1, were evaluated for efficacy in protecting chickens from an Infectious Laryngotracheitis Virus challenge. HVT/NDV/ILTV-1332-62E1 is an rHVT in which the FC126 HVT backbone comprises the nucleic acid sequence of SEQ ID NO: 17 inserted in the US2 site (see, Example 1 above). HVT/NDV/ILTV-1332-70B1 is an rHVT in which the FC126 HVT backbone comprises the nucleic acid sequence of SEQ ID NO: 17 inserted in the UL54.5 site (see, Example 1 above).

The vaccine preparations for both stocks of virus were prepared from stocks passaged through chicken embryo fibroblast tissue culture cells, at least 8 times, and an additional preparation of 11 tissue culture passages was prepared and tested for 1332-62E1.

The vaccines were administered to newly hatched, specific-antigen free (SPF) chicks by the subcutaneous route. Birds were then challenged at four weeks of age with virulent ILTV challenge virus by the intra-tracheal route and observed for 10 days for the clinical signs of the disease. The incidence of disease in these chicks was compared with controls that either received a commercial recombinant HVT/ILTV vaccine (Innovax®-ILT, from Merck Animal Health) or no vaccine. The Federal Code of Registry (9CFR) requires that at least 80% of the unvaccinated control birds must show clinical signs for a test to be valid, and at least 90% of the vaccinated birds must remain free of clinical signs to be considered to provide satisfactory protection. The results of this study are provided in Table 1 below. Both dual recombinant vaccines provided satisfactory protection against a virulent ILTV challenge.

TABLE 1

Efficacy of Multivalent HVT/NDV/ILTV Vaccine Against a Virulent ILTV Challenge

| Group | Vaccine | Dose* | Clinical Signs** | Mortality** | Clinical and Necropsy Results** | % Protection |
|---|---|---|---|---|---|---|
| 1 | 1332-62.E Pass 8 | 2170 | 1/36 | 1/36 | 1/36 = 2.8% | 97.2% |
| 2 | 1332-62.E Pass 11 | 1409 | 0/36 | 0/36 | 0/36 = 0% | 100% |
| 3 | 1332-70.B Pass 8 | 2483 | 3/36 | 2/36 | 3/36 = 8.3% | 91.7% |
| 4 | Innovax®-ILT | 2200 | 0/24 | 0/24 | 0/24 = 0% | 100% |
| 5a | Challenged Controls | NA | 10/10 | 9/10 | 10/10 = 100% | 0% |
| 5b | Non-challenged Controls | NA | 0/10 | 0/10 | 0/10 | NA |

*Dose is described as plaque forming units (pfu)/0.2 mL dose volume.
**Results are given as the number of positive birds per total number of birds (No. of positive/total).

Example 3

Recombinant HVT/ND/ILTV Vaccine Protects Day-Old Chicks Against Newcastle Disease Virus Challenge Day-old specific-antigen free (SPF) chicks, or 19-day old embryos were vaccinated with a recombinant vaccine, HVT/NDV/ILTV-1332-62E1, tissue culture passage level 11, or a commercial recombinant HVT/NDV vaccine (Innovax®-ND, sold by Merck Animal Health) and then challenged at four weeks of age with virulent Newcastle Disease (ND) challenge virus, Texas-GB strain, by the intra-muscular route. Following a 14-day observation period, where birds were scored for clinical signs of Newcastle disease, the incidence of disease in each group of chicks was compared with unvaccinated controls. The Federal Code of Registry (9CFR) requires that at least 80% of the unvaccinated control birds must show clinical signs for a test to be valid, and at least 90% of the vaccinated birds must remain free of clinical signs for a vaccine to be considered to provide satisfactory protection. The results of this study indicate the recombinant HVT/NDV/ILTV 1332-62E1 vaccine provided satisfactory ND protection by both routes of administration.

TABLE 2

Efficacy of Multivalent HVT/NDV/ILTV Vaccine Against a Virulent NDV Challenge

| Group | Vaccine | Dose* | Route | No. birds | Clinical Signs** | Mortality** | % Protection |
|---|---|---|---|---|---|---|---|
| 1a | 1332-62.E Pass 11 | 2160 | in ovo | 31 | 0/31 = 0% | 0/31 = 0% | 100% |
| 1b | 1332-62.E Pass 11 | 2010 | SC | 31 | 0/31 = 0% | 0/31 = 0% | 100% |
| 2a | Innovax®-ND | 2046 | in ovo | 32 | 3/32 = 9.4% | 2/31 = 6.3% | 90.6% |
| 2b | Innovax®-ND | 1872 | SC | 32 | 1/32 = 3% | 1/32 = 3% | 96.9% |
| 3 | Marek's diluent | NA | SC | 12 | 12/12 = 100% | 12/12 = 100% | 0% |

*Dose is described as plaque forming units (pfu)/dose volume (0.2 mL/SC dose, 0.1 mL/in ovo dose).
**Results are given as the number of positive birds per total number of birds (No. of positive/total).

Example 4

Recombinant HVT/ND/ILTV Vaccine Protects Day-Old Chicks Against Infectious Laryngotracheitis Virus Challenge and Newcastle Disease Virus Challenge A vaccine, HVT/NDV/ILT-1317-46.1-1, was evaluated for efficacy in protecting chickens from either Infectious Laryngotracheitis Virus challenge or Newcastle Disease Virus Challenge. HVT/NDV/ILTV-1317-46.1-1 is an rHVT in which the FC126 HVT backbone comprises the nucleic acid sequence of SEQ ID NO: 16 inserted into the US2 site, and the nucleic acid sequence of SEQ ID NO: 15 inserted into the UL7/8 site, i.e., in between the UL7 and UL8 genes of HVT, (see, Example 1 above). The vaccine preparation was prepared from a stock passaged through chicken embryo fibroblast tissue culture cells 15 times.

The vaccine was administered to newly hatched, specific-antigen free (SPF) chicks by the subcutaneous route. Birds were then challenged at four weeks of age with virulent Infectious Laryngotracheitis (ILT) challenge virus by the intra-tracheal route and observed for 10 days for the clinical signs of the disease, or challenged with virulent Newcastle Disease virus, Texas-GB strain, by the intra-muscular route and observed for 14 days. The incidence of disease in these chicks was compared with controls that either received a commercial recombinant HVT/ILT vaccine, HVT/ND vaccine, or no vaccine. The Federal Code of Registry (9CFR) requires that at least 80% of the unvaccinated control birds must show clinical signs for a test to be valid, and at least 90% of the vaccinated birds must remain free of clinical signs to be considered to provide satisfactory protection. The results of this study are provided in the Table 3 below. The HVT/NDV/ILT vaccine provided satisfactory protection against NDV challenge. Although, in this preliminary study the protection provided by this construct against a virulent ILTV challenge fell just short of the federal requirements, it did provide substantial protection.

TABLE 3

Efficacy of Multivalent HVT/NDV/ILTV Vaccine Against a Virulent NDV and ILTV Challenge

| | | | Results following Challenge | | | |
|---|---|---|---|---|---|---|
| | | | ILT | | NDV | |
| Treatment Group | Dose* | No. Birds | No. Positive/Total** | % Protection | No. Positive/Total** | % Protection |
| HVT/NDV/ILT 1317-46 (p15) | 1356 | 20 | 4/20 = 20% | 80% | 0/19 = 0% | 100% |
| Innovax ®-ILT | 1740 | 20 | 1/20 = 5% | 95% | — | — |
| Innovax ®-ND | 1836 | 20 | — | — | 0/20 = 0% | 100% |
| Placebo | N/A | 10 | 10/10 = 100% | 0% | 8/8 = 100% | 0% |

*Dose is described as plaque forming units (pfu)/0.2 mL dose volume.
**Results are given as the number of positive birds (clinical signs & mortality) per total number of birds (No. of positive/total).

Example 5

Recombinant HVT/ND/ILTV in Combination with 89/03 Bursal Disease in a Vaccine Against an Infectious Bursal Disease Virus Groups of one-day-old chicks (SPF Leghorn) were inoculated with HVT/NDV/ILTV-1332-62E1 combined with IBDV 89/03 vaccine at the time of use. A separate group of chicks were vaccinated with only the IBDV vaccine at 3.5 $\log_{10}$ $TCID_{50}$ per dose. Chickens were challenged at 4 weeks of age with Variant E IBDV challenge. At 10 days post-challenge, birds were euthanized and examined for body/bursa weights and gross lesions consistent with bursal disease. The results were analyzed for acceptability per the applicable 9CFR 113.331 requirements.

IBDV 89/03 is a licensed product used in the poultry industry to protect flocks against both the classical and variant strains of Infectious Bursal Disease virus. The target dose for IBDV 89/03 vaccine was 3.5 $\log_{10}$ $TCID_{50}$ per 0.2 mL dose. The target dose for HVT/NDV/ILT was 3000 PFU per 0.2 mL dose. To achieve the target doses in the final vaccine diluent volume the HVT/NDV/ILTV-1332-62E1 vaccine was diluted to contain 6000 PFU in 0.2 mL, which is double the target dose. The 89/03 vaccine was diluted to contain 3.8 $\log_{10}$ $TCID_{50}$, which is double the target dose. For Group 1 the combination vaccine was prepared by combining equal volumes of the HVT/NDV/ILTV-1332-62E1 vaccine and the 89/03 vaccine. For Group 2, which received only the 89/03 vaccine, an equal volume of diluent was added. One day old chickens in each treatment group received 0.2 mL of the respective vaccine or placebo by the subcutaneous (SC) route (see, Table 4).

TABLE 4

EXPERIMENTAL DESIGN

| | | | | IBDV Variant E | | |
|---|---|---|---|---|---|---|
| | | | Dose | Challenge | | |
| Group | No. | Vaccine | HVT-(89/03) | Age | # birds | Necropsy |
| 1 | 45 | HVT/NDV/ILT + 89/03 | 3000 – (3.5 $\log_{10}$ $TCID_{50}$) | 4 wks | ≥40 | 10 day post-challenge |
| 2 | 45 | 89/03 | NA – (3.5 $\log_{10}$ $TCID_{50}$) | 4 wks | ≥40 | 10 day post-challenge |
| 3 | 45 | Placebo challenged controls | — | 4 wks | ≥40 | 10 day post-challenge |
| 4 | 30 | Placebo non-challenged controls | — | — | ≥25 | 10 day post-challenge |

At hatch, chicks in each of the vaccine treatment groups were tagged with a set of randomized tag numbers assigned using the randomization program of EXCEL. In addition, birds removed from each pen at 7 days post-challenge for histological examination of bursas were randomly determined using the randomization program of EXCEL.

The chickens were challenged at four weeks of age with IBDV-Variant E challenge virus. Each chicken received 0.06 mL containing approximately $10^{2.2}$ $EID_{50}$ per dose via the eyedrop route. At seven days post-challenge, 6-9 birds from each group were removed for histological evaluation of individual bursae (see, Table 5). Bursa samples were collected from each challenged chicken using care to collect tissue which had not been crushed or squeezed by the forceps. The tissue sample was placed in an individual container of 10% formalin.

Bursa from each chicken challenged with IBD-Var E virus was recorded as negative or positive for bursal atrophy, gross macroscopic lesions and/or lymphocyte depletion as determined by histological examination. Bursal lesions included macroscopic hemorrhage, edema/exudates, cream/yellow color, striations, or gross atrophy. Bursal atrophy was measured by individually weighing each chicken to the nearest gram. Bursae were individually weighed to the nearest hundredth of a gram. Bursa/body weight ratios were computed for each bird employing the formula, BW ratio: (Bursa Weight÷Body Weight)×1000. A bursa to body weight ratio of more than 2 standard deviations from the challenged control is considered negative for and protective from infectious bursal disease. The results of this study showed that vaccine treatment Groups 1 and 2 were negative for IBD (i.e., not statistically different from the placebo non-challenged control) indicating that both vaccines were efficacious and further demonstrating that there was no interference of the protection provided by the 89/03 strain of the vaccine against the IBDV challenge due to the recombinant HVT/NDV/ILT construct also being present in the multivalent vaccine (see, Table 5).

TABLE 5

Day 7 NECROPSY DATA FOR IBDV VARIANT E CHALLENGE

| Group | No. | Vaccine | Average Bursa BW ratio |
|---|---|---|---|
| 1 | 9 | HVT/NDV/ILT + 89/03 | 5.464 |
| 2 | 9 | 89/03 | 5.715 |
| 3 | 9 | placebo challenged controls | 1.874 (SD + 0.641)** |
| 4 | 6 | placebo non-challenged controls | 5.838 |

**2 SD from Control is statistically different.

Example 6

Sequences

The following sequences have been used in the exemplary rHVT constructs. The coding sequences provided below include individual stop codons, which can be readily replaced with alternative stop codons without modifying the properties of the protein antigens that the coding sequences encode.

```
ILTV gD Glycoprotein, coding sequence (SEQ ID NO: 1)
ATGCACCGTCCTCATCTCAGACGGCACTCGCGTTACTACGCGAAAGGAGAGGTGCTTAACAAACACAT

GGATTGCGGTGGAAAACGGTGCTGCTCAGGCGCAGCTGTATTCACTCTTTTCTGGACTTGTGTCAGGA

TTATGCGGGAGCATATCTGCTTTGTACGCAACGCTATGGACCGCCATTTATTTTTGAGGAATGCTTTT

TGGACTATCGTACTGCTTTCTTCCTTCGCTAGCCAGAGCACCGCCGCCGTCACGTACGACTACATTTT

AGGCCGTCGCGCGCTCGACGCGCTAACCATACCGGCGGTTGGCCCGTATAACAGATACCTCACTAGGG

TATCAAGAGGCTGCGACGTTGTCGAGCTCAACCCGATTTCTAACGTGGACGACATGATATCGGCGGCC

AAAGAAAAAGAGAAGGGGGGCCCTTTCGAGGCCTCCGTCGTCTGGTTCTACGTGATTAAGGGCGACGA

CGGCGAGGACAAGTACTGTCCAATCTATAGAAAAGAGTACAGGGAATGTGGCGACGTACAACTGCTAT

CTGAATGCGCCGTTCAATCTGCACAGATGTGGGCAGTGGACTATGTTCCTAGCACCCTTGTATCGCGA

AATGGCGCGGGACTGACTATATTCTCCCCCACTGCTGCGCTCTCTGGCCAATACTTGCTGACCCTGAA

AATCGGGAGATTTGCGCAAACAGCTCTCGTAACTCTAGAAGTTAACGATCGCTGTTTAAAGATCGGGT

CGCAGCTTAACTTTTTACCGTCGAAATGCTGGACAACAGAACAGTATCAGACTGGATTTCAAGGCGAA

CACCTTTATCCGATCGCAGACACCAATACACGACACGCGGACGACGTATATCGGGGATACGAAGATAT

TCTGCAGCGCTGGAATAATTTGCTGAGGAAAAAGAATCCTAGCGCGCCAGACCCTCGTCCAGATAGCG

TCCCGCAAGAAATTCCCGCTGTAACCAAGAAAGCGGAAGGGCGCACCCCGGACGCAGAAAGCAGCGAA

AAGAAGGCCCCTCCAGAAGACTCGGAGGACGACATGCAGGCAGAGGCTTCTGGAGAAAATCCTGCCGC

CCTCCCCGAAGACGACGAAGTCCCCGAGGACACCGAGCACGATGATCCAAACTCGGATCCTGACTATT

ACAATGACATGCCCGCCGTGATCCCGGTGGAGGAGACTACTAAAAGTTCTAATGCCGTCTCCATGCCC

ATATTCGCGGCGTTCGTAGCCTGCGCGGTCGCGCTCGTGGGGCTACTGGTTTGGAGCATCGTAAAATG

CGCGCGTAGCTAA

ILTV gD Glycoprotein (SEQ ID NO: 2)
MHRPHLRRHSRYYAKGEVLNKHMDCGGKRCCSGAAVFTLFWTCVRIMREHICFVRNAMDRHLFLRNAF

WTIVLLSSFASQSTAAVTYDYILGRRALDALTIPAVGPYNRYLTRVSRGCDVVELNPISNVDDMISAA

KEKEKGGPFEASVVWFYVIKGDDGEDKYCPIYRKEYRECGDVQLLSECAVQSAQMWAVDYVPSTLVSR

NGAGLTIFSPTAALSGQYLLTLKIGRFAQTALVTLEVNDRCLKIGSQLNFLPSKCWTTEQYQTGFQGE

HLYPIADTNTRHADDVYRGYEDILQRWNNLLRKKNPSAPDPRPDSVPQEIPAVTKKAEGRTPDAESSE

KKAPPEDSEDDMQAEASGENPAALPEDDEVPEDTEHDDPNSDPDYYNDMPAVIPVEETTKSSNAVSMP

IFAAFVACAVALVGLLVWSIVKCARS
```

ILTV gI Glycoprotein, coding sequence (SEQ ID NO: 3)
ATGGCATCGCTACTTGGAACTCTGGCTCTCCTTGCCGCGACGCTCGCACCCTTCGGCGCGATGGGAAT

CGTGATCACTGGAAATCACGTCTCCGCCAGGATTGACGACGATCACATCGTGATCGTCGCGCCTCGCC

CCGAAGCTACAATTCAACTGCAGCTATTTTTCATGCCTGGCCAGAGACCCCACAAACCCTACTCAGGA

ACCGTCCGCGTCGCGTTTCGGTCTGATATAACAAACCAGTGCTACCAGGAACTTAGCGAGGAGCGCTT

TGAAAATTGCACTCATCGATCGTCTTCTGTTTTTGTCGGCTGTAAAGTGACCGAGTACACGTTCTCCG

CCTCGAACAGACTAACCGGACCTCCACACCCGTTTAAGCTCACTATACGAAATCCTCGTCCGAACGAC

AGCGGGATGTTCTACGTAATTGTTCGGCTAGACGACACCAAAGAACCCATTGACGTCTTCGCGATCCA

ACTATCGGTGTATCAATTCGCGAACACCGCCGCGACTCGCGGACTCTATTCCAAGGCTTCGTGTCGCA

CCTTCGGATTACCTACCGTCCAACTTGAGGCCTATCTCAGGACCGAGGAAAGTTGGCGCAACTGGCAA

GCGTACGTTGCCACGGAGGCCACGACGACCAGCGCCGAGGCGACAACCCCGACGCCCGTCACTGCAAC

CAGCGCCTCCGAACTTGAAGCGGAACACTTTACCTTTCCCTGGCTAGAAAATGGCGTGGATCATTACG

AACCGACACCCGCAAACGAAAATTCAAACGTTACTGTCCGTCTCGGGACAATGAGCCCTACGCTAATT

GGGGTAACCGTGGCTGCCGTCGTGAGCGCAACGATCGGCCTCGTCATTGTAATTTCCATCGTCACCAG

AAACATGTGCACCCCGCACCGAAAATTAGACACGGTCTCGCAAGACGACGAAGAACGTTCCCAAACTA

GAAGGGAATCGCGAAAATTTGGACCCATGGTTGCGTGCGAAATAAACAAGGGGGCTGACCAGGATAGT

GAACTTGTGGAACTGGTTGCGATTGTTAACCCGTCTGCGCTAAGCTCGCCCGACTCAATAAAAATGTG

A

ILTV gI Glycoprotein (SEQ ID NO: 4)
MASLLGTLALLAATLAPFGAMGIVITGNHVSARIDDDHIVIVAPRPEATIQLQLFFMPGQRPHKPYSG

TVRVAFRSDITNQCYQELSEERFENCTHRSSSVFVGCKVTEYTFSASNRLTGPPHPFKLTIRNPRPND

SGMFYVIVRLDDTKEPIDVFAIQLSVYQFANTAATRGLYSKASCRTFGLPTVQLEAYLRTEESWRNWQ

AYVATEATTTSAEATTPTPVTATSASELEAEHFTFPWLENGVDHYEPTPANENSNVTVRLGTMSPTLI

GVTVAAVVSATIGLVIVISIVTRNMCTPHRKLDTVSQDDEERSQTRRESRKFGPMVACEINKGADQDS

ELVELVAIVNPSALSSPDSIKM

NDV F Protein, coding sequence (SEQ ID NO: 5): Clone 30
ATGGGCCCCAGACCTTCTACCAAGAACCCAGTACCTATGATGCTGACTGTCCGAGTCGCGCTGGTACT

GAGTTGCATCTGTCCGGCAAACTCCATTGATGGCAGGCCTCTTGCGGCTGCAGGAATTGTGGTTACAG

GAGACAAAGCCGTCAACATATACACCTCATCCCAGACAGGATCAATCATAGTTAAGCTCCTCCCGAAT

CTGCCCAAGGATAAGGAGGCATGTGCGAAAGCCCCCTTGGATGCATACAACAGGACATTGACCACTTT

GCTCACCCCCCTTGGTGACTCTATCCGTAGGATACAAGAGTCTGTGACTACATCTGGAGGGGGGAGAC

AGGGGCGCCTTATAGGCGCCATTATTGGCGGTGTGGCTCTTGGGGTTGCAACTGCCGCACAAATAACA

GCGGCCGCAGCTCTGATACAAGCCAAACAAAATGCTGCCAACATCCTCCGACTTAAAGAGAGCATTGC

CGCAACCAATGAGGCTGTGCATGAGGTCACTGACGGATTATCGCAACTAGCAGTGGCAGTTGGGAAGA

TGCAGCAGTTTGTTAATGACCAATTTAATAAAACAGCTCAGGAATTAGACTGCATCAAAATTGCACAG

CAAGTTGGTGTAGAGCTCAACCTGTACCTAACCGAATTGACTACAGTATTCGGACCACAAATCACTTC

ACCTGCTTTAAACAAGCTGACTATTCAGGCACTTTACAATCTAGCTGGTGGAAATATGGATTACTTAT

TGACTAAGTTAGGTGTAGGGAACAATCAACTCAGCTCATTAATCGGTAGCGGCTTAATCACCGGTAAC

CCTATTCTATACGACTCACAGACTCAACTCTTGGGTATACAGGTAACTCTACCTTCAGTCGGGAAGCT

AAATAATATGCGTGCCACCTACTTGGAAACCTTATCCGTAAGCACAACCAGGGGATTTGCCTCGGCAC

TTGTCCCAAAAGTGGTGACACAGGTCGGTTCTGTGATAGAAGAACTTGACACCTCATACTGTATAGAA

ACTGACTTACATTTATATTGTACAAGAATAGTAACGTTCCCTATGTCCCCTGGTATTTATTCCTGCTT

-continued
GAGCGGCAATACGTCGGCCTGTATGTACTCAAAGACCGAAGGCGCACTTACTACACCATACATGACTA

TCAAAGGTTCAGTCATCGCCAACTGCAAGATGACAACATGTAGATGTGTAAACCCCCCGGGTATCATA

TCGCAAAACTATGGAGAAGCCGTGTCTCTAATAGATAAACAATCATGCAATGTTTTATCCTTAGGCGG

GATAACTTTAAGGCTCAGTGGGGAATTCGATGTAACTTATCAGAAGAATATCTCAATACAAGATTCTC

AAGTAATAATAACAGGCAATCTTGATATCTCAACTGAGCTTGGGAATGTCAACAACTCGATCAGTAAT

GCTTTGAATAAGTTAGAGGAAAGCAACAGAAAACTAGACAAAGTCAATGTCAAACTGACTAGCACATC

TGCTCTCATTACCTATATCGTGTTGACTATCATATCTCTTGTTTTTGGTATACTTAGCCTGATTCTAG

CATGCTACCTAATGTACAAGCAAAAGGCGCAACAAAAGACCTTATTATGGCTTGGGAATAATACTCTA

GATCAGATGAGAGCCACTACAAAAATGTGA

NDV F Protein (SEQ ID NO: 6): Clone 30
MGPRPSTKNPVPMMLTVRVALVLSCICPANSIDGRPLAAAGIVVTGDKAVNIYTSSQTGSIIVKLLPN

LPKDKEACAKAPLDAYNRTLTTLLTPLGDSIRRIQESVTTSGGGRQGRLIGAIIGGVALGVATAAQIT

AAAALIQAKQNAANILRLKESIAATNEAVHEVTDGLSQLAVAVGKMQQFVNDQFNKTAQELDCIKIAQ

QVGVELNLYLTELTTVFGPQITSPALNKLTIQALYNLAGGNMDYLLTKLGVGNNQLSSLIGSGLITGN

PILYDSQTQLLGIQVTLPSVGKLNNMRATYLETLSVSTTRGFASALVPKVVTQVGSVIEELDTSYCIE

TDLHLYCTRIVTFPMSPGIYSCLSGNTSACMYSKTEGALTTPYMTIKGSVIANCKMTTCRCVNPPGII

SQNYGEAVSLIDKQSCNVLSLGGITLRLSGEFDVTYQKNISIQDSQVIITGNLDISTELGNVNNSISN

ALNKLEESNRKLDKVNVKLTSTSALITYIVLTIISLVFGILSLILACYLMYKQKAQQKTLLWLGNNTL

DQMRATTKM

NDV F Protein, coding sequence (SEQ ID NO: 7): (B1 Hitchner)
ATGGATCGATCCCGGTTGGCGCCCTCCAGGTGCAGGATGGGCTCCAGACCTTCTACCAAGAACCCAGC

ACCTATGATGCTGACTATCCGGGTCGCGCTGGTACTGAGTTGCATCTGTCCGGCAAACTCCATTGATG

GCAGGCCTCTTGCAGCTGCAGGAATTGTGGTTACAGGAGACAAAGCAGTCAACATATACACCTCATCC

CAGACAGGATCAATCATAGTTAAGCTCCTCCCGAATCTGCCAAAGGATAAGGAGGCATGTGCGAAAGC

CCCCTTGGATGCATACAACAGGACATTGACCACTTTGCTCACCCCCCTTGGTGACTCTATCCGTAGGA

TACAAGAGTCTGTGACTACATCTGGAGGGGGGAGACAGGGGCGCCTTATAGGCGCCATTATTGGCGGT

GTGGCTCTTGGGGTTGCAACTGCCGCACAAATAACAGCGGCCGCAGCTCTGATACAAGCCAAACAAAA

TGCTGCCAACATCCTCCGACTTAAAGAGAGCATTGCCGCAACCAATGAGGCTGTGCATGAGGTCACTG

ACGGATTATCGCAACTAGCAGTGGCAGTTGGGAAGATGCAGCAGTTCGTTAATGACCAATTTAATAAA

ACAGCTCAGGAATTAGACTGCATCAAAATTGCACAGCAAGTTGGTGTAGAGCTCAACCTGTACCTAAC

CGAATCGACTACAGTATTCGGACCACAAATCACTTCACCTGCCTTAAACAAGCTGACTATTCAGGCAC

TTTACAATCTAGCTGGTGGGAATATGGATTACTTATTGACTAAGTTAGGTATAGGGAACAATCAACTC

AGCTCATTAATCGGTAGCGGCTTAATCACCGGTAACCCTATTCTATACGACTCACAGACTCAACTCTT

GGGTATACAGGTAACTCTACCTTCAGTCGGGAACCTAAATAATATGCGTGCCACCTACTTGGAAACCT

TATCCGTAAGCACAACCAGGGGATTTGCCTCGGCACTTGTCCCAAAAGTGGTGACACGGGTCGGTTCT

GTGATAGAAGAACTTGACACCTCATACTGTATAGAAACTGACTTAGATTTATATTGTACAAGAATAGT

AACGTTCCCTATGTCCCCTGGTATTTACTCCTGCTTGAGCGGCAATACATCGGCCTGTATGTACTCAA

AGACCGAAGGCGCACTTACTACACCATATATGACTATCAAAGGCTCAGTCATCGCTAACTGCAAGATG

ACAACATGTAGATGTGTAAACCCCCCGGGTATCATATCGCAAAACTATGGAGAAGCCGTGTCTCTAAT

AGATAAACAATCATGCAATGTTTTATCCTTAGGCGGGATAACTTTAAGGCTCAGTGGGGAATTCGATG

TAACTTATCAGAAGAATATCTCAATACAAGATTCTCAAGTAATAATAACAGGCAATCTTGATATCTCA

ACTGAGCTTGGGAATGTCAACAACTCGATCAGTAATGCCTTGAATAAGTTAGAGGAAAGCAACAGAAA

-continued

ACTAGACAAAGTCAATGTCAAACTGACCAGCACATCTGCTCTCATTACCTATATCGTTTTGACTATCA

TATCTCTTGTTTTTGGTATACTTAGCCTGATTCTAGCATGCTACCTAATGTACAAGCAAAAGGCGCAA

CAAAAGACCTTATTATGGCTTGGGAATAATACCCTAGATCAGATGAGAGCCACTACAAAAATGTGA

NDV F Protein (SEQ ID NO: 8): (B1 Hitchner)
MDRSRLAPSRCRMGSRPSTKNPAPMMLTIRVALVLSCICPANSIDGRPLAAAGIVVTGDKAVNIYTSS

QTGSIIVKLLPNLPKDKEACAKAPLDAYNRTLTTLLTPLGDSIRRIQESVTTSGGGRQGRLIGAIIGG

VALGVATAAQITAAAALIQAKQNAANILRLKESIAATNEAVHEVTDGLSQLAVAVGKMQQFVNDQFNK

TAQELDCIKIAQQVGVELNLYLTESTTVFGPQITSPALNKLTIQALYNLAGGNMDYLLTKLGIGNNQL

SSLIGSGLITGNPILYDSQTQLLGIQVTLPSVGNLNNMRATYLETLSVSTTRGFASALVPKVVTRVGS

VIEELDTSYCIETDLDLYCTRIVTFPMSPGIYSCLSGNTSACMYSKTEGALTTPYMTIKGSVIANCKM

TTCRCVNPPGIISQNYGEAVSLIDKQSCNVLSLGGITLRLSGEFDVTYQKNISIQDSQVIITGNLDIS

TELGNVNNSISNALNKLEESNRKLDKVNVKLTSTSALITYIVLTIISLVFGILSLILACYLMYKQKAQ

QKTLLWLGNNTLDQMRATTKM

ILTV gD Promoter (SEQ ID NO: 9)
AAACAGCTGTACTACAGAGTAACCGATGGAAGAACATCGGTCCAGCTAATGTGCCTGTCGTGCACGAG

CCATTCTCCGGAACCTTACTGTCTTTTCGACACGTCTCTTATAGCGAGGGAAAAAGATATCGCGCCAG

AGTTATACTTTACCTCTGATCCGCAAACGGCATACTGCACAATAACTCTGCCGTCCGGCGTTGTTCCG

AGATTCGAATGGAGCCTTAATAATGTTTCACTGCCGGAATATTTGACGGCCACGACCGTTGTTTCGCA

TACCGCTGGCCAAAGTACAGTGTGGAAGAGCAGCGCGAGAGCAGGCGAGGCGTGGATTTCTGGCCGGG

GAGGCAATATATACGAATGCACCGTCCTCATCTCAGACGGCACTCGCGTTACTACGCGAAAGGAGAGG

TGCTTAACAAACACATGGATTGCGGTGGAAAACGGTGCTGCTCAGGCGCAGCTGTATTCACTCTTTTC

TGGACTTGTGTCAGGATTATGCGGGAGCATATCTGCTTTGTACGCAACGCT

ILTV gI Promoter (SEQ ID NO: 10)
TGACTATTACAATGACATGCCCGCCGTGATCCCGGTGGAGGAGACTACTAAAAGTTCTAATGCCGTCT

CCATGCCCATATTCGCGGCGTTCGTAGCCTGCGCGGTCGCGCTCGTGGGGCTACTGGTTTGGAGCATC

GTAAAATGCGCGCGTAGCTAATCGAGCCTAGAATAGGTGGTTTCTTCCTACATGCCACGCCTCACGCT

CATAATATAAATCACATGGAATAGCATACCAATGCCTATTCATTGGGACGTTCGAAAAGC hCMV IE Promoter (SEQ ID NO: 11): (Truncated)
CGCGCCAGGTCAATTCCCTGGCATTATGCCCAGTACATGACCTTATGGGACTTTCCTACTTGGCAGTA

CATCTACGTATTAGTCATCGCTATTACCATGGTGATGCGGTTTTGGCAGTACATCAATGGGCGTGGAT

AGCGGTTTGACTCACGGGGATTTCCAAGTCTCCACCCCATTGACGTCAATGGGAGTTTGTTTTGGCAC

CAAAATCAACGGGACTTTCCAAAATGTCGTAACAACTCCGCCCCATTGACGCAAATGGGCGGTAGCGT

GTACGGTGGGAGGTCTATATAAGCAGAGCTCGTTTAGTGAACCGTCAGATCGCCTGGAGACGCCATCC

ACGCTGTTTTGACCTCCATA hCMV IE Promoter (SEQ ID NO: 12): (Towne Strain)
GTGAATAATAAAATGTGTGTTTGTCCGAAATACGCGTTTGAGATTTCTGTCCCGACTAAATTCATGTC

GCGCGATAGTGGTGTTTATCGCCGATAGAGATGGCGATATTGGAAAAATCGATATTTGAAAATATGGC

ATATTGAAAATGTCGCCGATGTGAGTTTCTGTGTAACTGATATCGCCATTTTTCCAAAAGTTGATTTT

TGGGCATACGCGATATCTGGCGATACGCTTATATCGTTTACGGGGGATGGCGATAGACGCCTTTGGTG

ACTTGGGCGATTCTGTGTGTCGCAAATATCGCAGTTTCGATATAGGTGACAGACGATATGAGGCTATA

TCGCCGATAGAGGCGACATCAAGCTGGCACATGGCCAATGCATATCGATCTATACATTGAATCAATAT

TGGCCATTAGCCATATTATTCATTGGTTATATAGCATAAATCAATATTGGCTATTGGCCATTGCATAC

GTTGTATCCATATCATAATATGTACATTTATATTGGCTCATGTCCAACATTACCGCCATGTTGACATT

-continued

GATTATTGACTAGTTATTAATAGTAATCAATTACGGGGTCATTAGTTCATAGCCCATATATGGAGTTC
CGCGTTACATAACTTACGGTAAATGGCCCGCCTGGCTGACCGCCCAACGACCCCCGCCCATTGACGTC
AATAATGACGTATGTTCCCATAGTAACGCCAATAGGGACTTTCCATTGACGTCAATGGGTGGAGTATT
TACGGTAAACTGCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTTCCTACTTGGCA
GTACATCTACGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAGTTTGTTTTGG
CACCAAAATCAACGGGACTTTCCAAAATGTCGTAACAACTCCGCCCCATTGACGCAAATGGGCGGTAG
GCGTGTACGGTGGGAGGTCTATATAAGCAGAGCTCGTTTAGTGAACCGTCAGATCGCCTGGAGACGCC
ATCCACGCTGTTTTGACCTCCATAGAAGACACCGG

Synthetic Polyadenylation Signal (SEQ ID NO: 13)
GGAATTCTAGATCCCACGTCACTATTGTATACTCTATATTATACTCTATGTTATACTCTGTAATCCTA
CTCAATAAACGTGTCACGCCTGTGAAACCGTACTAAGTCTCCCGTGTCTTCTTATCACCATCAGGTGA
CATCCTCGCCCAGGCTGTCAATCATGCCGGTATCGATTCCAGTAGCACCGGCCCCACGCTGACAACCC
ACTCTTGCAGCGTTAGCAGCGCCCCTCTTAACAAGCCGACCCCCACCAGCGTCGCGGTTACTAACACT

CCTCTCCCC

HSV TK polyadenylation signal (SEQ ID NO: 14)
GGGAGATGGGGGAGGCTAACTGAAACACGGAAGGAGACAATACCGGAAGGAACCCGCGCTATGACGGC
AATAAAAAGACAGAATAAAACGCACGGGTGTTGGGTCGTTTGTTCATAAACGCGGGGTTCGGTCCCAG
GGCTGGCACTCTGTCGATACCCCACCGAGACCCCATTGGGACCAATACGCCCGCGTTTCTTCCTTTTC
CCCACCCCAACCCCCAAGTTCGGGTGAAGGCCCAGGGCTCGCAGCCAACGTCGGGGCGGCAAGCCCTG
CCATAGCCACGGGCCCCGTGGGTTAGGGACGGGGTCCCCCATGGGGAATGGTTTATGGTTCGTGGGGG
TTATTATTTTGGGCGTTGCGTGGGGTCAGGTCCACGACTGGACTGAGCAGACAGACCCATGGTTTTTG
GATGGCCTGGGCATGGACCGCATGTACTGGCGCGACACGAACACCGGGCGTCTGTGGCTGCCAAACAC

CCCCGACCCCCAAAAACCACCGCGCGGATTTCTGGCGCCGCCGGACG

IE-NDV F Cassette Insert (1317-46 virus) (SEQ ID NO: 15): (3593 bp)
TAATTAACCCGGGAAGCTTGCATGCCTGCAGTGAATAATAAAATGTGTGTTTGTCCGAAATACGCGTT

TGAGATTTCTGTCCCGACTAAATTCATGTCGCGCGATAGTGGTGTTTATCGCCGATAGAGATGGCGAT

ATTGGAAAAATCGATATTTGAAAATATGGCATATTGAAAATGTCGCCGATGTGAGTTTCTGTGTAACT

GATATCGCCATTTTTCCAAAAGTTGATTTTTGGGCATACGCGATATCTGGCGATACGCTTATATCGTT

TACGGGGGATGGCGATAGACGCCTTTGGTGACTTGGGCGATTCTGTGTGTCGCAAATATCGCAGTTTC

GATATAGGTGACAGACGATATGAGGCTATATCGCCGATAGAGGCGACATCAAGCTGGCACATGGCCAA

TGCATATCGATCTATACATTGAATCAATATTGGCCATTAGCCATATTATTCATTGGTTATATAGCATA

AATCAATATTGGCTATTGGCCATTGCATACGTTGTATCCATATCATAATATGTACATTTATATTGGCT

CATGTCCAACATTACCGCCATGTTGACATTGATTATTGACTAGTTATTAATAGTAATCAATTACGGGG

TCATTAGTTCATAGCCCATATATGGAGTTCCGCGTTACATAACTTACGGTAAATGGCCCGCCTGGCTG

ACCGCCCAACGACCCCCGCCCATTGACGTCAATAATGACGTATGTTCCCATAGTAACGCCAATAGGGA

CTTTCCATTGACGTCAATGGGTGGAGTATTTACGGTAAACTGCCCACTTGGCAGTACATCAAGTGTAT

CATATGCCAAGTACGCCCCCTATTGACGTCAATGACGGTAAATGGCCCGCCTGGCATTATGCCCAGTA

CATGACCTTATGGGACTTTCCTACTTGGCAGTACATCTACGTATTAGTCATCGCTATTACCATGGTGA

TGCGGTTTTGGCAGTACATCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAAAATGTCGTAACAA

-continued

```
CTCCGCCCCATTGACGCAAATGGGCGGTAGGCGTGTACGGTGGGAGGTCTATATAAGCAGAGCTCGTT

TAGTGAACCGTCAGATCGCCTGGAGACGCCATCCACGCTGTTTTGACCTCCATAGAAGACACCGGGAC

CATGGATCGATCCCGGTTGGCGCCCTCCAGGTGCAGGATGGGCTCCAGACCTTCTACCAAGAACCCAG

CACCTATGATGCTGACTATCCGGGTCGCGCTGGTACTGAGTTGCATCTGTCCGGCAAACTCCATTGAT

GGCAGGCCTCTTGCAGCTGCAGGAATTGTGGTTACAGGAGACAAAGCAGTCAACATATACACCTCATC

CCAGACAGGATCAATCATAGTTAAGCTCCTCCCGAATCTGCCAAAGGATAAGGAGGCATGTGCGAAAG

CCCCCTTGGATGCATACAACAGGACATTGACCACTTTGCTCACCCCCCTTGGTGACTCTATCCGTAGG

ATACAAGAGTCTGTGACTACATCTGGAGGGGGAGACAGGGGCGCCTTATAGGCGCCATTATTGGCGG

TGTGGCTCTTGGGGTTGCAACTGCCGCACAAATAACAGCGGCCGCAGCTCTGATACAAGCCAAACAAA

ATGCTGCCAACATCCTCCGACTTAAAGAGAGCATTGCCGCAACCAATGAGGCTGTGCATGAGGTCACT

GACGGATTATCGCAACTAGCAGTGGCAGTTGGGAAGATGCAGCAGTTCGTTAATGACCAATTTAATAA

AACAGCTCAGGAATTAGACTGCATCAAAATTGCACAGCAAGTTGGTGTAGAGCTCAACCTGTACCTAA

CCGAATCGACTACAGTATTCGGACCACAAATCACTTCACCTGCCTTAAACAAGCTGACTATTCAGGCA

CTTTACAATCTAGCTGGTGGGAATATGGATTACTTATTGACTAAGTTAGGTATAGGGAACAATCAACT

CAGCTCATTAATCGGTAGCGGCTTAATCACCGGTAACCCTATTCTATACGACTCACAGACTCAACTCT

TGGGTATACAGGTAACTCTACCTTCAGTCGGGAACCTAAATAATATGCGTGCCACCTACTTGGAAACC

TTATCCGTAAGCACAACCAGGGGATTTGCCTCGGCACTTGTCCCAAAAGTGGTGACACGGGTCGGTTC

TGTGATAGAAGAACTTGACACCTCATACTGTATAGAAACTGACTTAGATTTATATTGTACAAGAATAG

TAACGTTCCCTATGTCCCCTGGTATTTACTCCTGCTTGAGCGGCAATACATCGGCCTGTATGTACTCA

AAGACCGAAGGCGCACTTACTACACCATATATGACTATCAAAGGCTCAGTCATCGCTAACTGCAAGAT

GACAACATGTAGATGTGTAAACCCCCCGGGTATCATATCGCAAACTATGGAGAAGCCGTGTCTCTAA

TAGATAAACAATCATGCAATGTTTTATCCTTAGGCGGGATAACTTTAAGGCTCAGTGGGGAATTCGAT

GTAACTTATCAGAAGAATATCTCAATACAAGATTCTCAAGTAATAATAACAGGCAATCTTGATATCTC

AACTGAGCTTGGGAATGTCAACAACTCGATCAGTAATGCCTTGAATAAGTTAGAGGAAAGCAACAGAA

AACTAGACAAAGTCAATGTCAAACTGACCAGCACATCTGCTCTCATTACCTATATCGTTTTGACTATC

ATATCTCTTGTTTTTGGTATACTTAGCCTGATTCTAGCATGCTACCTAATGTACAAGCAAAAGGCGCA

ACAAAAGACCTTATTATGGCTTGGGAATAATACCCTAGATCAGATGAGAGCCACTACAAAAATGTGAA

CACAGATGAGGAACGAAGGTTTCCCTAATAGTAATTTGTGTGAAAGTTCTGGTAGTCTGTCAGTTCGG

AGAGTTAAGAAAAAAAAAAACCCCCCCCCCCCCCCCCCCCCCTGGGTACGATCCTCTAGAGTC

GGGAGATGGGGGAGGCTAACTGAAACACGGAAGGAGACAATACCGGAAGGAACCCGCGCTATGACGGC

AATAAAAAGACAGAATAAAACGCACGGGTGTTGGGTCGTTTGTTCATAAACGCGGGGTTCGGTCCCAG

GGCTGGCACTCTGTCGATACCCCACCGAGACCCCATTGGGACCAATACGCCCGCGTTTCTTCCTTTTC

CCCACCCCAACCCCCAAGTTCGGGTGAAGGCCCAGGGCTCGCAGCCAACGTCGGGGCGGCAAGCCCTG

CCATAGCCACGGGCCCCGTGGGTTAGGGACGGGGTCCCCCATGGGGAATGGTTTATGGTTCGTGGGGG

TTATTATTTTGGGCGTTGCGTGGGGTCAGGTCCACGACTGGACTGAGCAGACAGACCCATGGTTTTTG

GATGGCCTGGGCATGGACCGCATGTACTGGCGCGACACGAACACCGGGCGTCTGTGGCTGCCAAACAC

CCCCGACCCCCAAAAACCACCGCGCGGATTTCTGGCGCCGCCGGACGTCGACTTAAT

ILTV insert sequence (SEQ ID NO: 16) (3563 bp SalI - HindIII fragment):
gTCGACGGCAGAGTCGCAGACGCCCCTATTGGACGTCAAAATTGTAGAGGTGAAGTTTTCAAACGATG

GCGAAGTAACGGCGACTTGCGTTTCCACCGTCAAATCTCCCTATAGGGTAGAAACTAATTGGAAAGTA

GACCTCGTAGATGTAATGGATGAAATTTCTGGGAACAGTCCCGCCGGGGTTTTTAACAGTAATGAGAA
```

-continued

ATGGCAGAAACAGCTGTACTACAGAGTAACCGATGGAAGAACATCGGTCCAGCTAATGTGCCTGTCGT
GCACGAGCCATTCTCCGGAACCTTACTGTCTTTTCGACACGTCTCTTATAGCGAGGGAAAAAGATATC
GCGCCAGAGTTATACTTTACCTCTGATCCGCAAACGGCATACTGCACAATAACTCTGCCGTCCGGCGT
TGTTCCGAGATTCGAATGGAGCCTTAATAATGTTTCACTGCCGGAATATTTGACGGCCACGACCGTTG
TTTCGCATACCGCTGGCCAAAGTACAGTGTGGAAGAGCAGCGCGAGAGCAGGCGAGGCGTGGATTTCT
GGCCGGGGAGGCAATATATACGAATGCACCGTCCTCATCTCAGACGGCACTCGCGTTACTACGCGAAA
GGAGAGGTGCTTAACAAACACATGGATTGCGGTGGAAAACGGTGCTGCTCAGGCGCAGCTGTATTCAC
TCTTTTCTGGACTTGTGTCAGGATTATGCGGGAGCATATCTGCTTTGTACGAACGCTATGGACCGCC
ATTTATTTTGAGGAATGCTTTTTGGACTATCGTACTGCTTTCTTCCTTCGCTAGCCAGAGCACCGCC
GCCGTCACGTACGACTACATTTTAGGCCGTCGCGCGCTCGACGCGCTAACCATACCGGCGGTTGGCCC
GTATAACAGATACCTCACTAGGGTATCAAGAGGCTGCGACGTTGTCGAGCTCAACCCGATTTCTAACG
TGGACGACATGATATCGGCGGCCAAAGAAAAAGAGAAGGGGGGCCCTTTCGAGGCCTCCGTCGTCTGG
TTCTACGTGATTAAGGGCGACGACGGCGAGGACAAGTACTGTCCAATCTATAGAAAAGAGTACAGGGA
ATGTGGCGACGTACAACTGCTATCTGAATGCGCCGTTCAATCTGCACAGATGTGGGCAGTGGACTATG
TTCCTAGCACCCTTGTATCGCGAAATGGCGCGGGACTGACTATATTCTCCCCCACTGCTGCGCTCTCT
GGCCAATACTTGCTGACCCTGAAAATCGGGAGATTTGCGCAAACAGCTCTCGTAACTCTAGAAGTTAA
CGATCGCTGTTTAAAGATCGGGTCGCAGCTTAACTTTTTACCGTCGAAATGCTGGACAACAGAACAGT
ATCAGACTGGATTTCAAGGCGAACACCTTTATCCGATCGCAGACACCAATACACGACACGCGGACGAC
GTATATCGGGGATACGAAGATATTCTGCAGCGCTGGAATAATTTGCTGAGGAAAAAGAATCCTAGCGC
GCCAGACCCTCGTCCAGATAGCGTCCCGCAAGAAATTCCCGCTGTAACCAAGAAAGCGGAAGGGCGCA
CCCCGGACGCAGAAAGCAGCGAAAAGAAGGCCCCTCCAGAAGACTCGGAGGACGACATGCAGGCAGAG
GCTTCTGGAGAAAATCCTGCCGCCCTCCCCGAAGACGACGAAGTCCCCGAGGACACCGAGCACGATGA
TCCAAACTCGGATCCTGACTATTACAATGACATGCCCGCCGTGATCCCGGTGGAGGAGACTACTAAAA
GTTCTAATGCCGTCTCCATGCCCATATTCGCGGCGTTCGTAGCCTGCGCGGTCGCGCTCGTGGGCTA
CTGGTTTGGAGCATCGTAAAATGCGCGCGTAGCTAATCGAGCCTAGAATAGGTGGTTTCTTCCTACAT
GCCACGCCTCACGCTCATAATATAAATCACATGGAATAGCATACCAATGCCTATTCATTGGGACGTTC
GAAAAGCATGGCATCGCTACTTGGAACTCTGGCTCTCCTTGCCGCGACGCTCGCACCCTTCGGCGCGA
TGGGAATCGTGATCACTGGAAATCACGTCTCCGCCAGGATTGACGACGATCACATCGTGATCGTCGCG
CCTCGCCCCGAAGCTACAATTCAACTGCAGCTATTTTTTCATGCCTGGCCAGAGACCCCACAAACCCTA
CTCAGGAACCGTCCGCGTCGCGTTTCGGTCTGATATAACAAACCAGTGCTACCAGGAACTTAGCGAGG
AGCGCTTTGAAAATTGCACTCATCGATCGTCTTCTGTTTTTGTCGGCTGTAAAGTGACCGAGTACACG
TTCTCCGCCTCGAACAGACTAACCGGACCTCCACACCCGTTTAAGCTCACTATACGAAATCCTCGTCC
GAACGACAGCGGGATGTTCTACGTAATTGTTCGGCTAGACGACACCAAAGAACCCATTGACGTCTTCG
CGATCCAACTATCGGTGTATCAATTCGCGAACACCGCCGCGACTCGCGGACTCTATTCCAAGGCTTCG
TGTCGCACCTTCGGATTACCTACCGTCCAACTTGAGGCCTATCTCAGGACCGAGGAAAGTTGGCGCAA
CTGGCAAGCGTACGTTGCCACGGAGGCCACGACGACCAGCGCCGAGGCGACAACCCCGACGCCCGTCA
CTGCAACCAGCGCCTCCGAACTTGAAGCGGAACACTTTACCTTTCCCTGGCTAGAAAATGGCGTGGAT
CATTACGAACCGACACCCGCAAACGAAAATTCAAACGTTACTGTCCGTCTCGGGACAATGAGCCCTAC
GCTAATTGGGGTAACCGTGGCTGCCGTCGTGAGCGCAACGATCGGCCTCGTCATTGTAATTTCCATCG
TCACCAGAAACATGTGCACCCCGCACCGAAAATTAGACACGGTCTCGCAAGACGACGAAGAACGTTCC
CAAACTAGAAGGGAATCGCGAAAATTTGGACCCATGGTTGCGTGCGAAATAAACAAGGGGGCTGACCA

-continued

GGATAGTGAACTTGTGGAACTGGTTGCGATTGTTAACCCGTCTGCGCTAAGCTCGCCCGACTCAATAA

AAATGTGATTAAGTCTGAATGTGGCTCTCCAATCATTTCGATTCTCTAATCTCCCAATCCTCTCAAAA

GGGGCAGTATCGGACACGGACTGGGAGGGGCGTACACGATAGTTATATGGTACAGCAGAGGCCTCTGA

ACACTTAGGAGGAGAATTCAGCCGGGGAGAGCCCCTGTTGAGTAGGCTTGGGAGCATATTGCAGGATG

AACATGTTAGTGATAGTTCTCGCCTCTTGTCTTGCGCGCCTAACTTTTGCGACGCGACACGTCCTCTT

TTTGGAAGGCACTCAGGCTGTCCTCGGGGAAGATGATCCCAGAAACGTTCCGGAAGGGACTGTAATCA

AATGGACAAAAGTCCTGCGGAACGCGTGCAAGATGAAGGCGGCCGATGTCTGCTCTTCGCCTAACTAT

TGCTTTCATGATTTAATTTACGACGGAGGAAAGAAAGACTGCCCGCCCGCGGGACCCCTGTCTGCAAA

CCTGGTAATTTTACTAAAGCGCGGCGAAagctt

Dual Expression Cassette Insert (SEQ ID NO: 17): 5920 bp
gTCGACGGCAGAGTCGCAGACGCCCCTATTGGACGTCAAAATTGTAGAGGTGAAGTTTTCAAACGATG

GCGAAGTAACGGCGACTTGCGTTTCCACCGTCAAATCTCCCTATAGGGTAGAAACTAATTGGAAAGTA

GACCTCGTAGATGTAATGGATGAAATTTCTGGGAACAGTCCCGCCGGGGTTTTTAACAGTAATGAGAA

ATGGCAGAAACAGCTGTACTACAGAGTAACCGATGGAAGAACATCGGTCCAGCTAATGTGCCTGTCGT

GCACGAGCCATTCTCCGGAACCTTACTGTCTTTTCGACACGTCTCTTATAGCGAGGGAAAAAGATATC

GCGCCAGAGTTATACTTTACCTCTGATCCGCAAACGGCATACTGCACAATAACTCTGCCGTCCGGCGT

TGTTCCGAGATTCGAATGGAGCCTTAATAATGTTTCACTGCCGGAATATTTGACGGCCACGACCGTTG

TTTCGCATACCGCTGGCCAAAGTACAGTGTGGAAGAGCAGCGCGAGAGCAGGCGAGGCGTGGATTTCT

GGCCGGGGAGGCAATATATACGAATGCACCGTCCTCATCTCAGACGGCACTCGCGTTACTACGCGAAA

GGAGAGGTGCTTAACAAACACATGGATTGCGGTGGAAAACGGTGCTGCTCAGGCGCAGCTGTATTCAC

TCTTTTCTGGACTTGTGTCAGGATTATGCGGGAGCATATCTGCTTTGTACGAACGCTATGGACCGCC

ATTTATTTTTGAGGAATGCTTTTTGGACTATCGTACTGCTTTCTTCCTTCGCTAGCCAGAGCACCGCC

GCCGTCACGTACGACTACATTTTAGGCCGTCGCGCGCTCGACGCGCTAACCATACCGGCGGTTGGCCC

GTATAACAGATACCTCACTAGGGTATCAAGAGGCTGCGACGTTGTCGAGCTCAACCCGATTTCTAACG

TGGACGACATGATATCGGCGGCCAAAGAAAAAGAGAAGGGGGGCCCTTTCGAGGCCTCCGTCGTCTGG

TTCTACGTGATTAAGGGCGACGACGGCGAGGACAAGTACTGTCCAATCTATAGAAAAGAGTACAGGGA

ATGTGGCGACGTACAACTGCTATCTGAATGCGCCGTTCAATCTGCACAGATGTGGGCAGTGGACTATG

TTCCTAGCACCCTTGTATCGCGAAATGGCGCGGGACTGACTATATTCTCCCCCACTGCTGCGCTCTCT

GGCCAATACTTGCTGACCCTGAAAATCGGGAGATTTGCGCAAACAGCTCTCGTAACTCTAGAAGTTAA

CGATCGCTGTTTAAAGATCGGGTCGCAGCTTAACTTTTTACCGTCGAAATGCTGGACAACAGAACAGT

ATCAGACTGGATTTCAAGGCGAACACCTTTATCCGATCGCAGACACCAATACACGACACGCGGACGAC

GTATATCGGGGATACGAAGATATTCTGCAGCGCTGGAATAATTTGCTGAGGAAAAAGAATCCTAGCGC

GCCAGACCCTCGTCCAGATAGCGTCCCGCAAGAAATTCCCGCTGTAACCAAGAAAGCGGAAGGGCGCA

CCCCGGACGCAGAAAGCAGCGAAAAGAAGGCCCCTCCAGAAGACTCGGAGGACGACATGCAGGCAGAG

GCTTCTGGAGAAAATCCTGCCGCCCTCCCCGAAGACGACGAAGTCCCCGAGGACACCGAGCACGATGA

TCCAAACTCGGATCCTGACTATTACAATGACATGCCCGCCGTGATCCCGGTGGAGGAGACTACTAAAA

GTTCTAATGCCGTCTCCATGCCCATATTCGCGGCGTTCGTAGCCTGCGCGGTCGCGCTCGTGGGCTA

CTGGTTTGGAGCATCGTAAAATGCGCGCGTAGCTAATCGAGCCTAGAATAGGTGGTTTCTTCCTACAT

GCCACGCCTCACGCTCATAATATAAATCACATGGAATAGCATACCAATGCCTATTCATTGGGACGTTC

GAAAAGCATGGCATCGCTACTTGGAACTCTGGCTCTCCTTGCCGCGACGCTCGCACCCTTCGGCGCGA

TGGGAATCGTGATCACTGGAAATCACGTCTCCGCCAGGATTGACGACGATCACATCGTGATCGTCGCG

-continued

```
CCTCGCCCCGAAGCTACAATTCAACTGCAGCTATTTTTCATGCCTGGCCAGAGACCCCACAAACCCTA

CTCAGGAACCGTCCGCGTCGCGTTTCGGTCTGATATAACAAACCAGTGCTACCAGGAACTTAGCGAGG

AGCGCTTTGAAAATTGCACTCATCGATCGTCTTCTGTTTTTGTCGGCTGTAAAGTGACCGAGTACACG

TTCTCCGCCTCGAACAGACTAACCGGACCTCCACACCCGTTTAAGCTCACTATACGAAATCCTCGTCC

GAACGACAGCGGGATGTTCTACGTAATTGTTCGGCTAGACGACACCAAAGAACCCATTGACGTCTTCG

CGATCCAACTATCGGTGTATCAATTCGCGAACACCGCCGCGACTCGCGGACTCTATTCCAAGGCTTCG

TGTCGCACCTTCGGATTACCTACCGTCCAACTTGAGGCCTATCTCAGGACCGAGGAAAGTTGGCGCAA

CTGGCAAGCGTACGTTGCCACGGAGGCCACGACGACCAGCGCCGAGGCGACAACCCCGACGCCCGTCA

CTGCAACCAGCGCCTCCGAACTTGAAGCGGAACACTTTACCTTTCCCTGGCTAGAAAATGGCGTGGAT

CATTACGAACCGACACCCGCAAACGAAAATTCAAACGTTACTGTCCGTCTCGGGACAATGAGCCCTAC

GCTAATTGGGGTAACCGTGGCTGCCGTCGTGAGCGCAACGATCGGCCTCGTCATTGTAATTTCCATCG

TCACCAGAAACATGTGCACCCCGCACCGAAAATTAGACACGGTCTCGCAAGACGACGAAGAACGTTCC

CAAACTAGAAGGGAATCGCGAAAATTTGGACCCATGGTTGCGTGCGAAATAAACAAGGGGGCTGACCA

GGATAGTGAACTTGTGGAACTGGTTGCGATTGTTAACCCGTCTGCGCTAAGCTCGCCCGACTCAATAA

AAATGTGATTAAGTCTGAATGTGGCTCTCCAATCATTTCGATTCTCTAATCTCCCAATCCTCTCAAAA

GGGGCAGTATCGGACACGGACTGGGAGGGGCGTACACGATAGTTATATGGTACAGCAGAGGCCTCTGA

ACACTTAGGAGGAGAATTCAGCCGGGGAGAGCCCCTGTTGAGTAGGCTTGGGAGCATATTGCAGGATG

AACATGTTAGTGATAGTTCTCGCCTCTTGTCTTGCGCGCCTAACTTTTGCGACGCGACACGTCCTCTT

TTTGGAAGGCACTCAGGCTGTCCTCGGGGAAGATGATCCCAGAAACGTTCCGGAAGGGACTGTAATCA

AATGGACAAAAGTCCTGCGGAACGCGTGCAAGATGAAGGCGGCCGATGTCTGCTCTTCGCCTAACTAT

TGCTTTCATGATTTAATTTACGACGGAGGAAAGAAAGACTGCCCGCCCGCGGGACCCCTGTCTGCAAA

CCTGGTAATTTTACTAAAGCGCGGCGAAAGCTTCGCGCCAGGTCAATTCCCTGGCATTATGCCCAGTA

CATGACCTTATGGGACTTTCCTACTTGGCAGTACATCTACGTATTAGTCATCGCTATTACCATGGTGA

TGCGGTTTTGGCAGTACATCAATGGGCGTGGATAGCGGTTTGACTCACGGGGATTTCCAAGTCTCCAC

CCCATTGACGTCAATGGGAGTTTGTTTTGGCACCAAAATCAACGGGACTTTCCAAAATGTCGTAACAA

CTCCGCCCCATTGACGCAAATGGGCGGTAGCGTGTACGGTGGGAGGTCTATATAAGCAGAGCTCGTTT

AGTGAACCGTCAGATCGCCTGGAGACGCCATCCACGCTGTTTTGACCTCCATAGAAGACACCGGTTGC

GCCGCCACCATGGGCCCCAGACCTTCTACCAAGAACCCAGTACCTATGATGCTGACTGTCCGAGTCGC

GCTGGTACTGAGTTGCATCTGTCCGGCAAACTCCATTGATGGCAGGCCTCTTGCGGCTGCAGGAATTG

TGGTTACAGGAGACAAAGCCGTCAACATATACACCTCATCCCAGACAGGATCAATCATAGTTAAGCTC

CTCCCGAATCTGCCCAAGGATAAGGAGGCATGTGCGAAAGCCCCCTTGGATGCATACAACAGGACATT

GACCACTTTGCTCACCCCCCTTGGTGACTCTATCCGTAGGATACAAGAGTCTGTGACTACATCTGGAG

GGGGGAGACAGGGGCGCCTTATAGGCGCCATTATTGGCGGTGTGGCTCTTGGGGTTGCAACTGCCGCA

CAAATAACAGCGGCCGCAGCTCTGATACAAGCCAAACAAATGCTGCCAACATCCTCCGACTTAAAGA

GAGCATTGCCGCAACCAATGAGGCTGTGCATGAGGTCACTGACGGATTATCGCAACTAGCAGTGGCAG

TTGGGAAGATGCAGCAGTTTGTTAATGACCAATTTAATAAAACAGCTCAGGAATTAGACTGCATCAAA

ATTGCACAGCAAGTTGGTGTAGAGCTCAACCTGTACCTAACCGAATTGACTACAGTATTCGGACCACA

AATCACTTCACCTGCTTTAAACAAGCTGACTATTCAGGCACTTTACAATCTAGCTGGTGGAAATATGG

ATTACTTATTGACTAAGTTAGGTGTAGGGAACAATCAACTCAGCTCATTAATCGGTAGCGGCTTAATC

ACCGGTAACCCTATTCTATACGACTCACAGACTCAACTCTTGGGTATACAGGTAACTCTACCTTCAGT

CGGGAAGCTAAATAATATGCGTGCCACCTACTTGGAAACCTTATCCGTAAGCACAACCAGGGGATTTG
```

-continued

```
CCTCGGCACTTGTCCCAAAAGTGGTGACACAGGTCGGTTCTGTGATAGAAGAACTTGACACCTCATAC

TGTATAGAAACTGACTTACATTTATATTGTACAAGAATAGTAACGTTCCCTATGTCCCCTGGTATTTA

TTCCTGCTTGAGCGGCAATACGTCGGCCTGTATGTACTCAAAGACCGAAGGCGCACTTACTACACCAT

ACATGACTATCAAAGGTTCAGTCATCGCCAACTGCAAGATGACAACATGTAGATGTGTAAACCCCCCG

GGTATCATATCGCAAAACTATGGAGAAGCCGTGTCTCTAATAGATAAACAATCATGCAATGTTTTATC

CTTAGGCGGGATAACTTTAAGGCTCAGTGGGGAATTCGATGTAACTTATCAGAAGAATATCTCAATAC

AAGATTCTCAAGTAATAATAACAGGCAATCTTGATATCTCAACTGAGCTTGGGAATGTCAACAACTCG

ATCAGTAATGCTTTGAATAAGTTAGAGGAAAGCAACAGAAAACTAGACAAAGTCAATGTCAAACTGAC

TAGCACATCTGCTCTCATTACCTATATCGTGTTGACTATCATATCTCTTGTTTTTGGTATACTTAGCC

TGATTCTAGCATGCTACCTAATGTACAAGCAAAAGGCGCAACAAAAGACCTTATTATGGCTTGGGAAT

AATACTCTAGATCAGATGAGAGCCACTACAAAAATGTGAGGATCTCTCGAGGAATTCTAGATCCCACG

TCACTATTGTATACTCTATATTATACTCTATGTTATACTCTGTAATCCTACTCAATAAACGTGTCACG

CCTGTGAAACCGTACTAAGTCTCCCGTGTCTTCTTATCACCATCAGGTGACATCCTCGCCCAGGCTGT

CAATCATGCCGGTATCGATTCCAGTAGCACCGGCCCCACGCTGACAACCCACTCTTGCAGCGTTAGCA

GCGCCCCTCTTAACAAGCCGACCCCCACCAGCGTCGCGGTTACTAACACTCCTCTCCCCGACCTGCAA

CTAGT
```

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A recombinant nonpathogenic Marek's Disease Virus (rMDV$_{np}$) comprising a first nucleic acid inserted in a first nonessential site in the rMDV$_{np}$ genome and a second nucleic acid inserted in a second nonessential site in the rMDV$_{np}$ genome;

wherein the first nucleic acid comprises both a nucleotide sequence that encodes an Infectious Laryngotracheitis Virus glycoprotein D (ILTVgD) and a nucleotide sequence that encodes an Infectious Laryngotracheitis Virus glycoprotein I (ILTVgI);

wherein the second nucleic acid comprises a nucleotide sequence that encodes a Newcastle Disease Virus fusion protein (NDV F);

wherein the first nonessential site and the second nonessential site are either both the UL54.5 site or only the first nonessential site is the US2 site; and wherein the rMDV$_{np}$ is not a recombinant avian herpesvirus comprising a Marek's disease virus (MDV) unique short viral genome region, a herpesvirus of turkeys (HVT) unique long viral genome region, and the repeat viral genome regions of the HVT.

2. The rMDV$_{np}$ of claim 1, wherein the first nonessential site is the US2 site and the second nonessential site is the UL7/8 site.

3. The rMDV$_{np}$ of claim 1, wherein the nucleotide sequence encoding the ILTV gD protein is operatively under the control of a first promoter, the nucleotide sequence encoding the ILTV gI protein is operatively under the control of a second promoter, and the nucleotide sequence encoding the NDV F protein is operatively under the control of a third promoter.

4. The rMDV$_{np}$ of claim 3, wherein the first promoter, the second promoter, and the third promoter are all different.

5. The rMDV$_{np}$ of claim 4, wherein the first promoter is the endogenous ILTV gD promoter and the second promoter is the endogenous ILTV gI promoter.

6. The rMDV$_{np}$ of claim 5, wherein the third promoter is the human cytomegalovirus immediate early (hCMV IE) promoter.

7. The rMDV$_{np}$ of claim 6 that is a recombinant herpesvirus of turkeys (rHVT).

8. A vaccine comprising the rMDV$_{np}$ of claim 1.

9. The vaccine of claim 8, wherein the rMDV$_{np}$ is a recombinant herpesvirus of turkeys (rHVT).

10. The vaccine of claim 9, that further comprises a mild live infectious bursal disease virus (IBDV).

11. The vaccine of claim 10, wherein the mild live IBDV is strain 89/03.

12. A vaccine comprising the rMDV$_{np}$ of claim 2.

13. The vaccine of claim 12, that further comprises a mild live IBDV.

14. The vaccine of claim 13, wherein the mild live IBDV is strain 89/03.

15. A method for aiding in the protection of a chicken against ILTV comprising administering the vaccine of claim 14.

16. A method for aiding in the protection of a chicken against ILTV comprising administering the vaccine of claim 8.

17. The vaccine of claim 12, wherein the rMDV$_{np}$ is a recombinant herpesvirus of turkeys (rHVT).

18. The vaccine of claim 17, that further comprises an attenuated infectious bursal disease virus (IBDV).

19. A vaccine comprising the rMDV$_{np}$ of claim 5.

20. The vaccine of claim 19, wherein the rMDV$_{np}$ is a recombinant herpesvirus of turkeys (rHVT).

21. The vaccine of claim 20, that further comprises an attenuated infectious bursal disease virus (IBDV).

* * * * *